(12) United States Patent
Wandless et al.

(10) Patent No.: US 10,137,180 B2
(45) Date of Patent: Nov. 27, 2018

(54) METHODS FOR REGULATING PROTEIN FUNCTION IN CELLS IN VIVO USING SYNTHETIC SMALL MOLECULES

(71) Applicant: THE BOARD OF TRUSTEES OF THE LELAND STANFORD JUNIOR UNIVERSITY, Stanford, CA (US)

(72) Inventors: Thomas J. Wandless, Menlo Park, CA (US); Laura A. Banaszynski, New York, NY (US); Mark A. Sellmyer, Portola Valley, CA (US); Christopher H. Contag, Stanford, CA (US); Steven H. Thorne, Pittsburgh, PA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 14/020,768

(22) Filed: Sep. 6, 2013

(65) Prior Publication Data

US 2014/0010791 A1    Jan. 9, 2014

Related U.S. Application Data

(62) Division of application No. 12/437,279, filed on May 7, 2009, now Pat. No. 8,530,636.

(60) Provisional application No. 61/051,303, filed on May 7, 2008.

(51) Int. Cl.
| | | |
|---|---|---|
| *C07K 19/00* | (2006.01) |
| *A61K 38/52* | (2006.01) |
| *A61K 31/7088* | (2006.01) |
| *C07K 14/525* | (2006.01) |
| *C07K 14/55* | (2006.01) |
| *C12N 9/90* | (2006.01) |
| *A61K 31/445* | (2006.01) |
| *A61K 31/5377* | (2006.01) |
| *A61K 35/12* | (2015.01) |
| *A61K 38/00* | (2006.01) |

(52) U.S. Cl.
CPC ............ *A61K 38/52* (2013.01); *A61K 31/445* (2013.01); *A61K 31/5377* (2013.01); *A61K 31/7088* (2013.01); *C07K 14/525* (2013.01); *C07K 14/55* (2013.01); *C12N 9/90* (2013.01); *A61K 35/12* (2013.01); *A61K 38/00* (2013.01); *C07K 2319/35* (2013.01); *C12N 2799/027* (2013.01)

(58) Field of Classification Search
CPC ................................................ C07K 2319/35
See application file for complete search history.

(56) References Cited

U.S. PATENT DOCUMENTS

| | | |
|---|---|---|
| 4,442,203 A | 4/1984 | Varshavsky |
| 5,071,775 A | 12/1991 | Snapka et al. |
| 5,093,242 A | 3/1992 | Bachmair et al. |
| 5,122,463 A | 6/1992 | Varshavsky et al. |
| 5,132,213 A | 7/1992 | Bachmair et al. |
| 5,196,321 A | 3/1993 | Bachmair et al. |
| 5,212,058 A | 5/1993 | Baker et al. |
| 5,391,490 A | 2/1995 | Varshavsky et al. |
| 5,494,818 A | 2/1996 | Baker et al. |
| 5,503,977 A | 4/1996 | Johnsson et al. |
| 5,538,862 A | 7/1996 | Wu et al. |
| 5,763,212 A | 6/1998 | Varshavsky et al. |
| 5,766,927 A | 6/1998 | Baker et al. |
| 6,133,456 A | 10/2000 | Holt et al. |
| 6,150,527 A | 11/2000 | Holt et al. |
| 6,159,732 A | 12/2000 | Kwon et al. |
| 2002/0100068 A1 | 7/2002 | Chambon et al. |
| 2004/0038373 A1 | 2/2004 | Platz et al. |
| 2005/0214738 A1 | 9/2005 | Stankunas et al. |
| 2009/0215169 A1 | 8/2009 | Wandless et al. |

OTHER PUBLICATIONS

Banaszynski et al. (2006, Cell, vol. 126, pp. 995-1004).*
Clarkson et al. (1998, PNAS, vol. 95, pp. 10437-10442).*
Kaufmam et al. (2006, Human Gene Therapy, vol. 17, pp. 239-244).*
Foa et al. (1992, British J. Cancer, vol. 66, pp. 992-998).*
Iuliucci et al. (2001, J. Clin Pharmacol., vol. 41, pp. 870-879).*
Lodish et al. (2000, Molecular Cell Biology, 4th Edition, Section 17.4, 6 pages total).*
Armstrong and Goldberg, An FKBP destabilization domain modulates protein levels in plasmodium falciparum, Nature Methods, vol. 4, No. 12, pp. 1007-1009 (2007).
Banaszynski et al., "Conditional control of protein function", Chem. Biol., vol. 13, pp. 11-21 (2006).
Banaszynski et al., "A rapid, reversible, and tunable method to regulate protein function in living cells using synthetic small molecules", Cell, vol. 126, No. 5, pp. 995-1004 (2006).
Bishop et al., "Design of allele-specific inhibitors to probe protein kinase signaling", Current Biology, vol. 8, No. 5, pp. 257-266 (1998).
Choi et al., "Structure of the FKBP12-rapamycin complex interacting with the binding domain of human FRAP", Science, vol. 273, No. 5272, pp. 239-241 (1996).
Clackson et al., "Redesigning an FKBP-ligand interface to generate chemical dimerizers with novel specificity", PNAS USA, vol. 95, No. 18, pp. 10437-10442 (1998).
Dohmen et al., "Heat-inducible degron: a method dor construction temperature-sensitive mutants", Science, vol. 263, pp. 1273-1276 (1994).
Foa et al., "IL2 treatment for cancer: from biology to gene therapy", Br. J. Cancer, vol. 66, No. 6, pp. 992-998 (1992).

(Continued)

*Primary Examiner* — Thaian N Ton
*Assistant Examiner* — David A. Montanari
(74) *Attorney, Agent, or Firm* — McDermott Will & Emery LLP

(57) ABSTRACT

Methods and compositions for the rapid and reversible destabilizing of specific proteins in vivo using cell-permeable, synthetic molecules are described.

14 Claims, 33 Drawing Sheets

Specification includes a Sequence Listing.

(56) References Cited

OTHER PUBLICATIONS

Herm-Gotz et al., "Rapid control of protein level in the apicomplexan *Toxoplasma gondii*", Nature Methods, vol. 4, No. 12, pp. 1003-1009 (2007).
Holt et al., "Design synthesis, and kinetic evaluations of high-affinity FKBP ligands and the X-ray crystal structures of their complexes with FKBP12", J. Am. Chem. Soc., vol. 115, pp. 9925-9938 (1993).
Iuliucci et al., "Intravenous safety and pharmacokinetics of a novel dimerizer drug AP1903, in healthy volunteers", J. Clin. Pharmacol., vol. 41. No. 8, pp. 870-879 (2001).
Johnston et al., "Methotrexate inhibits proteolysis of dihydrofolate reductase by the N-end rule pathway", J. Biol. Chem., vol. 270, No. 14, pp. 8172-8175 (1996).
Kaufman et al., "Local delivery of vaccinia virus expressing multiple costimulatory molecules for the treatment of established tumors", Human Gene Therapy, vol. 17, No. 2, pp. 239-244 (2006).
Laporta and Comolli, "Biochemical and immunological characterization of calcium-dependent and -independent PKC isoenzymes in renal ischemia", Biochemical and Biophysical Research Communications, vol. 191, No. 3, pp. 1124-1130 (1993).
Levy et al., "Analysis of a conditional degradation signal in yeast and mammalian cells", Eur. J. Biochem., vol. 259, pp. 244-252 (1999).
Liberles et al., "Inducible gene expression and protein translocation using nontoxic ligands identified by a mammalian three-hybrid screen", PNAS USA, vol. 94, No. 15, pp. 7825-7830 (1997).
McCart et al., "Systemic cancer therapy with a tumor-selective vaccinia virus mutant lacking thymidine kinase and vaccinia growth factor genes", Cancer Research, vol. 61, No. 24, pp. 8751-8757 (2001).
Payne and Smeda, "Cerebrovascular alterations in pressure and protein kinase C-mediated constriction in Dahi salt-sensitive rats", J. Hypertension, vol. 20, No. 7, pp. 1355-1363 (2002).
Pollock and Clackson, "Dimerizer-regulated gene expression", Curr. Opin. Biotechnol., vol. 13, pp. 459-467 (2002).
Raval et al., "Protein kinase C delta cleavage initiates an aberrant signal transduction pathway after cardiac arrest and oxygen glucose deprivation", J. Cerebral Blood Flow & Metabolism, vol. 25, No. 6, pp. 730-741 (2005).
Rosengren et al., "Enhanced blood-brain barrier leakage to evans blue-labelled albumin after air embolism in ethanol-intoxicated rats", ACTA Neuropath., vol. 38, No. 2, pp. 149-152 (1977).
Shah et al., Engineering unnatural nucleotide specificity for Rous sarcoma virus tyrosine kinase to uniquity label its direct substrates, PNAS USA, vol. 94, No. 8, pp. 3565-3570 (1997).
Stanimirovic et al., "Angiotensin II-induced fluid fluid phase endocytosis in human cerebromicrovascular andothelial cells is regulated by the inositol-phosphate signaling pathway", J. Cell. Phys., vol. 169, No. 3, pp. 455-467 (1996).
Striepen, "Switching parasite proteins on and off", Nature Methods, vol. 4, No. 12, pp. 999-1000 (2007).
Thorne et al., "Synergistic antitumor effects of immune cell-viral biotherapy", Science, vol. 311, pp. 1780-1784 (2006).
Vilella-Bach et al., "The FKBP12-rapamycin-binding domain is required for FKBP12-rapamycin-associated protein kinase activity and G1 progression", J. Biol. Chem., vol. 274, No. 7, pp. 4266-4272 (1999).
Werber and Fitch-Burke, "Effect of chronic hypertension on acute hypertensive disruption of the blood-brain barrier in rats", Hypertension, vol. 12, No. 6, pp. 549-555 (1988).
Yang et al., "Investigating protein-ligand interactions with a mutant FKBP possessing a designed specificity packet", J. Med. Chem., vol. 43, No. 6, pp. 1135-1142 (2000).

\* cited by examiner

SEQ ID NO: 1
FKBP F36V

GVQVETISPG DGRTFPKRGQ TCVVHYTGML EDGKKVDSSR DRNKPFKFML 50
GKQEVIRGWE EGVAQMSVGQ RAKLTISPDY AYGATGHPGI IPPHATLVFD 100
VELLKLE 107

SEQ ID NO: 2
FKBP F15S

GVQVETISPG DGRTSPKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 3
FKBP V24A

GVQVETISPG DGRTFPKRGQ TCVAHYTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 4
FKBP H25R

GVQVETISPG DGRTFPKRGQ TCVVRYTGML EDGKKFDSSR DRNKPFKFML 50
GKQEVIRGWE EGVAQMSVGQ RAKLTISPDY AYGATGHPGI IPPHATLVFD 100
VELLKLE 107

SEQ ID NO: 5
FKBP E60G

GVQVETISPG DGRTFPKRGQ TCVVHYTGML EDGKKFDSSR DRNKPFKFML 50
GKQEVIRGWG EGVAQMSVGQ RAKLTISPDY AYGATGHPGI IPPHATLVFD 100
VELLKLE 107

SEQ ID NO: 6
FKBP L106P

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLKPE 107

FIG. 29A

SEQ ID NO: 7
FKBP D100G

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFG 100
VELLKLE 107

SEQ ID NO: 8
FKBP M66T

GVQVETISPG DGRTFPKRGQ TCVVHYTGML EDGKKFDSSR DRNKPFKFML 50
GKQEVIRGWE EGVAQTSVGQ RAKLTISPDY AYGATGHPGI IPPHATLVFD 100
VELLKLE 107

SEQ ID NO: 9
FKBP R71G

GVQVETISPG DGRTFPKRGQ TCVVHYTGML EDGKKFDSSR DRNKPFKFML 50
GKQEVIRGWE EGVAQMSVGQ GAKLTISPDY AYGATGHPGI IPPHATLVFD 100
VELLKLE 107

SEQ ID NO: 10
FKBP D100N

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFN 100
VELLKLE 107

SEQ ID NO: 11
FKBP E102G

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VGLLKLE 107

SEQ ID NO: 12
FKBP K105I

GVQVETISPG DGRTFPKRGQ TCVVHYTGML EDGKKFDSSR DRNKPFKFML 50
GKQEVIRGWE EGVAQMSVGQ RAKLTISPDY AYGATGHPGI IPPHATLVFD 100
VELLILE 107

FIG. 29B

SEQ ID NO: 13
DHFR

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

SEQ ID NO: 14
DHFR Y100I

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 15
DHFR G121V

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE VDTHFPDYEP DDWESVFSEF HDADAQNSHS 150
YCFEILERR 159

SEQ ID NO: 16
DHFR F103L

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGGRVY 100
EQLLPKAQKL YLTHIDAEVE GDTHFPDYEP DDWESVFSEF HDADAQNSHS 150
YCFEILERR 159

SEQ ID NO: 17
DHFR N18T A19V

MISLIAALAV DHVIGMETVM PWNLPADLAW FKRNTLNKPV IMGRHTWESI 50
GRPLPGRKNI ILSSQPSTDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

SEQ ID NO: 18
Diversity Sequence

TRGVEEVAEGVVLLRRRGN

FIG. 29C

SEQ ID NO: 19
H12Y/Y100I

MISLIAALAV DYVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 20
H12L/Y100I

MISLIAALAV DLVIGMENAM PWNLPADLAW FKRNTLNKPV IMGRHTWESI 50
GRPLPGRKNI ILSSQPSTDD RVTWVKSVDE AIAACGDVPE IMVIGGGRVI 100
EQFLPKAQKL YLTHIDAEVE GDTHFPDYEP DDWESVFSEF HDADAQNSHS 150
YCFEILERR 159

SEQ ID NO: 21
R98H/F103S

MISLIAALAV DHVIGMENAM PWNLPADLAW FKRNTLNKPV IMGRHTWESI 50
GRPLPGRKNI ILSSQPSTDD RVTWVKSVDE AIAACGDVPE IMVIGGHVY 100
EQSLPKAQKL YLTHIDAEVE GDTHFPDYEP DDWESVFSEF HDADAQNSHS 150
YCFEILERR 159

SEQ ID NO: 22
M42T/H114R

MISLIAALAV DHVIGMENAM PWNLPADLAW FKRNTLNKPV ITGRHTWESI 50
GRPLPGRKNI ILSSQPSTDD RVTWVKSVDE AIAACGDVPE IMVIGGGRVY 100
EQFLPKAQKL YLTRIDAEVE GDTHFPDYEP DDWESVFSEF HDADAQNSHS 150
YCFEILERR 159

SEQ ID NO: 23
I61F/T68S

MISLIAALAV DHVIGMENAM PWNLPADLAW FKRNTLNKPV IMGRHTWESI 50
GRPLPGRKNI FLSSQPSSDD RVTWVKSVDE AIAACGDVPE IMVIGGGRVY 100
EQFLPKAQKL YLTHIDAEVE GDTHFPDYEP DDWESVFSEF HDADAQNSHS 150
YCFEILERR 159

FIG. 29D

METHODS FOR REGULATING PROTEIN FUNCTION IN CELLS IN VIVO USING SYNTHETIC SMALL MOLECULES

CROSS-REFERENCE TO RELATED APPLICATIONS

This application is a Divisional of U.S. patent application Ser. No. 12/437,279 filed May 7, 2009, granted as U.S. Pat. No. 8,530,636, which claims the benefit of U.S. Provisional Application No. 61/051,303 filed May 7, 2008, each of which is incorporated by reference herein in its entirety.

STATEMENT REGARDING GOVERNMENT INTEREST

This invention was made with Government support under contracts GM068589 and GM073046 awarded by the National Institutes of Health. The Government has certain rights in this invention.

REFERENCE TO SEQUENCE LISTING, TABLE OR COMPUTER PROGRAM

A Sequence Listing is being submitted with this application in the form of a text file, created 4 Sep. 2013 named "0915110572seq.txt" (26,749 bytes), the contents of which are incorporated herein by reference in their entirety.

TECHNICAL FIELD

Methods and compositions for the rapid and reversible destabilizing of specific proteins in vivo using cell-permeable, synthetic molecules are described.

BACKGROUND

Techniques that target gene function at the level of DNA and mRNA provide powerful methods for modulating the expression of proteins encoded by specific genes. For example, the tet/dox and Cre/lox systems have been widely used to target gene expression at the transcriptional level (Ryding, A. D. S. et al. (2001) *J. Endocrinol.* 171:1-14) and RNA interference is rapidly being adopted as a method to achieve post-transcriptional gene silencing (Fire, A. at al. (1998) *Nature* 391:806-811; Medema, R. H. (2004) *Biochem. J.* 380:593-603; Raab, R. M. and Stephanopoulos, G. (2004) *Biotechnology & Bioengineering* 88:121-132).

However, methods for regulating protein function directly are limited, especially in mammalian cells. Inhibitors or activators of particular proteins have been identified, and often take the form of cell-permeable small molecules. Many of these molecules have found widespread use as biological probes, often because the speed, dosage-dependence, and reversibility of their activities, which complement methods for genetically modulating gene expression (Schreiber, S. L. (2003) *Chem. & Eng. News* 81:51-61). However these inhibitors or activators are often promiscuous, affecting several proteins rather than a specific protein (Davies, S. P. et al. (2000) *Biochem. J.* 351:95-105; Bain, J. et al. (2003) *Biochem. J.* 371:199-204; Godl, K. et al. (2003) *Proc. Natl. Acad. Sci. U.S.A.* 100:15434-15439; Tan, D. S. (2005) *Nat. Chem. Biol.* 1:74-84; Mayer, T. U. et al., (1999) *Science,* 286:971-974).

Shokat and coworkers have developed a method by which specific kinases can be inhibited using a small-molecule modulator (Shah et al., 1997; Bishop, A. C. et al. (1998) *Current Biology* 8:257-266). This method involves mutating the protein of interest, typically replacing a large conserved residue in the active site with a smaller residue, such as glycine or alanine. Specificity is achieved by chemically modifying a promiscuous inhibitor to include a bulky side-chain substituent (e.g., R-group), which fills the corresponding cavity in the binding site of the modified protein of interest, while preventing productive interactions with other kinases. While this so-called "bump-hole" approach has been successful both in cultured cells and in mice (Bishop, A. C. et al. (2000) *Nature* 407:395-401; Wang, H. et al. (2003) *Proc. Natl. Acad. Sci. U.S.A.* 100:4287-4292, Chen, X. et al. (2005) *Neuron* 46:13-21), it appears to be limited to ATPases and GTPases. Additional methods are required to probe the function of a wider variety of proteins.

Other investigators have devised alternative strategies to perturb protein function by exploiting existing cellular processes (Banaszynski, L. A. et al. (2006) *Chem. Biol.* 13:11-21). For example, Varshaysky and coworkers developed methods for controlling protein function based on the importance of certain N-terminal residues for protein stability (Bachmair, A. et al. (1986). *Science* 234:179-186). Szostak and coworkers showed that a small peptide sequence could be fused to the N-terminus of a protein of interest to modulate protein stability (Park, E-C. et al. (1992) *Proc. Natl. Acad. Sci. U.S.A.* 89:1249-1252). Varshaysky and coworkers have further isolated a temperature-sensitive peptide sequence that greatly reduced the half-life or dihydrofolate reductase (DHFR) at the non-permissive temperatures (Dohmen, R. J. et al. (1994) *Science* 263:1273-1276). This approach has been used to study proteins in yeast (Labib, K. et al. (2000) *Science* 288:1643-1646; Kanemaki, M. et al. (2003) *Nature* 423:720-724). More recently, several researchers have engineered systems in which dimeric small molecules are used to conditionally target fusion proteins for degradation via E3 ligase or the proteasome, itself (Schneekloth et al., 2004; Janse, D. M. et al. (2004) *J. Biol. Chem.* 279:21415-21420). However, these systems require either a prior knowledge of the high-affinity ligands that modulate the activity of a protein of interest or they are restricted to genetically engineered yeast strains.

An alternative approach for controlling protein function directly is to interfere with subcellular localization. Several methods are available to regulate protein localization using small-molecule by taking advantage of the FKBP-rapamycin-FRB ternary complex (Kohler, J. J. and Bertozzi, C. R. (2003) *Chem. Biol.* 10:1303-1331 and Inoue, T. et al., (2005) *Nature Methods* 2:415-418). Rapamycin and FK506 are potent, commercially available immunosuppressive agents, which are ligands of the FK506-binding protein (FKBP12, FKBP). Rapamycin also binds to FKBP-rapamycin-associated protein (FRAP). FRAP is also called the mammalian target of rapamycin (mTOR), rapamycin and FKBP target 1 (RAFT1), and FRB. Rapamycin binds to and inhibits mTOR by interacting with its FKBP-rapamycin-binding (FRB) domain to inhibit/delay G1 cell cycle progression in mammalian cells (see, e.g., Choi, J. et al. (1996) Science 273: 239-42 and Vilella-Bach, M. et al. (1999) J. Biol. Chem. 274:4266-72. The FKBP-rapamycin-binding domain is required for FKBP-rapamycin-associated protein kinase activity and G1 progression. Fusions of proteins of interest can be made to either FKBP or to the FRP domain of FRAP/mTOR. Colocalization of the protein of interest is induced upon addition of rapamycin.

Because rapamycin has inherent biological activity, researchers have developed a "bump-hole" strategy (similar to that employed by Shokat and coworkers), wherein rapamycin derivatives possessing large substituents at the FRB binding interface bind poorly to wild-type FRB and in turn the biologically relevant target FRAP/mTOR, with binding restored upon introduction of compensatory cavity-forming mutations in FRB. Specifically, a C20-methallyl-rapamycin derivative (MaRap) binds to a triple-mutated variant of FRB called FRB* (Liberles, S. D. et al. (1997) *Proc. Natl. Acad. Sci. U.S.A.* 94:7825-7830).

While these methods for regulating protein function directly are noteworthy, there has yet to be described a convenient, general method for regulating protein function, particularly a method that does not require the interaction of multiple proteins. Improved methods for regulating protein function directly, particularly in mammalian cells and in animals, are needed.

BRIEF SUMMARY

Compositions, systems, and methods for modulating the stability of proteins in vitro and in vivo using cell-permeable small molecules are described. Proteins of interest are fused to a stability-affecting protein capable of interacting with a small-molecule ligand, the presence, absence, or amount of which is used to modulate the stability of the fusion protein.

In one aspect, an in vivo conditional protein stability system is provided comprising a nucleic acid sequence encoding a fusion protein that comprises a protein of interest fused to a single-polypeptide chain, ligand-dependent, stability-affecting protein derived from a naturally-occurring ligand binding protein, and a ligand that binds to the stability-affecting protein to modulate stability of the stability-affecting protein, wherein upon introduction of the nucleic acid sequence to a eukaryotic cell the fusion protein is expressed and the stability of the fusion protein can be modulated by administering the ligand to the eukaryotic cell.

In one embodiment, the single-polypeptide chain, ligand-dependent, stability-affecting protein is a FKBP variant protein. In another embodiment the naturally-occurring ligand binding protein is a naturally occurring or wildtype FKBP protein.

In some embodiments, the protein of interest is a reporter protein. In some embodiments, the protein of interest is a therapeutic protein.

In one embodiment, the protein of interest is a cytokine. In yet another embodiment, the protein of interest is TNF-α or IL-2.

In one embodiment, the ligand is Shield1.

In one embodiment, the stability-affecting protein destabilizes the protein of interest or fusion protein in the absence of a ligand. In another embodiment, the stability-affecting protein does not destabilize the protein of interest in the presence of ligand. In yet another embodiment, the stability-affecting protein destabilizes the protein of interest or fusion protein in the absence of the ligand to a greater degree or extent than it destabilizes the protein of interest in the presence of the ligand.

In one embodiment, the stability-affecting protein destabilizes the protein of interest or fusion protein in the presence of a ligand. In yet another embodiment, the stability-affecting protein does not destabilize the protein of interest or fusion protein in the absence of ligand. In yet another embodiment, the stability-affecting protein destabilizes the protein of interest or fusion protein in the presence of the ligand to a greater degree or extent than it destabilizes the protein of interest or fusion protein in the absence of the ligand.

In some embodiments, the stability-affecting protein destabilizes the protein of interest by causing an increase in the degradation or destruction of the protein of interest or the fusion protein when not bound to the ligand as compared to the level of degradation of the protein of interest or the fusion protein when the stability-affecting protein is bound to the ligand.

In one embodiment, the ligand binds preferably to the single-polypeptide chain, ligand-dependent, stability-affecting protein as compared to the naturally-occurring ligand binding protein.

In one embodiment, the eukaryotic cells are transformed with the nucleic acid. In another embodiment, the eukaryotic cells are transformed with the nucleic acid to produce stably transformed eukaryotic cells. In another embodiment, the transformed eukaryotic cells are implanted into an animal. In yet another embodiment, the transformed eukaryotic cells are implanted into immunodeficient mice as xenografts.

In one embodiment, the nucleic acid sequence is in a viral vector. In another embodiment, the viral vector is a pox virus. In yet another embodiment, the viral vector is a vaccinia virus. In yet another embodiment, the viral vector is a vvDD.

In one embodiment, the ligand is administered to the eukaryotic cells in culture. In another embodiment, the ligand is administered to the cells by injecting the ligand into the animal intraperitoneally or intravenously.

In another aspect, a method for modulating stability of a protein of interest in vivo comprising introducing into a eukaryotic cell a nucleic acid comprising a polynucleotide which encodes a fusion protein wherein the fusion protein comprises a protein of interest and a single-polypeptide chain, ligand-dependent, stability-affecting protein derived from a naturally-occurring ligand binding protein, and administering a ligand to the eukaryotic cell is provided wherein the ligand binds to the single-polypeptide chain, ligand-dependent, stability-affecting protein to modulate stability of the fusion protein.

In one embodiment the single-polypeptide chain, ligand-dependent, stability-affecting protein is a FKBP variant protein. In another embodiment the naturally-occurring ligand binding protein is a naturally occurring or wildtype FKBP protein.

In some embodiments, the protein of interest is a reporter protein. In some embodiments, the protein of interest is a therapeutic protein.

In one embodiment, the protein of interest is a cytokine. In yet another embodiment, the protein of interest is TNF-α or IL-2.

In one embodiment, the ligand is Shield1.

In one embodiment, the stability-affecting protein destabilizes the protein of interest or fusion protein in the absence of a ligand. In another embodiment, the stability-affecting protein does not destabilize the protein of interest or fusion protein in the presence of ligand. In yet another embodiment, the stability-affecting protein destabilizes the protein of interest or fusion protein in the absence of the ligand to a greater degree or extent than it destabilizes the protein of interest or fusion protein in the presence of the ligand.

In yet another embodiment, the stability-affecting protein destabilizes the protein of interest or fusion protein in the presence of a ligand. In yet another embodiment, the stability-affecting protein does not destabilize the protein of interest or fusion protein in the absence of ligand. In yet another embodiment, the stability-affecting protein destabilizes the protein of interest or fusion protein in the presence of the ligand to a greater degree or extent than it destabilizes the protein of interest or fusion protein in the absence of the ligand.

In one embodiment, the ligand binds preferably to the single-polypeptide chain, ligand-dependent, stability-affecting protein as compared to the naturally-occurring ligand binding protein.

In one embodiment, the nucleic acid sequence is introduced into the eukaryotic cell by transforming the eukaryotic cell in culture with a plasmid comprising the nucleic acid to produce stably transformed eukaryotic cells. In another embodiment, the stably transformed eukaryotic cells are administered to an animal. In yet another embodiment, the stably transformed eukaryotic cells are transplanted into a mouse. In yet another embodiment, the stably transformed eukaryotic cells are transplanted as a xenograft into an immunodeficient mouse.

In one embodiment, the nucleic acid sequence is introduced into the eukaryotic cell by transforming the eukaryotic cell in culture with a viral vector which comprises the nucleic acid sequence. In another embodiment, the nucleic acid is introduced into the eukaryotic cell by administering to an animal a viral vector which comprises the nucleic acid sequence. In yet another embodiment, the animal has tumor cells.

In another aspect, a method for modulating cellular proliferation in an animal, comprising administering to the animal a nucleic acid comprising a polynucleotide which encodes a fusion protein wherein the fusion protein comprises a protein of interest and a single-polypeptide chain, ligand-dependent, stability-affecting protein derived from a naturally-occurring ligand binding protein, and administering a ligand which binds preferably to the single-polypeptide chain, ligand-dependent, stability-affecting protein as compared to the naturally-occurring ligand binding protein is provided.

In one embodiment the single-polypeptide chain, ligand-dependent, stability-affecting protein is a FKBP variant protein. In another embodiment the naturally-occurring ligand binding protein is a naturally occurring or wildtype FKBP protein.

In some embodiments, the protein of interest is a reporter protein. In some embodiments, the protein of interest is a therapeutic protein.

In one embodiment, the protein of interest is a cytokine. In yet another embodiment, the protein of interest is TNF-α or IL-2.

In one embodiment, the ligand is Shield1.

In one embodiment, the stability-affecting protein destabilizes the protein of interest in the absence of a ligand. In another embodiment, the stability-affecting protein does not destabilize the protein of interest in the presence of ligand. In yet another embodiment, the stability-affecting protein destabilizes the protein of interest or fusion protein in the absence of the ligand to a greater degree or extent than it destabilizes the protein of interest or fusion protein in the presence of the ligand.

In yet another embodiment, the stability-affecting protein destabilizes the protein of interest in the presence of a ligand. In yet another embodiment, the stability-affecting protein does not destabilize the protein of interest in the absence of ligand. In yet another embodiment, the stability-affecting protein destabilizes the protein of interest or fusion protein in the presence of the ligand to a greater degree or extent than it destabilizes the protein of interest or fusion protein in the absence of the ligand.

In one embodiment, the ligand binds preferably to the single-polypeptide chain, ligand-dependent, stability-affecting protein as compared to the naturally-occurring ligand binding protein.

In one embodiment, the method of administering the nucleic acid to the animal comprises transforming a eukaryotic cell with the nucleic acid to produce a stably transformed eukaryotic cell and implanting the stably transformed eukaryotic cell into the animal.

In one embodiment, the eukaryotic cells are tumor cells and administering the ligand to the animal modulates establishment, progression, and/or growth of the tumor. In another embodiment, administering the ligand to the animal inhibits tumor growth. In another embodiment, administering the ligand improves survival of the animal.

In one embodiment, the animal has tumor cells and administering the nucleic acid to the animal comprises administering a viral vector or virus to the animal, wherein the viral vector or virus harbors the nucleic acid. In another embodiment, the viral vector or virus is a pox virus. In yet another embodiment, the viral vector or virus is a vaccinia virus. In yet another embodiment, the viral vector or virus is a vvDD virus.

In another aspect, a method for modulating tumor establishment, tumor progression and/or tumor growth in an animal is provided, comprising introducing into cells of the animal a nucleic acid sequence encoding a fusion protein comprising a therapeutic protein and a single-polypeptide chain, ligand-dependent, stability-affecting protein, and controlling expression of the therapeutic protein by administering a preselected amount of the ligand, is provided wherein the ligand binds to the stability-affecting protein to modulate the stability of the therapeutic protein and the therapeutic protein modulate tumor progression or development.

In some embodiments, the nucleic acid sequence is in a plasmid. In some embodiments, the nucleic acid sequence is in a viral vector.

In some embodiments, the stability-affecting protein destabilizes the protein of interest in the absence of the ligand. In another embodiment, the stability-affecting protein does not destabilize the protein in the presence of the ligand.

In some embodiments, the ligand preferentially binds to the stability-affecting protein compared to the corresponding naturally-occurring ligand-binding protein.

In some embodiments, the stability-affecting protein is a variant FKBP protein and the fusion protein is stabilized in the presence of a FKBP ligand. In particular embodiments, the FKBP ligand is Shield1.

In some embodiments, the therapeutic protein is a cytokine. In particular embodiments, the therapeutic protein is interleukin-2.

In one embodiment, the ligand is administered by intraperitoneal or intravenous injection of the ligand into animal.

In some embodiments, the therapeutic protein modulates tumor establishment. In some embodiments, the therapeutic protein modulates tumor progression. In some embodiments, the therapeutic protein prevents tumor establishment or progression. In some embodiments, the therapeutic protein prevents or inhibits tumor growth.

In one aspect, an in vivo conditional protein stability system is provided, comprising a nucleic acid sequence encoding a fusion protein that includes a protein of interest fused in-frame to a single-polypeptide chain, ligand-dependent, stability-affecting protein derived from a naturally-occurring ligand binding protein, and a ligand that binds to the stability-affecting protein to modulate its stability, wherein upon introduction of the nucleic acid sequence to cells of an organism the fusion protein is expressed and the stability of the fusion protein can be modulated by amount of ligand present in the cells of the organism.

In some embodiments, the stability-affecting protein destabilizes the protein of interest in the absence of the ligand and does not destabilize the protein in the presence of the ligand. In some embodiments, the stability-affect protein destabilizes the protein of interest in the absence of the ligand to a greater degree or extent than in the presence of the ligand.

In some embodiments, the stability-affecting protein does not destabilize the protein of interest in the absence of the ligand and destabilizes the protein in the presence of the ligand. In some embodiments, the stability-affect protein destabilizes the protein of interest in the presence of the ligand to a greater degree or extent than in the absence of the ligand.

In some embodiments, the ligand preferentially binds to the stability-affecting protein compared to the naturally-occurring ligand-binding protein.

In some embodiments, the stability-affecting protein is a variant FKBP protein and the fusion protein is stabilized in the presence of a FKBP ligand. In particular embodiments, the FKBP ligand is Shield1.

In some embodiments, the protein of interest is a reporter protein. In some embodiments, the protein of interest is a therapeutic protein.

In a related aspect, a method of using the described in vivo conditional protein stability system for controlling the expression of protein is provided. In some embodiments, the protein of interest is a reporter protein or a therapeutic protein.

In another aspect, a method for modulating tumor establishment or progression in an animal is provided, comprising introducing into cells of the animal a nucleic acid sequence encoding a fusion protein that includes a therapeutic protein fused in-frame to a single-polypeptide chain, ligand-dependent, stability-affecting protein, and controlling expression of the therapeutic protein by administering a preselected amount of the ligand, wherein the ligand binds to the stability-affecting protein to modulate the stability of the therapeutic protein and the therapeutic protein modulate tumor progression or development.

In some embodiments, the nucleic acid sequence is in a plasmid. In some embodiments, the nucleic acid sequence is in a viral vector.

In some embodiments, the stability-affecting protein destabilizes the protein of interest in the absence of the ligand and stabilizes the protein in the presence of the ligand.

In some embodiments, the ligand preferentially binds to the stability-affecting protein compared to the corresponding naturally-occurring ligand-binding protein.

In some embodiments, the stability-affecting protein is a variant FKBP protein and the fusion protein is stabilized in the presence of a FKBP ligand. In particular embodiments, the FKBP ligand is Shield1.

In some embodiments, the therapeutic protein is a cytokine. In particular embodiments, the therapeutic protein is interleukin-2.

In some embodiments, the therapeutic protein modulates tumor establishment. In some embodiments, the therapeutic protein modulates tumor progression. In some embodiments, the therapeutic protein prevents tumor establishment or progression.

In addition to the exemplary aspects and embodiments described above, further aspects and embodiments will become apparent by reference to the drawings and by study of the following descriptions.

BRIEF DESCRIPTION OF THE DRAWINGS

(FIG. 1A) A genetic fusion of a destabilizing domain (DD) to a protein of interest (POI) results in degradation of the entire fusion protein. Addition of a ligand for the destabilizing domain protects the fusion protein from degradation. (FIG. 1B) Synthetic ligands SLF* and Shield1 for FKBP F36V.

(FIG. 2A) Fluorescence of FKBP-YFP fusion proteins expressed in NIH3T3 cells as determined by flow cytometry in the absence of Shield1. (FIG. 2B) NIH3T3 cells stably expressing FKBP-YFP fusion proteins were treated with three-fold dilutions of Shield1 (1 μM to 0.1 nM) and the fluorescence was monitored by flow cytometry. (FIG. 2C) NIH3T3 cells stably expressing FKBP-YFP fusion proteins were either mock-treated (circles) or treated with 30 nM Shield1 (squares), 100 nM Shield1 (diamonds), 300 nM Shield1 (crosses), or 1 μM Shield1 (triangles). Fluorescence was monitored over time using flow cytometry. MFI was normalized to 100% of cells treated with 1 μM Shield1 at 24 hrs. (FIG. 2D) NIH3T3 cells stably expressing FKBP-YFP fusion proteins were treated with 1 μM Shield1 for 24 hours at which point the cells were washed with media to remove Shield1, and the decrease in fluorescence was monitored using flow cytometry.

(FIG. 2E) FKBP-YFP fusion proteins were either mock-treated or treated with 1 μM Shield1 for 24 hrs then subjected to immunoblot analysis with an anti-FKBP antibody. (FIG. 2F) NIH3T3 cells stably expressing F15S-YFP and L106P-YFP were treated with 1 μM Shield1 for 24 hrs. The cells were then washed with media and treated with 10 μM MG132 in the presence or absence of 1 μM Shield1 for 4 hrs. Immunoblot analysis was performed using an anti-YFP antibody. (FIG. 2G) HeLa cells were transfected with siRNA against lamin A/C and monitored over time. The time required for the reduction of lamin A/C was compared to the time required for degradation of L106P-YFP upon removal of Shield1 from NIH3T3 cells stably expressing the fusion protein.

(FIG. 4A) FKBP variants F15S and L106P were fused to the N-termini of several different proteins and transduced into NIH3T3 cells. Cell populations stably expressing the fusions were then either mock-treated or treated with 1 µM Shield1, and cell lysates were subjected to immunoblot analysis using antibodies specific for the protein of interest. Endogenous proteins served as loading controls (when detected) and Hsp90 served as a loading control otherwise. (FIG. 4B) FKBP variants D100G and L106P were fused to the C-termini of several different proteins of interest and treated as above.

(FIG. 16A) Y100I and G121V mutants. (FIG. 16B) F103L and N18T/A19V mutants.

FIG. 21B shows quantification of the results from FIG. 21A. Mice were treated i.p. with Shield1 at 3 mg/kg (diamonds), 6 mg/kg (inverted triangles), or 10 mg/kg (triangles) and imaged over time (FIG. 21C). Mice bearing HCT116-tsLuc xenografts were either untreated (squares) or treated with Shield1 (10 mg/kg, triangles) every 48 hr and imaged over time (FIG. 21D). Data for FIG. 21B-21D are presented as the average bioluminescence detected within regions of interest drawn around the tumors±SEM (n=4 to 10).

FIG. 22A shows a graph resulting from an experiment in which HCT116 L-L106P-IL-2 cells were treated with various concentrations of Shield1 and culture media was assayed for the presence of IL-2. Data are represented as the average IL-2 concentration±SEM (n=3). FIG. 22B shows a graph resulting from an experiment in which CD1 nu–/nu– mice bearing subcutaneous HCT116 L-L106P-IL-2 tumors were either untreated (diamonds) or treated i.p. with Shield1 at 5 mg/kg (triangles) or 10 mg/kg (inverted triangles) every 48 hr beginning 5 days post-transplantation (arrow). Alternatively, mice received HCT116 L-L106P-IL-2 cells that had been pre-treated with 1 µM Shield1 for 24 hr, and were then treated with Shield1 (10 mg/kg) every 48 hr beginning on day 0 (squares). Tumor volume was determined by caliper measurement and monitored over time. Data are represented as the average tumor volume±SEM (n=5). At Day 16, all Shield1 treated groups displayed significantly reduced tumor burden relative to controls (p=0.0019 for 10 mg/kg; 0.0002 for 5 mg/kg and 0.0046 for pre-treat group). FIG. 22C shows a graph resulting from an experiment in which tumors from mice treated with Shield1 post-transplantation were collected 48 hr after the start of Shield1 treatment, weighed ex vivo, homogenized, and the concentration of IL-2 per gram tumor tissue determined by ELISA (n=4). Tumors from mice treated with Shield1 at 10 mg/kg contained significantly higher levels of IL-2 than tumors from mice treated at 5 mg/kg (p=0.032), which in turn produced more IL-2 than tumors from untreated mice (p=0.0028). FIG. 22D shows a graph resulting from an experiment in which mice treated with Shield1 post-transplantation were bled 48 hr after the start of Shield1 treatment, and the concentration of IL-2 in the serum was determined by ELISA. Shield1 treatment at 10 mg/kg (n=7) produced significantly higher levels of serum IL-2 relative to control mice (n=6, p=0.0004), whereas treatment at 5 mg/kg (n=6) did not produce any increase in serum IL-2 levels.

FIG. 23A shows a graph resulting from an experiment in which HCT116 cells were infected with vvDD L106P-tsLuc and then mock treated (squares) or treated with Shield1 at 1 µM (triangles), 100 nM (inverted triangles), or 10 nM (diamonds). Data are represented as the average luminescence±SEM (n=3). FIG. 23B shows a graph resulting from an experiment in which SCID mice bearing subcutaneous HCT116 xenografts (50-100 mm3) received a single tail vein injection of vvDD L106P-tsLuc (1×10$^8$ PFU/mouse), and after 72 hours were either untreated (C, control) or treated with Shield1 (10 mg/kg, mice 1-4). Bioluminescent signals were imaged over time. FIG. 23C is a graph showing quantification of the bioluminescent signals produced from the indicated regions of interest around the tumors shown in FIG. 23B. Data presented are the average bioluminescence±SEM (n=4).

As shown in FIG. 24A, Shield1 treatment starting 72 hr after vvDD administration (vvDD+Shield1) resulted in significantly greater levels of viral gene expression in the tumor than when Shield1 treatment was started prior to vvDD administration (vvDD Pre-Shield1; p=0.035 at 2 days; p=0.035 at 4 days and p=0.002 at 7 days). FIG. 24B shows a Kaplan-Meier survival graph relating to mice treated with Shield1 and vvDD in various combinations.

FIGS. 29A to 29D show a list of sequences referred to in the application.

DETAILED DESCRIPTION

Figure 1A:
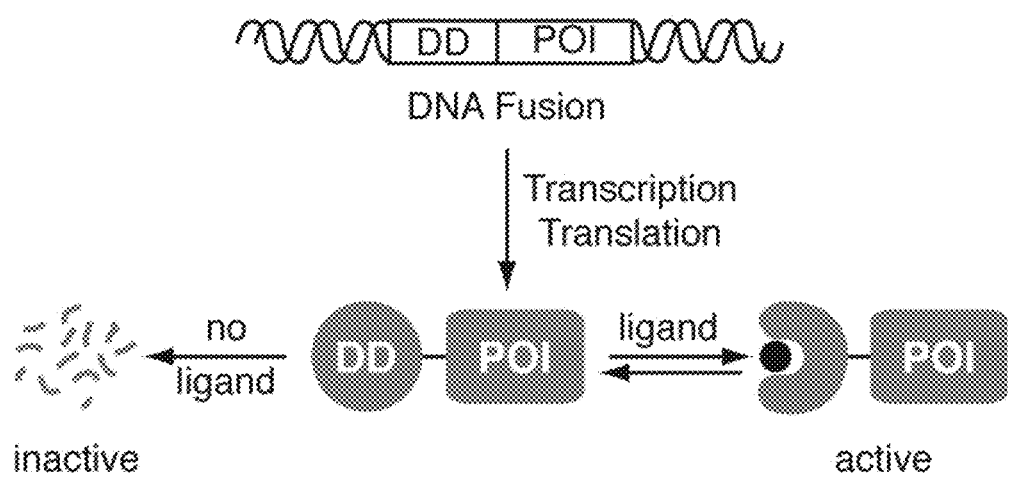
FIGS. 1A and 1B are diagrams illustrating a method for conditionally controlling protein stability.

Any methods and materials similar or equivalent to those described herein can be used in the practice or testing of the teachings herein. All publications mentioned herein are incorporated herein by reference in their entirety for the purpose of describing and disclosing the methodologies which are reported in the publications which might be used in connection with the teachings herein.

1. DEFINITIONS

It must be noted that as used herein and in the appended claims, the singular forms "a," "an," and "the" include plural reference unless the context clearly dictates otherwise.

As used herein, a "protein of interest" or "POI" is any protein, or functional fragment or derivative, thereof, that one skilled in the art wishes to study.

As used herein, "preferentially binds" means to bind with greater efficiency to a subject molecule (such as a particular amino acid sequence) than another molecule. The difference in binding efficiency may be 5-fold, 10-fold, 50-fold, 100-fold, 500-fold, 1.000-fold, 10,000 fold, or more.

As used herein, "introduction of nucleic to cells" means transfection, transduction (infection), or transformation of nucleic acids (e.g., DNA) into cells, such that the nucleic acids may be used by the cell to express a protein of interest.

As used herein, "degradation" or "destruction" of a protein means its hydrolysis into smaller proteins or amino acids, such as by the cellular proteosome.

"Rapamycin" is a naturally-occurring, small molecule immunosuppressant that is a ligand for FKBP.

"FKBP12" or "FKBP" is a 12 kDa protein that binds to the small-molecules rapamycin and FK506. The rapamycin-FKBP complexes can bind to the FRB domain of FRAP.

"FRAP," "mTOR," or "FRAP/mTOR" is a protein that binds, via its FRB domain, to rapamycin, or the FKBP-rapamycin complex.

A "FKBP variant" refers to a protein wherein one or more amino acid residues, e.g., at positions 15, 24, 25, 36, 60, 100, and 106, are substituted for an amino acid other than the amino acid in the FKBP F36V protein (SEQ ID NO: 1). Other amino acid positions that can be substituted are indicated in the Tables and Figures.

"FRB*" is a FRB variant with three point mutations, i.e., K2095P/T2098L/W2101F (using mTOR numbering), designed to bind rapamycin analogs such as MaRAP. Amino acid substitutions, or point mutations, are denoted herein, and in accord with conventional practice, as the old (original) residue in single-letter code, followed by its codon location, followed by the substitute (mutant) amino acid in single-letter code. For example, the F36V mutant of FKBP has Val in place of Phe at position 36 of the FKBP protein.

"MaRAP" is C20-methallylrapamycin, a synthetic rapamycin derivative that binds FRB* but not FRB.

"Shield1" is a synthetic small molecule that binds to wild-type FKBP, a FKBP variant having a F36V mutation/substitution, and likely other FKBP variants. Binding is about 1.000-fold tighter to the F36V variant compared to wild-type FKBP (Clackson, T. et al. (1998) *Proc. Natl. Acad. Sci. U.S.A.* 95:10437-10442).

As used herein, a "single-protein, ligand-dependent destabilization protein," "single-polypeptide chain, ligand-dependent, stability-affecting protein", "single protein, stability-affecting protein," or "stability-affecting protein" is a single polypeptide that functions as a ligand-dependent destabilization protein, as described herein. Such a destabilizing protein does not require the formation of a ternary complex, as is the case with the FKBP-rapamycin-FRB complex. A particular species is a "single-domain," ligand-dependent destabilization protein, wherein the single polypeptide comprises only a single domain (i.e., folded structure or functional unit as determined by X-ray crystallography, protease digestion, computer modeling, etc.

As used herein, "fused" means arranged in-frame as part of the same contiguous sequence of amino acids in a polypeptide. Fusion can be direct such there are no additional amino acid residues or via a linker to improve performance or add functionality.

As used herein, "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

As used herein, the terms "domain" and "region" are used interchangeably herein and refer to a contiguous sequence of amino acids within a POI or destabilizing domain, typically characterized by being either conserved or variable and having a defined function, such as ligand binding, conferring stability or instability, enzymatic function, etc.

As used herein, the terms "protein" and "polypeptide" are used interchangeably and without distinction to refer to a compound made up of a chain of amino acid residues linked by peptide bonds. Unless otherwise indicated, the sequence for peptides is given in the order from the "N" (or amino) terminus to the "C" (or carboxyl) terminus. It is understood that polypeptides include a contiguous sequence of amino acid residues.

A peptide or peptide fragment is "derived from" a parent peptide or polypeptide if it has an amino acid sequence that is homologous to, but not identical to, the parent peptide or polypeptide, or of a conserved fragment from the parent peptide or polypeptide.

Two amino acid sequences or two nucleotide sequences are considered "homologous" if they have an alignment score of >5 (in standard deviation units) using the program ALIGN with the mutation gap matrix and a gap penalty of 6 or greater (Dayhoff, M. O., in Atlas of Protein Sequence and Structure (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, 70%, 80%, 90%, 95%, or even 98% identical when optimally aligned using the ALIGN program mentioned above.

"Modulate" intends a lessening, an increase, or some other measurable change, e.g., in the stability or biological function of a protein.

A "small molecule ligand" is a discrete small-molecule, well known in the pharmaceutical and material sciences, which is to be distinguished from, e.g., a polypeptide or nucleic acid, which is a polymer consisting of monomeric subunits. Small molecule ligands may be naturally-occurring or synthetic as exemplified by pharmaceutical products, laboratory reagents, and the like.

"ddVV" refers to a Vaccinia virus having a double-deletion as described in Thorne et al. (2006) *Science*, 311: 1780-1784; McCart et al. (2001) *Cancer Res.* 61:8751-8757.

As used herein, a "variant" protein is a protein having an amino acid sequence that does not occur in nature, as exemplified by sequences in GenBank.

As used herein, a "mutant" is a mutated protein designed or engineered to alter properties or functions relating to protein stabilization and/or ligand binding.

2. OVERVIEW

The present composition, system, and method (generally, "system") relate to the conditional stabilization of a protein of interest (POI) fused to a single-polypeptide chain, ligand-dependent, stability-affecting protein in vivo. The stability-affecting protein, also referred to as a ligand-binding domain, can be preselected to confer either stability or instability to the entire fusion protein, depending on the presence or absence of the ligand.

A feature of the conditional protein stability system is that the stability-affecting protein is of a "single ligand-single domain" type, which minimizes the number of components in the system. The system is illustrated using two different ligand-binding domains, namely, the FK506-binding protein (FKBP) and dihydrofolate reductase (DHFR), binding domains, in combination with appropriate ligands. Experiments performed in support of the systems are described below, along with embodiments and examples of the system.

3. STABILITY-AFFECTING PROTEIN DERIVED FROM FKBP a. Introduction

Rapamycin and FK506 are commercially available, cell-membrane permeable, FDA-approved immunosuppressive agents, which are ligands of the FK506-binding protein (FKBP12 or FKBP). The FKBP-rapamycin complex binds to the FKBP-rapamycin-binding (FRB) domain of the FKBP-rapamycin-associated protein (FRAP). FRAP is also known as the mammalian target of rapamycin (mTOR), rapamycin and FKBP target 1 (RAFT1), and sometimes FRB. Rapamycin complexed with FKBP binds to and inhibits FRAP/mTOR at its FRB domain, which eventually inhibits/delays cell cycle progression through $G_1$ (see, e.g., Choi, J. et al. (1996) Science 273:239-42 and Vilella-Bach, M. et al. (1999) J. Biol. Chem. 274:4266-72. Fusion polypeptides may be made between a proteins of interest (POI) and either FKBP and/or the FRB domain of FRAP/mTOR. Colocalization of the protein(s) of interest is induced upon addition of rapamycin.

Because rapamycin has inherent biological activity, researchers developed a "bump-hole" strategy (similar to that employed by Shokat and coworkers), wherein rapamycin derivatives with bulky side-chain substituents would bind poorly to the FRB domain of a wild-type/naturally-occurring FRAP/mTOR. Binding was restored by introducing compensatory hole/cavity-forming mutations in the FRB domain. In particular, the bulky side chain of a C20-methallyl-rapamycin derivative (MaRap) is accommodated by a triple-substituted variant of FRB called FRB* (Liberles, S. D. et al. (1997) Proc. Natl. Acad. Sci. U.S.A. 94:7825-7830).

In fusing the FRB and FRB* domains to a kinase GSK-3β it was discovered that the levels of the GSK-3β-FRB* fusion protein were substantially decreased compared to an otherwise identical GSK-3β-FRB fusion protein. The levels of the FRB* fusion protein were rescued (i.e., increased to levels similar to those of the FRB fusion protein) upon the addition of MaRap (Stankunas, K. et al. (2003) Mol. Cell. 12:1615-1624). FRB* appeared to confer conditional instability to multiple different proteins in the absence of MaRap, with stabilization being dependent on the interaction of two proteins (i.e., FKBP and FRB) via a small molecule (MaRap) that is expensive, difficult to synthesize and formulate, and exhibits poor pharmacokinetic properties in vivo.

b. Drug-ON System

The 107-residue FK506 and rapamycin-binding protein (FKBP) was selected for use as a destabilizing domain in a "drug-ON" system. FKBP has been widely studied, often in the context of fusion proteins, and numerous high-affinity ligands for FKBP have been developed (Pollock and Clackson, T. et al. (1998) Proc. Natl. Acad. Sci. U.S.A. 95:10437-10442). In one study, ligands that possess a synthetic "bump" in the FKBP-binding domain were shown to bind more tightly to a mutated FKBP having a cavity formed by the removal of an aromatic side chain (i.e., harboring the substitution, F36V). Such engineered ligands bind preferentially to the mutated FKBP12 compared to the wild-type/naturally-occurring protein by almost three orders of magnitude (Clackson, T. et al. (1998) Proc. Natl. Acad. Sci. U.S.A. 95:10437-10442). Moreover, this family of ligands does not elicit undesired responses when administered to cultured cells or animals, including humans (Iuliucci, J. D. et al. (2001) J. Clin. Pharmacol. 41:870-879).

FIG. 1A illustrates a method for conditionally controlling protein stability using a fusion protein containing a destabilizing domain (DD) derived from FKBP fused in-frame to a protein of interest (POI). In the absence of a stabilizing ligand, the destabilizing domain mediates the degradation of the entire fusion protein. The addition of an appropriate ligand stabilizes the destabilizing domain, greatly reducing degradation of the fusion protein. Using such FKBP polypeptides and ligands, a single unstable ligand-binding domain is able to direct the degradation of a POI, avoiding the need to assemble the FKBP-rapamycin-FRAP/mTOR ternary complex to regulate protein function.

To identify FKBP variants (i.e., mutants) with a high affinity for the synthetic FKBP ligand, SLF* (FIG. 1B) a cell-based screening assay was used to screen a library based on the FKBP F36V gene sequence, which was cloned in-frame with yellow fluorescent protein (YFP) as a reporter protein/protein of interest. In this manner, YFP fluorescence served as an indicator of FKBP stability. The FKBP-YFP fusion protein library (i.e., a library of N-terminal FKBP mutants) was introduced into NIH3T3 fibroblasts using a retroviral expression system. The transfected/transduced cells were subjected to three rounds of sorting using flow cytometry, as illustrated in FIG. 1C. The cells were treated with SLF* (FIG. 1B) in the first round of sorting. The fluorescent cells were collected, cultured in the absence of ligand (second round), and then cultured again in the presence of SLF* (third round), at which time YFP-expressing cells were collected and the genomic DNA was isolated for sequence analysis (Example 7). All sequences analyzed maintained the F36V mutation (not reflected in the nomenclature), along with other frequently recurring amino acid mutations (Table 1).

Five variants (F15S, V24A, H25R, E60G, and L106P) were selected for further analysis. These variant FKBP-derived, ligand-responsive destabilizing domains were separately transduced into NIH3T3 cells and assayed for stability in the presence and absence of a ligand called Shield1, which was a derivative of SLF* in which the carboxylic acid was replaced with a morpholine group at a position unlikely to interfere with FKBP binding (Example 8, FIG. 1B).

Figure 2A:
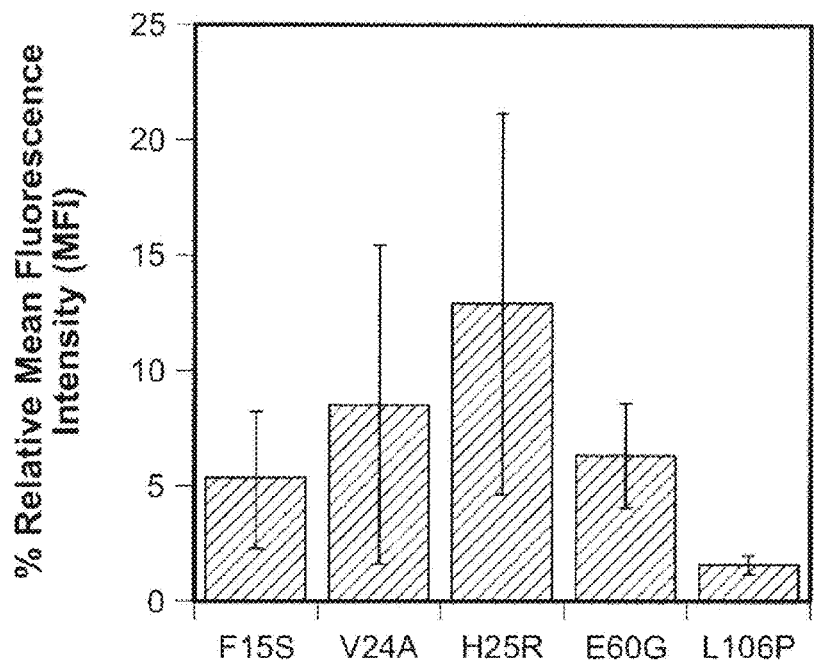
FIGS. 2A-2D are graphs showing the results of experiments to characterize FKBP variants that display Shield1-dependent stability. The data for FIGS. 2A-2D are presented as the average mean fluorescence intensity (MFI)±SEM relative to that of the maximum fluorescence intensity observed for the individual mutant. Experiments were performed in triplicate.
Figure 2B:
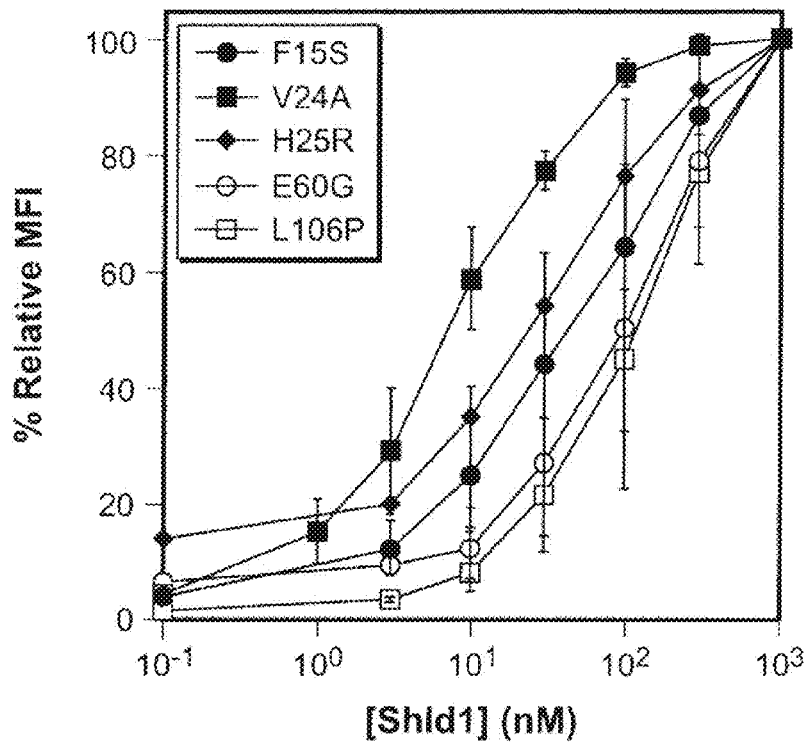
Figure 2C:
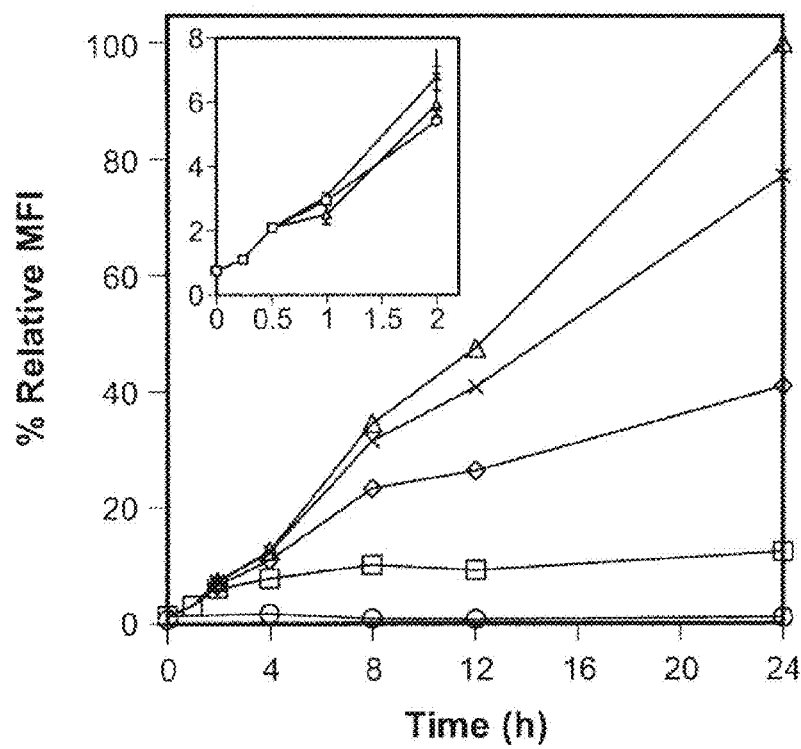

All five variants showed decreased levels of fluorescence with respect to a positive control, indicating that the variants obtained from the library screen were destabilizing (FIG. 2A). The most destabilizing variation, L106P, produced YFP fluorescence at a level of only 1-2% relative to the positive control. All FKBP-derived, ligand-responsive destabilizing domain variants produced increased fluorescence signal when incubated in the presence of Shield1 (FIG. 2B). Variant V24A showed the most efficient rescue (i.e., stabilization by Shield1) with an $EC_{50}$ of about 5 nM. Variant L106P required a higher concentrations of Shield1 to stabilize the YFP fusion protein ($EC_{50}$~100 nM). YFP fluorescence increased at approximately the same rate in all the transfected cells upon addition of Shield1, with maximum fluorescence being achieved at 24 hours and stably maintained for at least an additional 48 hours without further addition of Shield1 (FIG. 2C).

Figure 2D:
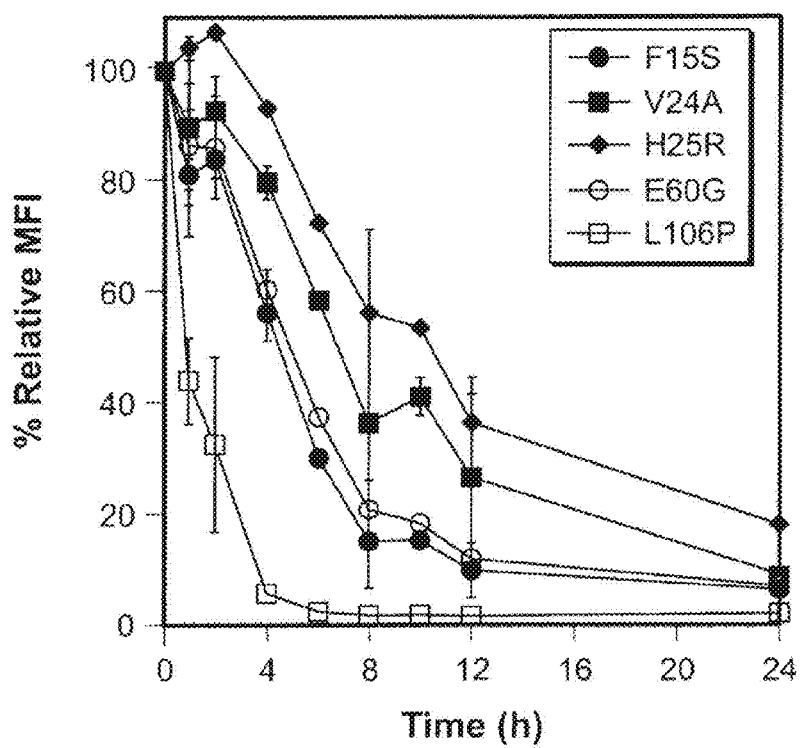
Figure 12:
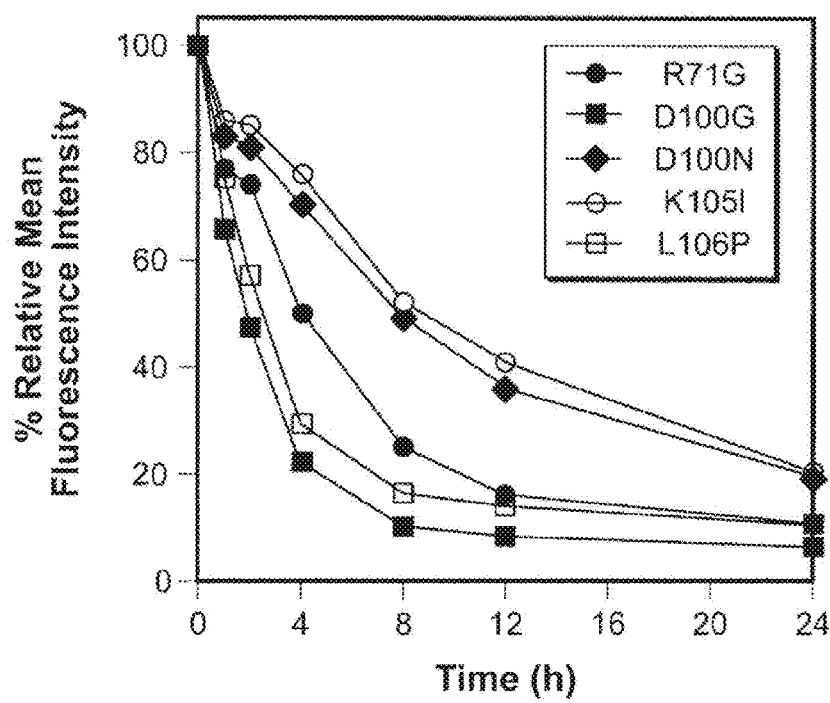
FIG. 12 is a graph showing the kinetics of decay of YFP-FKBP fluorescence upon removal of Shield1. NIH3T3 cells stably expressing YFP-FKBP fusion proteins were treated with 1 µM Shield1 for 24 hours, at which point the cells were washed with media to remove Shield1. The decrease in fluorescence was monitored using flow cytometry. Data are presented as the average mean fluorescence intensity relative to that of the maximum fluorescence intensity observed for the individual mutant.

Upon withdrawal of Shield1, distinct differences in fluorescence decay profiles were observed among the FKBP-derived, destabilizing domain variants (FIG. 2D), revealing a correlation between the rate of degradation and the degree of destabilization. Variant H25R, which is the least destabilizing of this group, showed the slowest rate of degradation, whereas L106P, the most destabilizing of the five, was degraded most quickly, with protein levels becoming negligible within four hours. Similar results were obtained upon withdrawal of Shield1 from C-terminal variant FKBP fusions, as shown in FIG. 12.

Figure 2E:
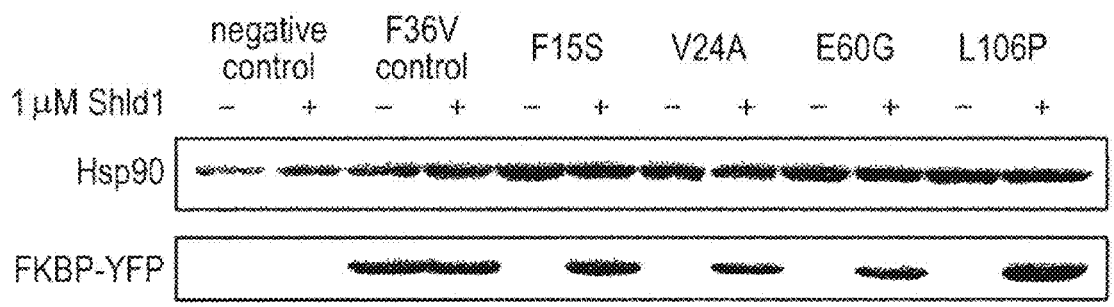
FIGS. 2E-2G show the results of immunoblot analysis to characterize FKBP variants that display Shield1-dependent stability.
Figure 2F:
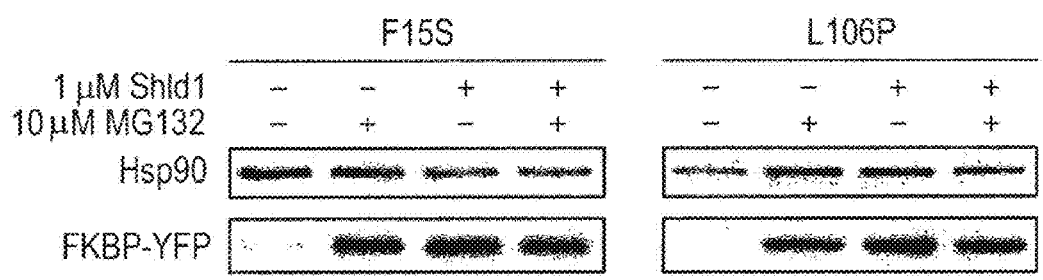
Figure 9:
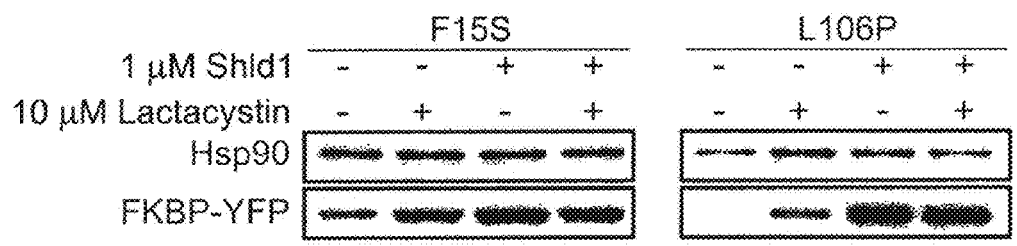
FIG. 9 shows the results of immunoblot analysis demonstrating that degradation of FKBP-YFP fusions is mediated by the proteosome. NIH3T3 cells stably expressing F15S-YFP and L106P-YFP were treated with 1 µM Shield1 for 24 hrs. The cells were then washed and treated with 10 µM lactacystin in the presence and absence of 1 µM Shield1 for 4 hrs. Immunoblot analysis was performed using an anti-YFP antibody.

These results were confirmed by immunoblot analysis using antibodies specific for either FKBP (FIG. 2E) or YFP (data not shown), which were incapable of detection in protein lysates from mock-treated cells, but detectable in detected in protein lysates from Shield1-treated cells (Example 8). Incubation of the transfected cells with MG132 (FIG. 2F) or lactacystin (FIG. 9), which are drugs that inhibit ubiquitin-proteasome-mediated protein degradation, inhibited degradation of the variant FKBP fusion proteins following the withdrawal of Shield1, indicating that degradation was mediated, at least in part, by the proteasome.

Figure 3:
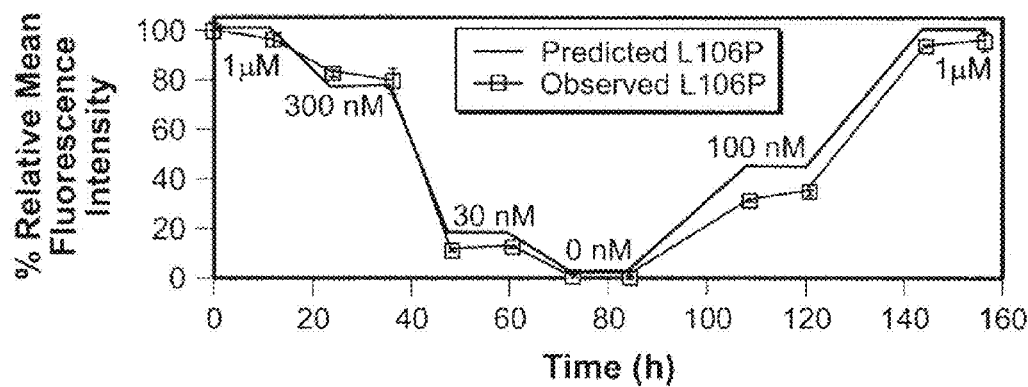
FIG. 3 is a graph showing the reversible nature of small-molecule regulation of intracellular protein levels. A population of NIH3T3 cells stably expressing the L106P-YFP fusion protein was treated with different concentrations of Shield1 over the course of one week, and samples of the population were assayed for fluorescence by flow cytometry at the indicated time points. Predicted fluorescence is based on the dose-response experiment shown in FIG. 2B.
Figure 8:
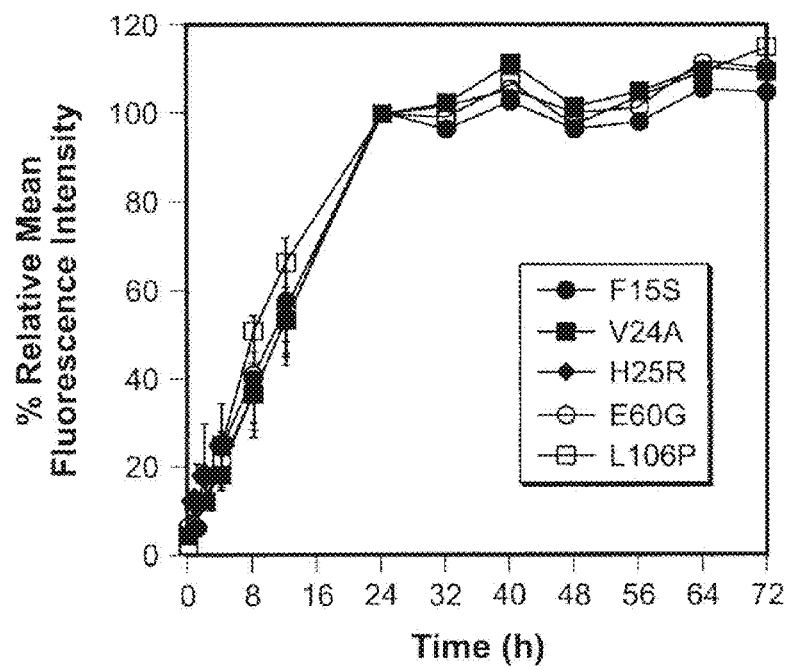
FIG. 8 is a graph showing the kinetics of FKBP-YFP fluorescence in cells upon addition of Shield1. NIH3T3 cells stably expressing the indicated FKBP-YFP fusions were treated with 1 µM Shield1, and increases in fluorescence were monitored over time using flow cytometry. Data are presented as the average mean fluorescence intensity (MFI) ±SEM relative to that of the maximum fluorescence intensity observed for the individual variant. The experiment was performed in triplicate, and MFI was normalized to 100% at 24 hr.

FIG. 3 shows the results of an experiment demonstrating the reversible nature of small-molecule regulation of intracellular protein levels. A population of NIH3T3 cells stably expressing the L106P-YFP fusion protein was treated with different concentrations of Shield1 over the course of one week, and samples of the population were assayed for fluorescence by flow cytometry at the indicated time points. Predicted fluorescence is based on the dose-response experiment shown in FIG. 2B. FIG. 8 shows the kinetics of fluorescence in cells stably expressing one of several FKBP-YFP fusion proteins upon addition of Shield1.

Figure 2G:
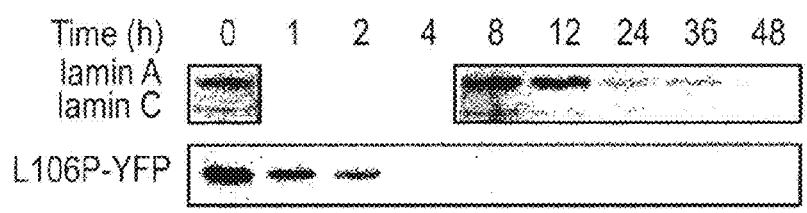
Figure 10:
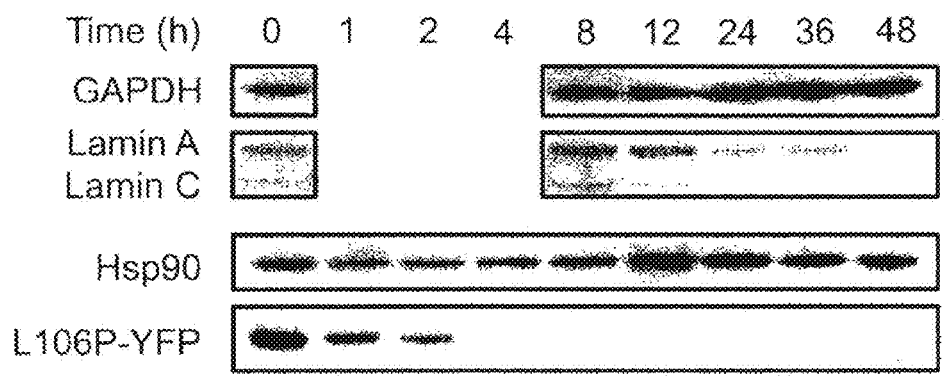
FIG. 10 shows the results of immunoblot analysis comparing the kinetics of destruction-domain-mediated degradation to the kinetics of RNAi-mediated silencing. HeLa cells were transfected with 30 nM siRNA against lamin A/C and monitored over time. The time required for the reduction in levels of lamin A/C was compared to the time required for the degradation of L106P-YFP upon removal of Shield1 from the cells stably expressing the fusion protein.

To compare the present methods with those known in art for regulating gene expression, the rate of degradation of a protein of interest achieved using the FKBP-derived, destabilizing domain variants, was compared to RNAi-mediated silencing of another endogenous gene, Lamin A/C, a nonessential cytoskeletal protein commonly used as a control in RNAi experiments. Previous studies have shown more than 90% reduction in lamin A/C expression in HeLa cells 40 to 45 hours following transfection of the cells with a cognate siRNA duplex (Elbashir, S. M. et al. (2001) *Nature* 411: 494-498). In line with published results, HeLa cells transfected with siRNA against lamin A/C showed a decrease in lamin A/C levels after 24 hours, with a significant reduction in lamin A/C observed by 48 hours (FIGS. 2G and 10). In contrast, cells stably expressing L106P-YFP show nearly complete degradation of the fusion within 4 hours of removal of Shield1. These results demonstrate that fusion of a destabilizing domain to a protein of interest dramatically reduces its stability in cultured cells, causing the protein of interest to be quickly degraded upon removal of the stabilizing ligand (Example 8).

Further experiments demonstrated that NIH3T3 cells stably expressing the L106P-YFP variant produced YFP fluorescence in a dosage-dependent manner with respect to the amount of ligand present (Example 9). The results obtained using N-terminal destabilizing domains are shown in FIG. 2B. C-terminal destabilizing domains responded to Shield1 in a dose-dependent manner comparable to N-terminal destabilizing domains, with $EC_{50}$ values ranging from 10 nM to 100 nM (Example 10, FIG. 11, and Table 2). Ligand-dependent protein stability was also observed in NIH3T3, HEK 293T, HeLa, and COS-1 cells that were transfected with the FKBP-derived fusion proteins (Example 11, Table 3), demonstrating that ligand-dependent stability is not restricted to one cell type.

Figure 4A:
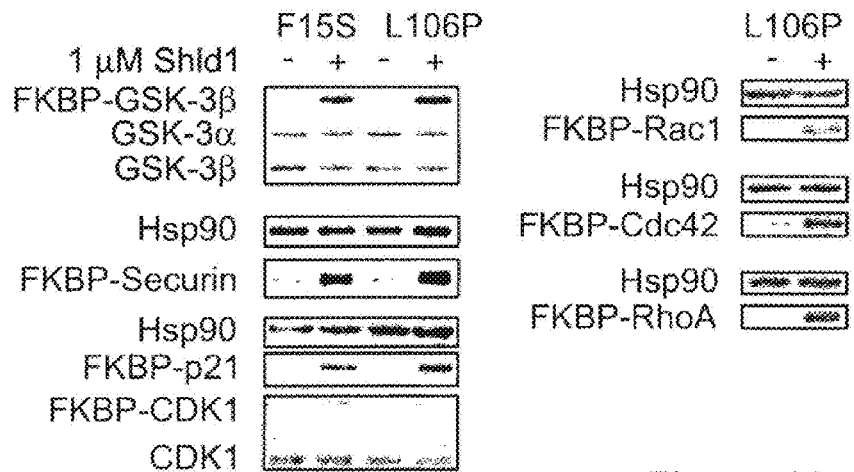
FIGS. 4A and 4B show the results of immunoblot analysis demonstrating that the FKBP destabilizing domain confers Shield1-dependent stability to a variety of different proteins.

FKBP variants were efficient in destabilizing proteins other than YFP, e.g., the kinases GSK-3β and CDK1, the cell cycle regulatory proteins securin and p21, and three small GTPases, Rac1, RhoA and Cdc42 (FIG. 4A). All these N-terminal fusion proteins demonstrated Shield1-dependent stability, with the absence of Shield1 resulting in the degradation in a Shield1-dependent manner (Example 12).

Figure 5:
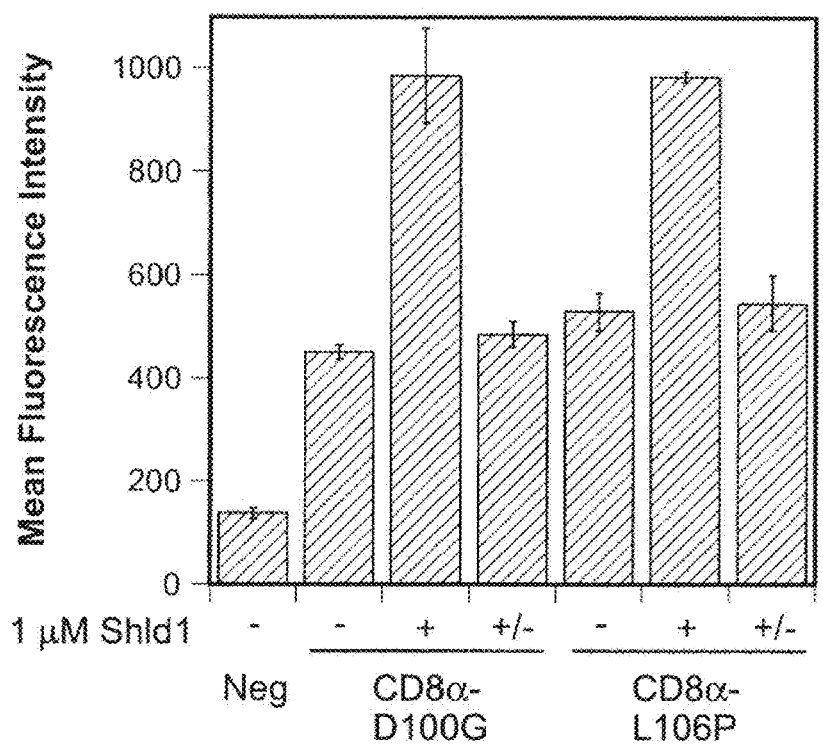
FIG. 5 is a graph showing that the destabilizing domain confers Shield1-dependent stability to a transmembrane protein. FKBP variants DING and L106P were fused to the C-terminus of CD8α. NIH3T3 cells stably expressing the fusion proteins were divided into three pools (groups). The first group (−) was mock-treated, the second group (+) was treated with 1 µM Shield1 for 24 hrs, and the third group (+/−) was treated with 1 µM Shield1 for 24 hrs, and then washed with media and cultured for 24 hr in the absence of Shield1. Live cells were then probed with a FITC-conjugated anti-CD8α antibody and assayed by flow cytometry. Data are presented as the average mean fluorescence intensity±SEM from an experiment performed in triplicate.

FKBP variants were also efficient in destabilizing proteins other than YFP, e.g., the transcription factor CREB, or the small GTPases Arf6 or Arf7, when the FKBP mutant is fused at the C-terminus of the protein of interest (FIG. 4A). All these C-terminal fusion proteins demonstrated Shield1-dependent stability, with the absence of Shield1 resulting in the degradation in a Shield1-dependent manner (Example 12). As shown in FIG. 5, the destabilizing FKBP variants D100G (SEQ ID NO: 7) and L106P (SEQ ID NO: 6) also conferred Shield1-dependent stability to a transmembrane protein, CD8a, when fused at the C-terminus of the transmembrane protein.

Moreover, cell morphology could be manipulated by the presence or absence of Shield1 (Example 13). Shield1-treated cells displayed the predicted morphologies, a, expression of RhoA induced the formation of stress fibers, expression of Cdc42 resulted in filopodia formation, and expression of Arf7 induced the shrunken cell phenotype (Heo, W. D. and Meyer, T. (2003) *Cell* 113:315-328), while mock-treatment with Shield1 produced cells with fibroblast-like morphologies. These GTPase-dependent morphology changes were reversible, as treatment with Shield1 followed by removal of Shield1 also produced cells with fibroblast-like morphologies. The penetrance of the observed phenotype was high, with a large percentage of cells (>90%) exposed to a given experimental condition displaying the predicted behavior (data not shown).

Figure 13:
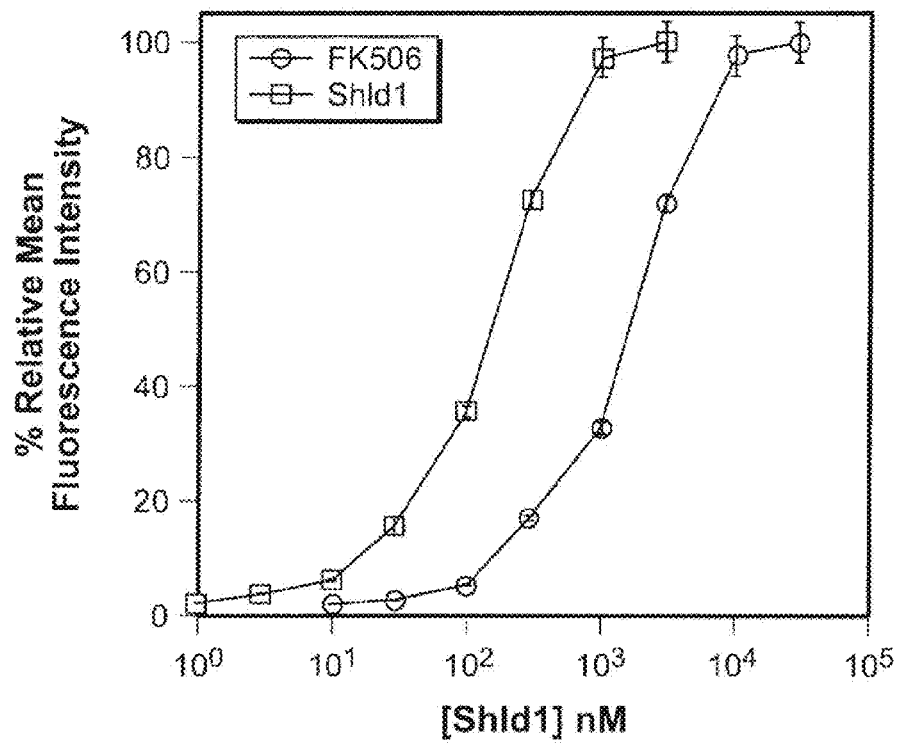
FIG. 13 is a graph showing that FKBP-YFP fusion proteins are stabilized by multiple FKBP ligands. NIH3T3 cells stably expressing the L106P-YFP fusion were treated with three-fold dilutions of FK506 (30 µM to 10 nM) or Shield1 (3 µM to 0.1 nM) and fluorescence was monitored by flow cytometry. Data are presented as the average mean fluorescence intensity±SEM relative to that of the maximum fluorescence intensity observed for the L106P-YFP mutant. Experiments were performed in triplicate.

The FKBP-derived destabilizing domains can be stabilized using Shield1 as well as the commercially available ligand, FK506 (FIG. 13).

c. Drug-OFF System

The above-described FKBP-derived conditional protein stability system uses a variant of FKBP to stabilize a POI in the presence of an appropriate ligand, and destabilize the POI in the absence of the ligand, representing a "drug-ON" system. In a related embodiment of the system, a variant FKBP polypeptide sequence was used to destabilize a POI in the presence of an appropriate ligand, and stabilize the POI in the absence of the ligand, representing a "drug-OFF" system.

Figure 6A:
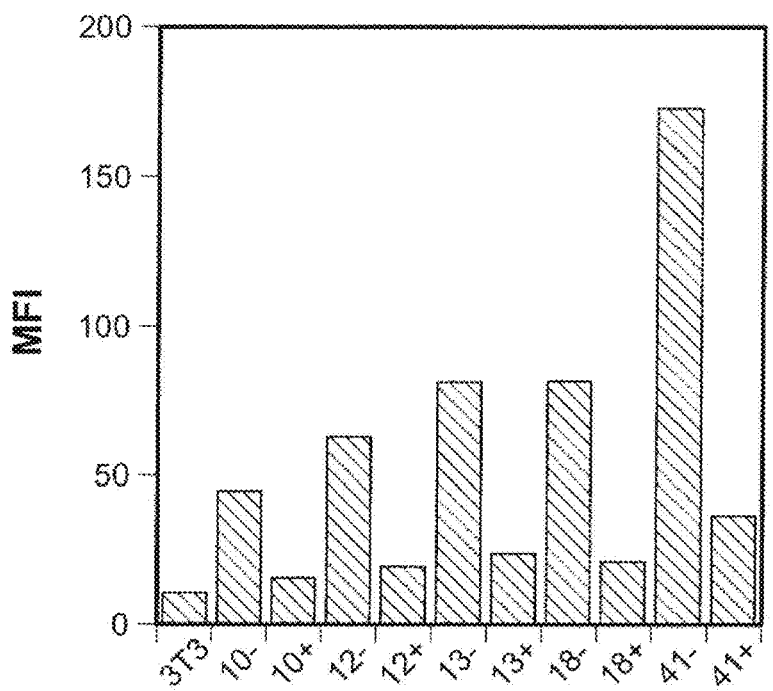
FIG. 6A shows the results of an experiment using a "drug-OFF" system, in which a FKBP protein attached to a diversity element sequence was fused to YFP. YFP fluorescence could be detected by FACS analysis in the absence of the ligand (Shield1) but was almost undetectable in the presence of the ligand (n=5 clones).

Variant FKBP polypeptide sequences having the desired properties were identified by preparing a library of sequences encoding FKBP (F36V) with a short, 20-amino acid diversity element (i.e., population of sequences encoding different amino acids) fused at the C-terminus of FKBP. The FKBP-diversity element sequences were fused to the C-terminus of YFP, as before, and the sequences encoding the YFP-FKBP-diversity element were introduced into NIH3T3 cells for screening. Five different clones were identified in which YFP could be detected by FACS analysis in the absence of the ligand (Shield1) but was nearly undetectable in the presence of the ligand (i.e., a 5 to 6-fold decrease in the presence of ligand; FIG. 6A). The sequence encoding the FKBP-diversity element variants were recovered from the cells and sequenced, revealing that all five clones encoded the same diversity element sequence, namely TRGVEEVAEGVVLLRRRGN (SEQ ID NO: 18). Thus, a FKBP polypeptide fused to the selected diversity element functioned as a stabilizing domain in the absence of ligand, rather than a destabilizing domain, as is characteristic of, e.g., the F36V/L106P FKBP mutant and other mutants.

The "drug-OFF" system offers some advantages over the "drug-ON" system. In particular, the "drug-OFF" system requires the presence of the ligand only to destabilize the POI. Thus, where the POI is essential for viability, the absence of the ligand allows the protein to function normally. In contrast, in a "drug-ON" system, the ligand must be present at all times, except where the effect of removing the POI is being studied. Since the cost of maintaining cells or animals in the presence of ligand over a prolonged period of time can be considerable, the "drug-OFF" system can be more economical.

d. Use of the System in Other Eukaryotic Organisms

While the FKBP system was first characterized in mammalian cells, further experiments have demonstrated that the system works in eukaryote parasites, particularly *Toxoplasma* and *Plasmodium*.

Figure 6B:
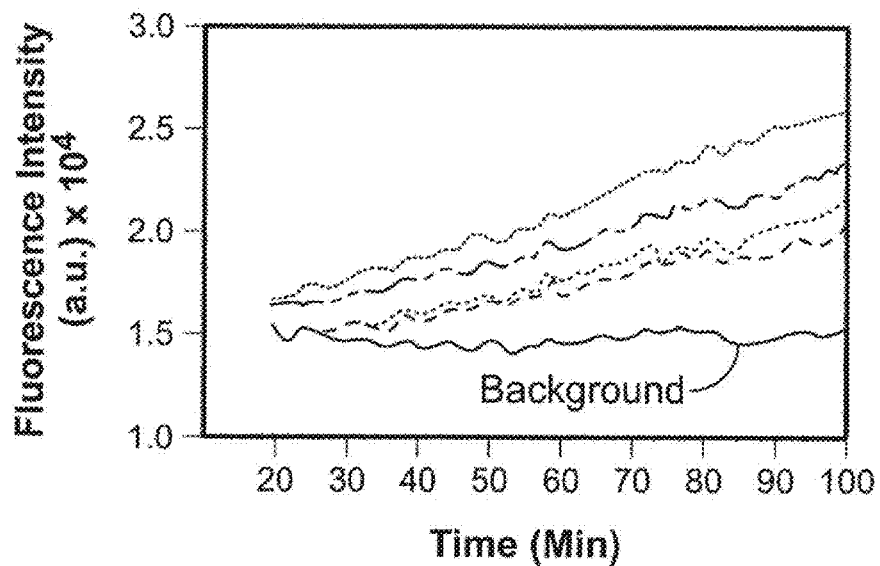
FIGS. 6B and 6C shows the results of an experiment performed in *Toxoplasma*. The fluorescence of parasitophorous vacuoles in infected cells was monitored by time lapse microscopy following addition (FIG. 6B) or removal of ligand (FIG. 6C). Background fluorescence is indicated.
Figure 6C:
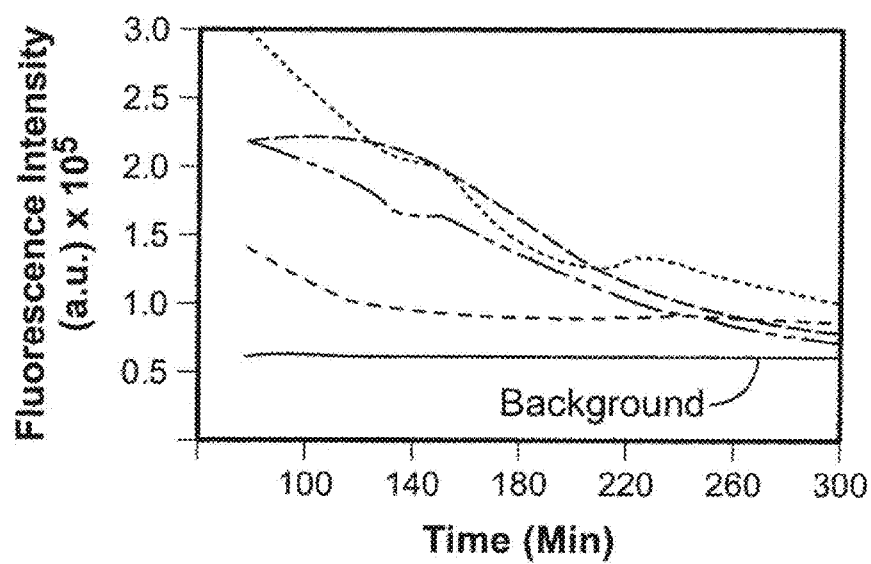

FIGS. 6B and 6C shows the results of experiments performed in a *Toxoplasma gondii* system, in which an FKBP-derived stability-affecting domain was fused to the N-terminus of YFP. Nucleotides expressing the fusion the fusion protein were introduced into *T. gondii* parasites, which were then used to infect HFF cells. The parasitophorous vacuoles in the infected cells were monitored by time lapse fluorescence microscopy following the addition of ligand (Shield1; FIG. 6B) or following the removal of ligand (FIG. 6C). The indicated control line corresponds to background fluorescence, while each of the other lines in the graphs correspond to individual infected cells. The results show that the levels of YFP increase in the presence of ligand and decrease in the absence of ligand, demonstrating that the conditional protein stability system is effective in *Toxoplasma*.

Figure 6D:
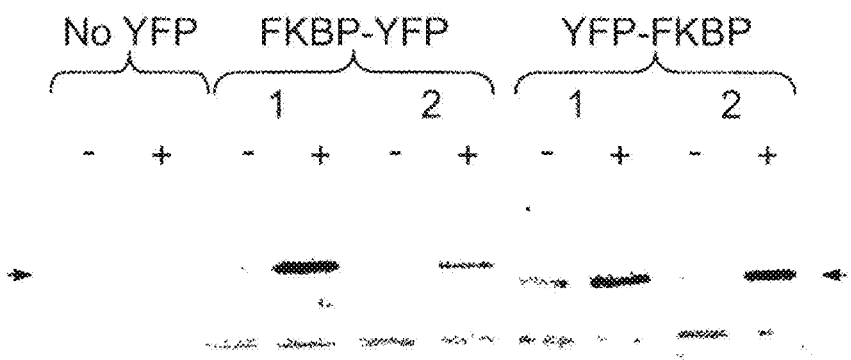
FIGS. 6D and 6E shows the results of an experiment performed in a *Plasmodium*. An antibody to YFP protein was used to detect fusion proteins in transfected cells, which are greatly increased in the presence of ligand.
Figure 6E:
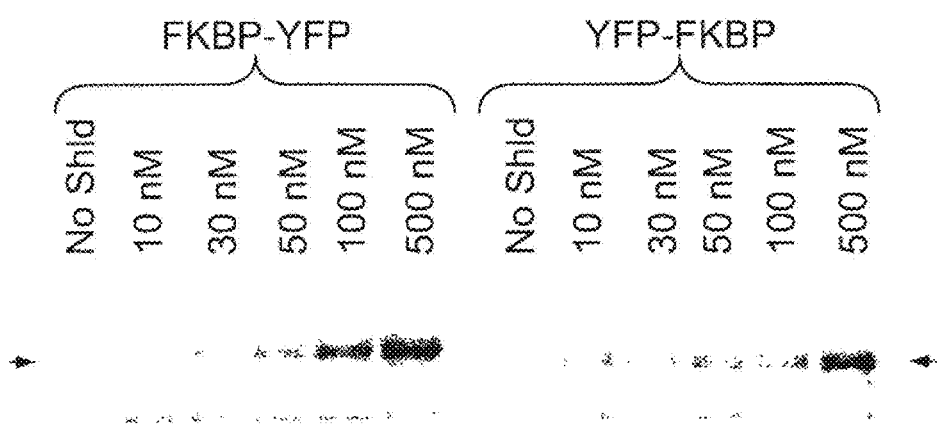

In another illustration of use of the system in eukaryotic parasites, FIGS. 6D and 6E shows the results of an experiment performed in a *Plasmodium falciparum*. The immunoblot shows the levels of YFP fusion protein in transfected cells, which are greatly increased in the presence of ligand. In a related experiment, fusion proteins were made with falcipain-2, a cysteine protease. Knocking out the falcipain-2 gene causes vacuole swelling resulting from the decreased ability of the organisms to degrade hemoglobin. Fusion of falcipain-2 to the F36V/L106P FKBP mutant produced a conditional falcipain stabilization system. More than 5-times as many organisms demonstrated the swollen vacuole phenotype in the presence of ligand (Shield1), compared to the absence of ligand.

e. Use of the System In Vivo to Control the Stability of Tumor Proteins

HCT116 cancer cells were transfected with nucleic acids encoding the reporter gene luciferase fused to an FKBP-derived stability-affecting protein (F36V/L106P) mutant. Stable transformants were selected and used to challenge SCID mice. SCID were challenged with tumor cells expressing luciferase fused to-derived FKBP F36V/L106P-derived stability-affecting protein and treated with the indicated amounts of ligand (Shield1), or untreated (control), and bioluminescent signals were imaged over time as described (Lin, A. H., et al. (2005) *J. Immunol.* 175:547-54; Luo, J., et al. (2006) *Proc. Nat'l. Acad. Sci. USA* 103:18326-31; n=4-10 mice per treatment group).

Figure 7A:
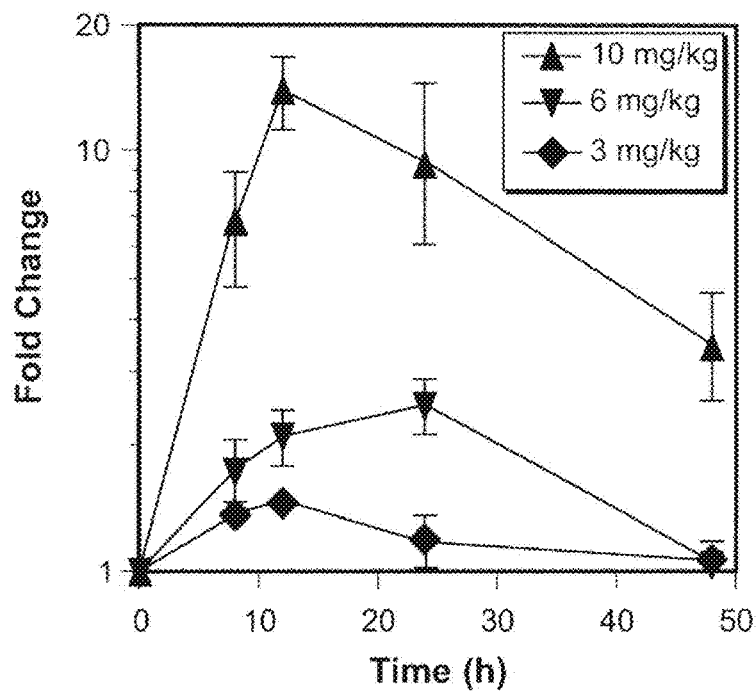
FIGS. 7A and 7B are graphs showing the results of an experiment in which SCID mice were challenged with tumor cells genetically manipulated to express luciferase fused to a stability-affecting protein.
Figure 7B:
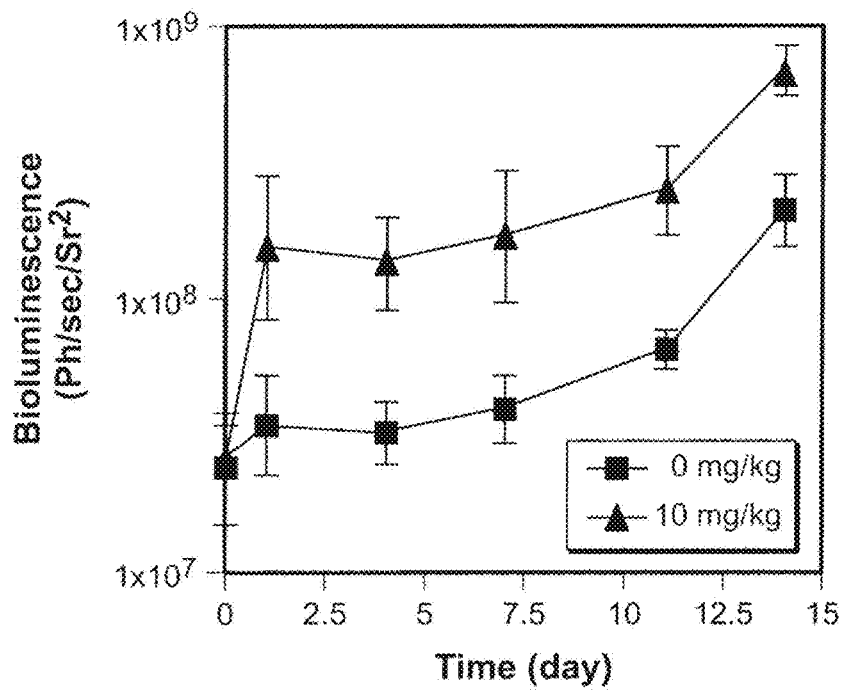

The graph in FIG. 7A shows that the amount of luminescence is dependent on ligand dose, and that luminescence peaks at about 10 hours following a single injection of ligand. The graph shown in FIG. 7B shows that repeated administration of the ligand (10 mg/kg Shield1 every 48 hours) results in continued luciferase stabilization. These results demonstrate that the conditional protein stabilization systems work in vivo, where the ligand is delivered to cells via the blood stream of an animal.

Figure 21A:
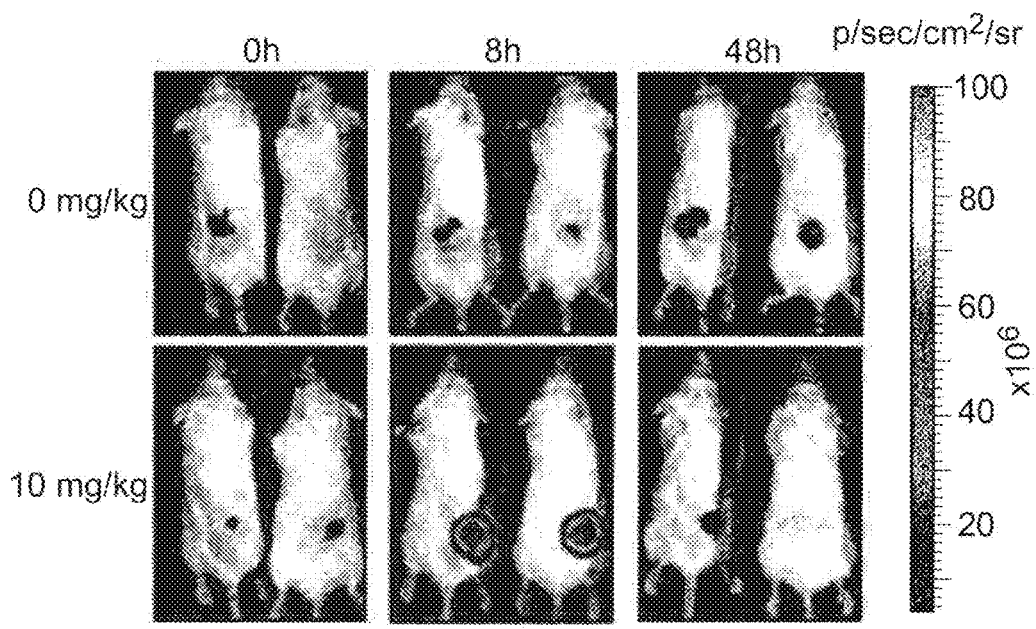
FIGS. 21A-21D show the results of experiments showing conditional regulation of protein stability in vivo. SCID mice bearing HCT116 L106P-tsLuc xenografts (50-100 mm$^3$) were either untreated (top row) or treated i.p. with Shield1 (10 mg/kg, bottom row) and bioluminescent signals were imaged over time (FIG. 21A).
Figure 21B:
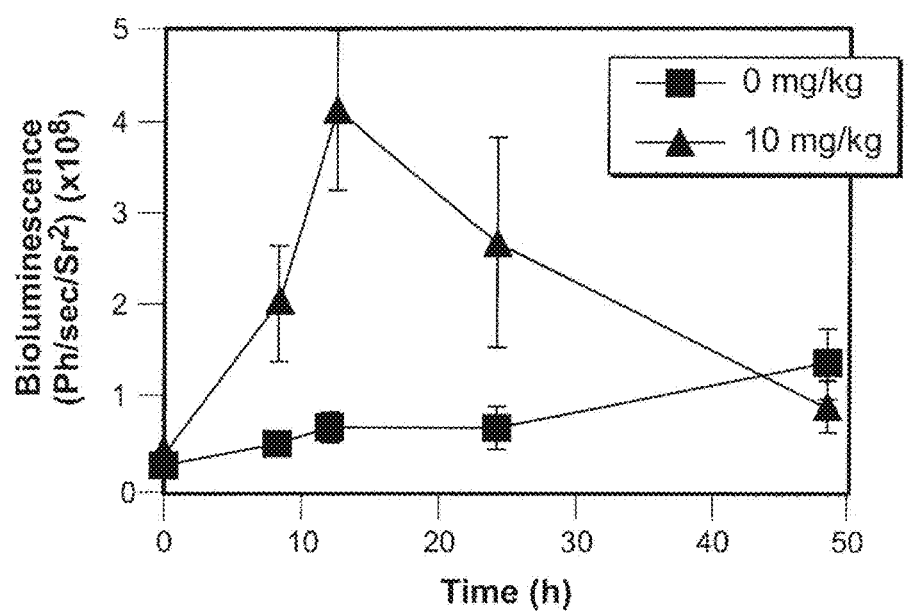
Figure 21C:
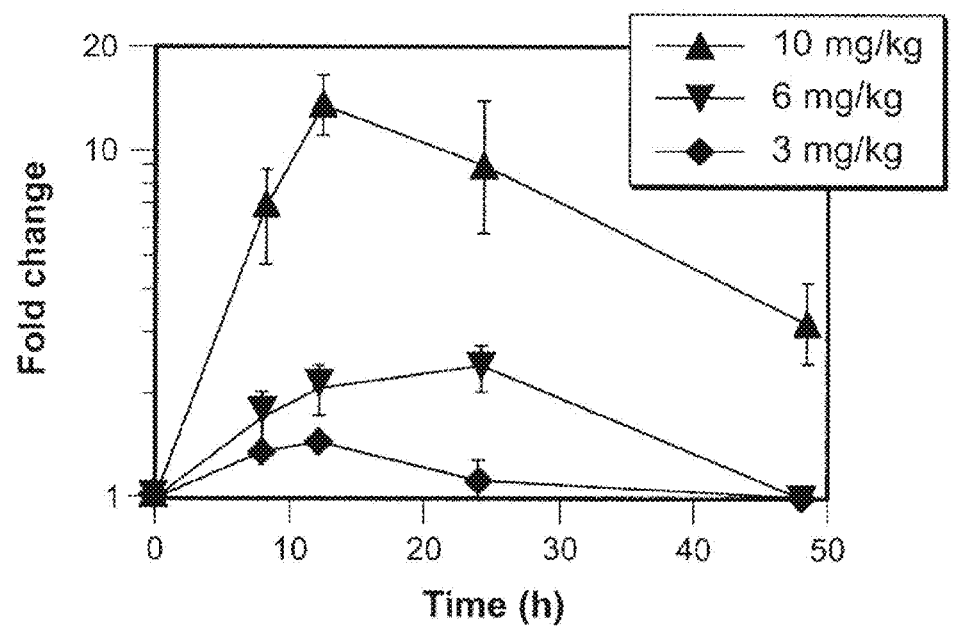

In a related experiment, polynucleotide sequences encoding the FKBP L106P stability-affecting protein were fused to polynucleotides corresponding to the N-terminus of a thermostable luciferase to obtain the chimeric gene L106P-tsLuc, which was stably integrated into HCT116 colon cancer cells. HCT116 cells expressing the resulting fusion protein were tested for conditional regulation of luciferase activity in vitro using the ligand, Shield1 (not shown) and then implanted as xenografts onto immunodeficient mice. Shield1 (or vehicle only as a control) was delivered intraperitoneally (ip) at a dose of 10 mg/kg and luciferase activity was measured by in vivo bioluminescence imaging as shown in FIG. 21A. Maximum expression levels were observed 12 hours following treatment with Shield1, with bioluminescent signals returned to background within 48 hours, suggesting that Shield1 is delivered systemically and is maintained at sufficient levels within target cells to stabilize the fusion protein for a significant period of time before being cleared. Quantification of the data shown in FIG. 21B demonstrated an approximate 10-fold increase in signal in the presence of Shield1 compared to the absence of Shield 1, demonstrating conditional control of protein stability via the stability-affecting protein. Mice bearing HCT116 L106P-tsLuc xenografts and treated with increasing doses of Shield1 (i.e., 3, 6, or 10 mg/kg) showed increasing bioluminescence levels (FIG. 21C), demonstrating dose responsiveness.

Figure 21D:
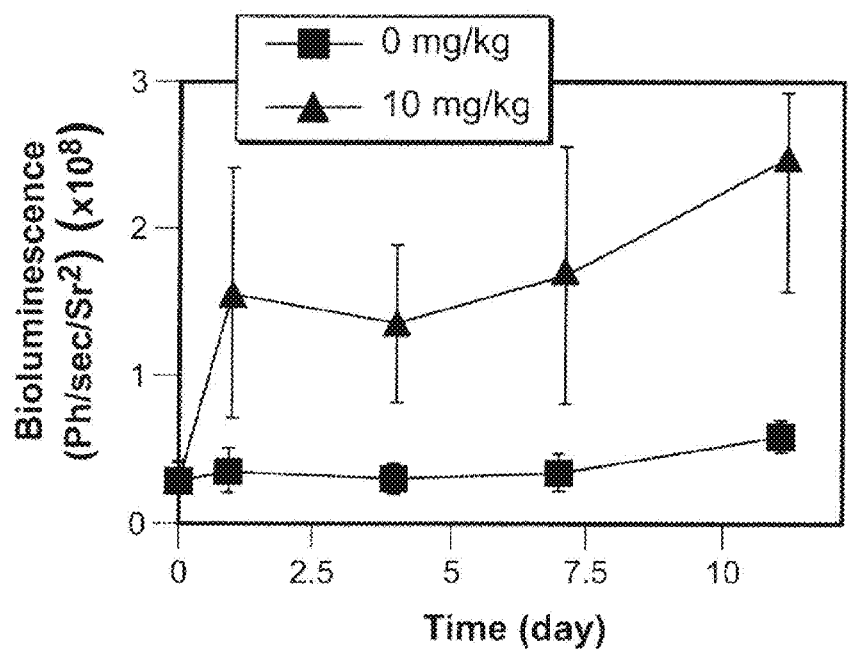
Figure 22A:
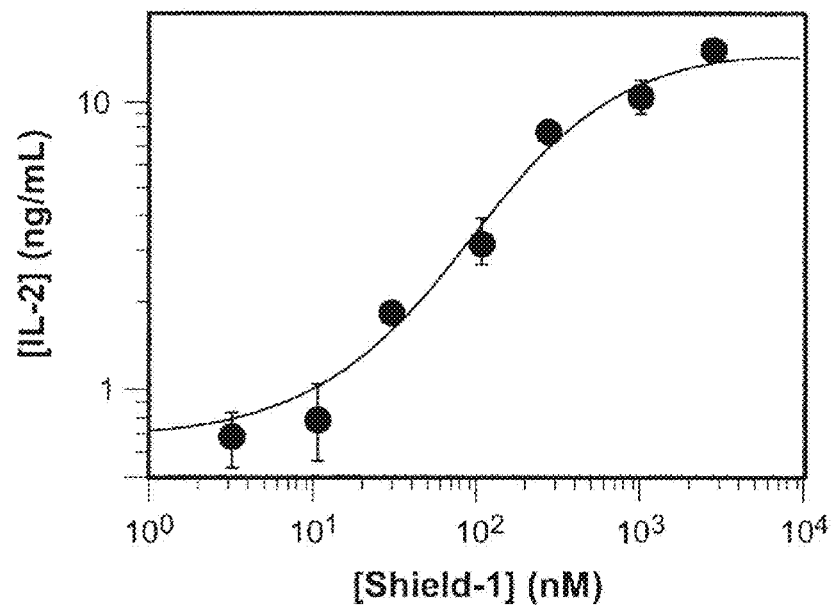
FIGS. 22A-22D show graphs relating to the conditional stabilization of a secreted immunomodulatory protein leads.
Figure 22B:
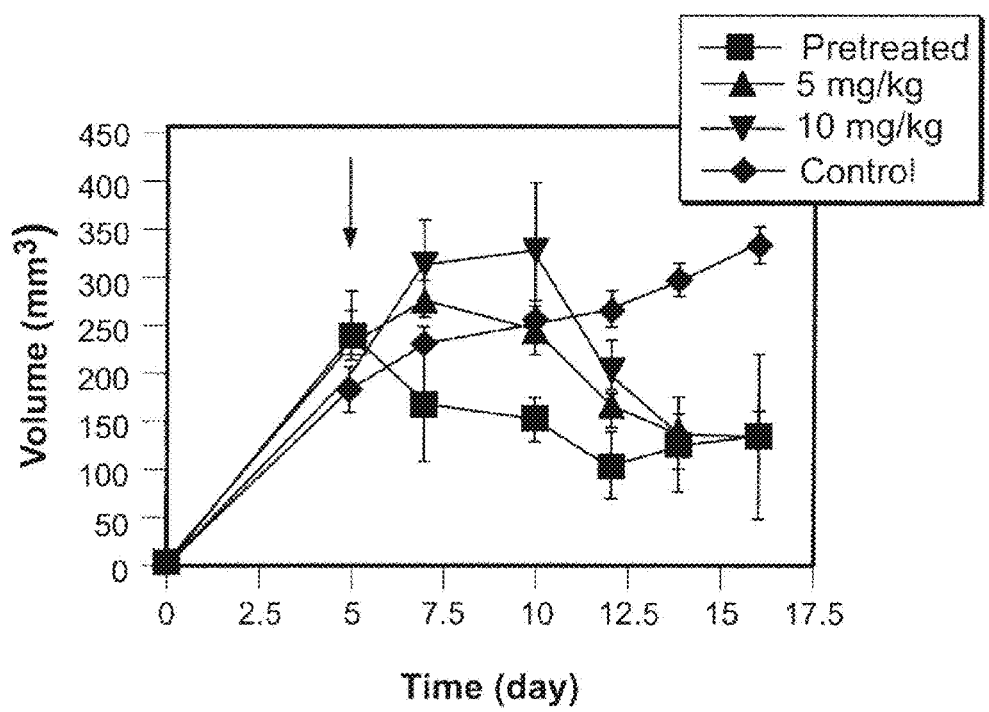
Figure 22C:
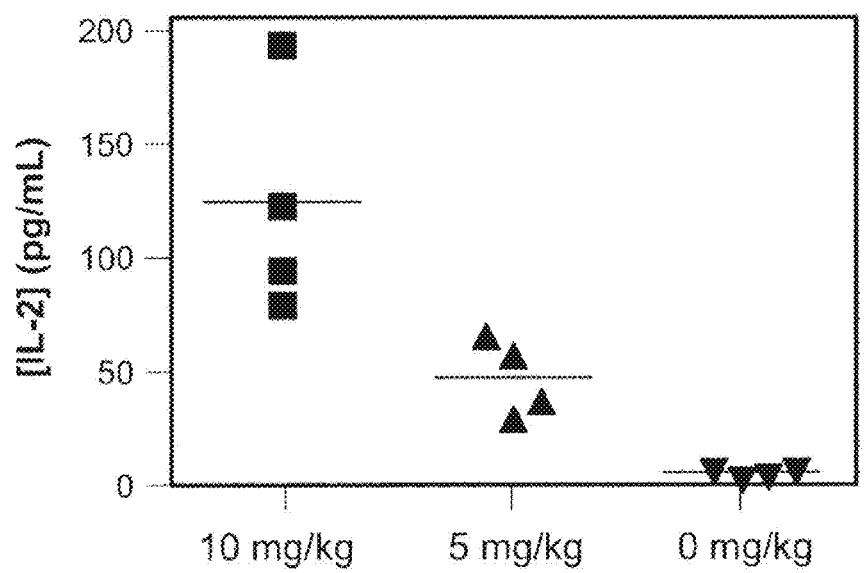
Figure 22D:
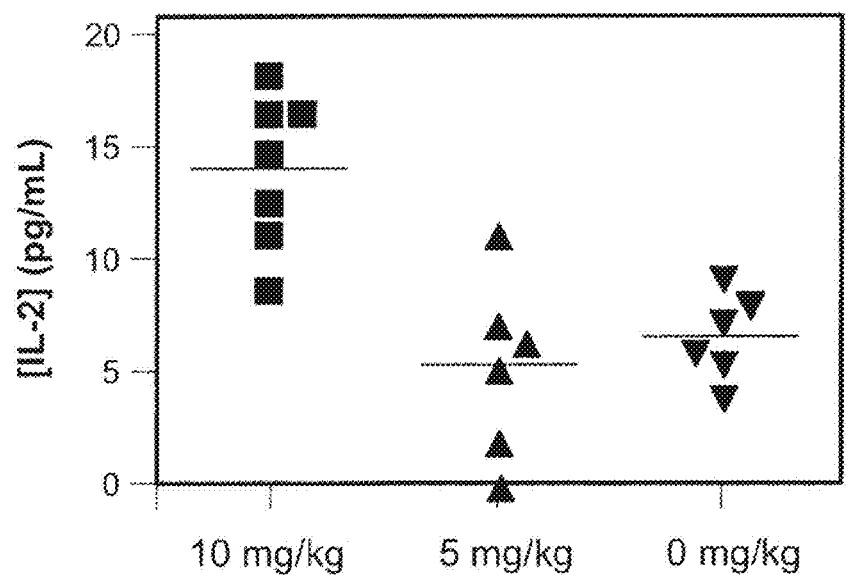
Figure 23A:
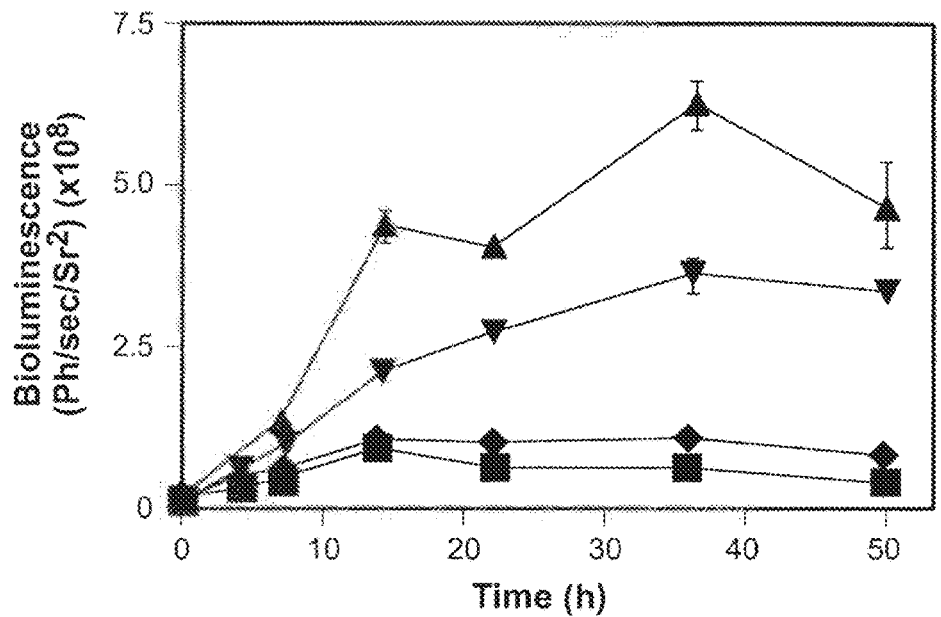
FIGS. 23A-23C relate to the systemic, targeted-delivery of a conditionally stabilized protein.
Figure 23C:
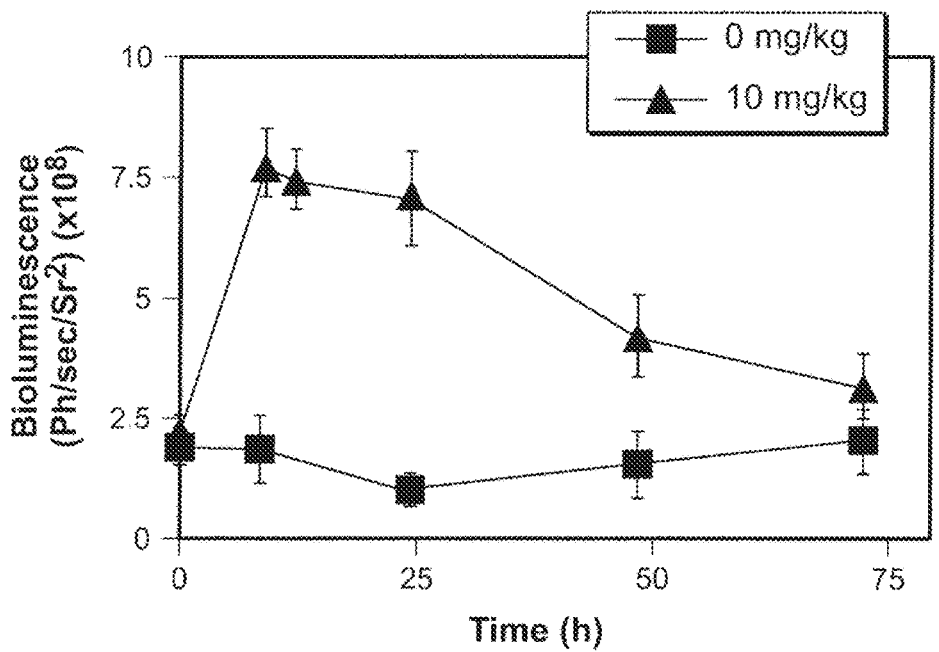
Figure 23B:
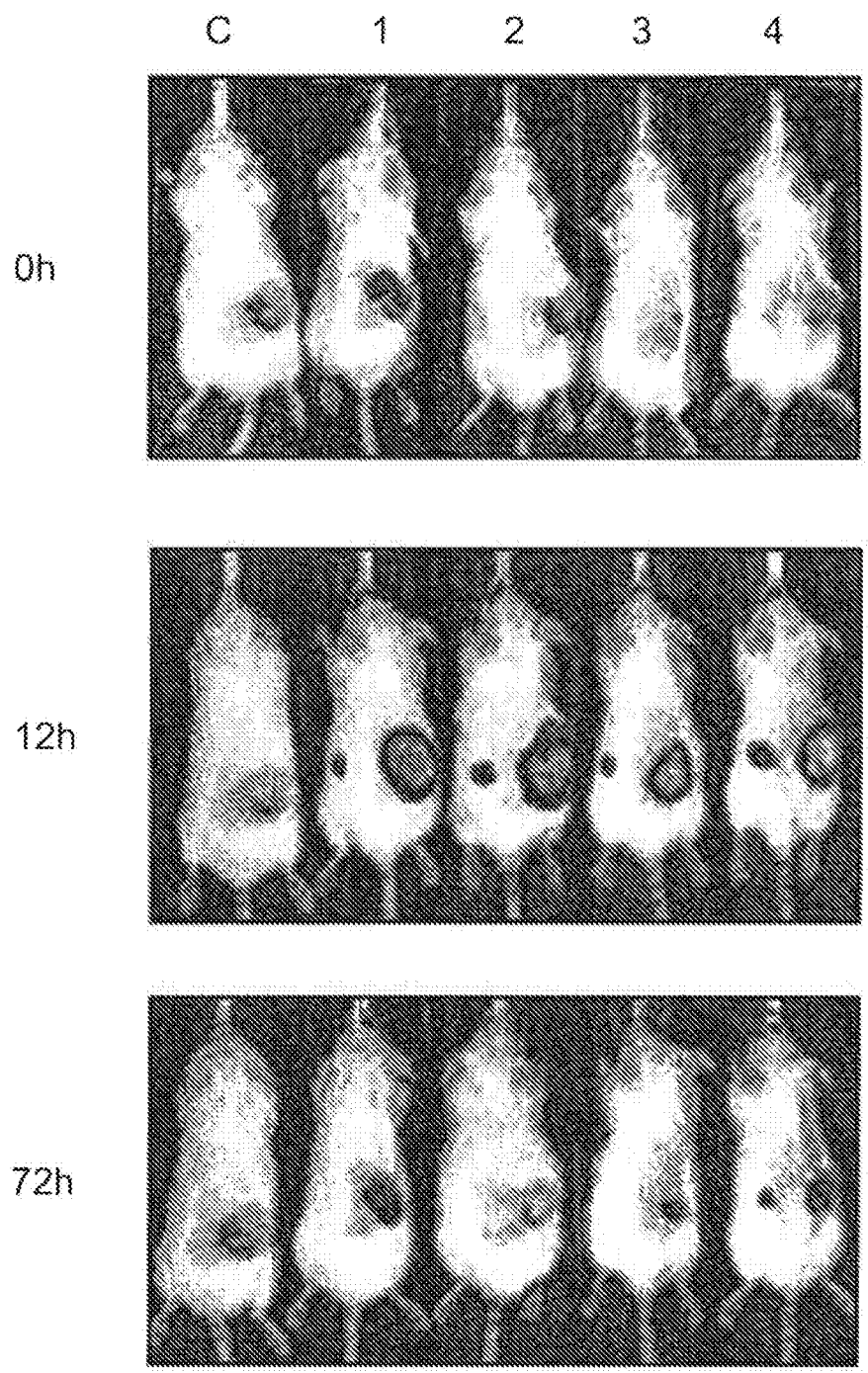
Figure 24:
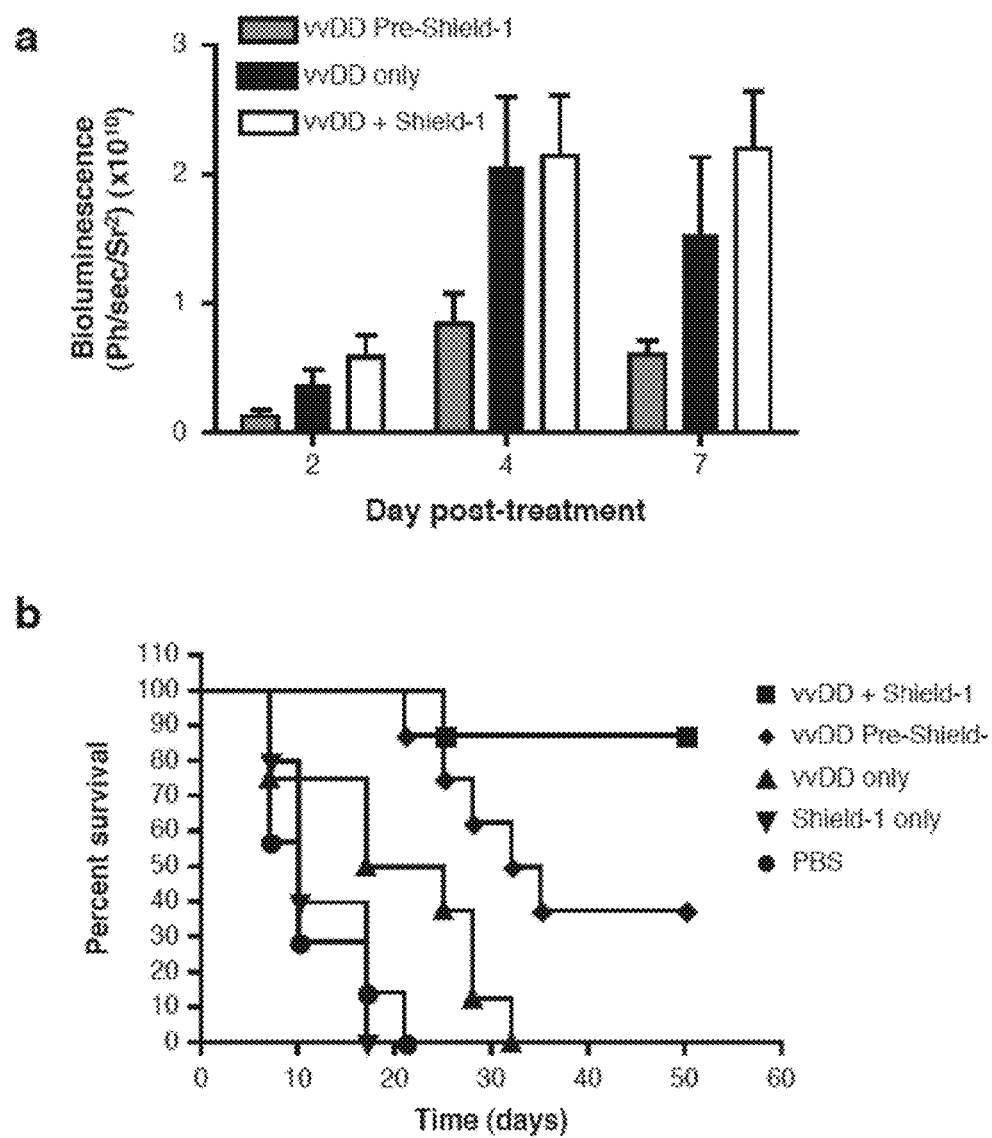
FIGS. 24A and 24B show the antitumor effects of conditional stabilization of tumor necrosis factor delivered via a vvDD virus. Viral load within the tumor was assayed by measuring constitutive viral gene expression (bioluminescence) for each group at the indicated time points after vvDD treatment.

Animals treated with Shield1 (10 mg/kg) periodically, i.e., once every 48 hours, were also found to maintain increased bioluminescence levels over the course of several weeks compared to animals not treated with Shield1 (FIG. 21D), suggesting that a periodic low-dose treatment regimen with Shield1 is sufficient to control protein stability in vivo.

Periodic administration of ligand is advantageous in terms of reducing reagent cost and reducing the handling of animals; however, the administration of Shield1 did not appear to affect feeding behavior, body weight, or overall activity (not shown), indicating that the ligand is substantially non-toxic to animals even when delivered frequently. These observations are consistent with microarray analysis of mRNA levels in cells treated with Shield1, which demonstrated no appreciable cellular response to treatment.

f. Use of the System In Vivo to Control Tumor Burden

The experiments described above relate to the conditional stability of a reporter protein in tumors cells. Further experiments demonstrated that conditional stabilization of a protein could actually affect tumor burden.

Interleukin-2 (IL-2) is a cytokine that is instrumental in immune response, inducing the differentiation and proliferation of a variety of lymphocyte populations (Gaffen, S. L. and Liu, K. D. (2004) Cytokine 28:109-23). Recombinant IL-2 is approved for clinical treatment of renal cancers and is used in a variety of other cancer therapies.

Polynucleotides encoding the L106P stability-affecting protein were inserted between polynucleotides of the IL-2 gene that encode the signal peptide and the remainder of the IL-2 protein to produce the chimeric gene, L-L106P-IL-2, which was stably introduced into HCT116 cells. The levels of IL-2 secreted by the transfected HCT116 cells increased in a dose-dependent manner depending on the concentration of Shield1 in the media, with a dynamic range of approximately 25-fold (FIG. 22A).

Cells harboring the L-L106P-IL-2 chimeric gene, were implanted as a xenog raft onto mice (as above), and the ability of the cells to establish tumors and proliferate in the presence and absence of ligand (Shield1) was monitored (FIG. 22B). Under these conditions, the HCT116 L-L106P-IL-2 cells secreted stabilized IL-2, in a "drug-ON" manner.

Tumors in the untreated control animals continued to increase in size over the course of the experiment. Tumors failed to establish in mice that received HCT116 L-L106P-IL-2 cells and had been pretreated with Shield1 and continued to be treated with Shield1 (10 mg/kg) every 48 hours following implantation of the xenograft. Mice that were not pretreated with Shield1 prior to tumor implantation but were treated with Shield1 (i.p. at either 5 or 10 mg/kg every 48 hours) five days following tumor establishment showed tumor regression, with the size of the tumor eventually being reduced to that observed in the pretreated animals. By day 16, all Shield1-treated groups displayed significantly reduced tumor burden relative to untreated animals ($p<0.05$).

These results demonstrated that stabilization of IL-2 following implantation resulted in tumor regression, whereas stabilization of IL-2 prior to and following implantation prevented tumor establishment.

Analysis of IL-2 levels within the tumors of treated and untreated mice confirmed dose-dependent production of IL-2 at the tumor site in mice treated at 5 or 10 mg/kg Shield1 (FIG. 22C; $p=0.032$). In contrast, analysis of serum IL-2 levels showed significantly elevated levels in the 10 mg/kg Shield1 group relative to tumor-bearing mice not receiving Shield1 ($p=0.0004$), whereas IL-2 serum levels in mice treated with only 5 mg/kg Shield1 were similar to those in control group (FIG. 22D). These observations suggested that Shield1 addition produced a tunable, dose-dependent secretion of a cytokine in vivo, and that altering the dose of Shield1 can achieve different biological effects. A dose of 5 mg/kg Shield1 was sufficient to produce the same robust anti-tumor response as 10 mg/kg Shield1, while avoiding the increase in IL-2 serum levels associated with the higher ligand dose.

g. Viral Delivery of a Conditional Stabilization System to Control Tumor Burden

A viral gene delivery system for the systemic treatment of cancer based on a replication-selective (oncolytic) strain of vaccinia virus (hereafter vvDD) has been described (Thorne, S. H. et al. (2006) *Science* 311:1780-84). The deletion of the vira thymidine kinase genes and growth factor genes restrict the replication of this virus to cancer cells (McCart, J. A. et al. (2001) *Cancer Res.* 61:8751-7). Intravenous delivery of vvDD results in the initial infection of tumor and other cells, followed by rapid replication and spread of the virus in tumor cells and clearance in other cells. vvDD can deliver transgenes to tumor cells following systemic delivery, allowing the system to be used to study conditionally stabilized proteins.

Preliminary experiments established that infection of cultured cells with vvDD did not affect the kinetics or dynamic range of L106P-regulated protein stability, and that the ligand, Shield1, did not affect the replication of the virus (data not shown). Strains of vvDD were then constructed to express either L106P-tsLuc or L106P-ref fluorescent protein (RFP) fusion proteins and ligand (Shield1)-dependent protein activity (i.a, fluorescence) was measured in cultured cells (FIG. 23A). The results of ligand (Shield1)-dependent stabilization of vvDD-delivered L106P-tsLuc in mice are shown in FIGS. 23B and 23C. Best results were obtained by allowing 72 hours for viral infection to establish within the tumor cells and to be cleared from most other cells in the mice before beginning Shield1 treatment to selectively stabilize the protein of interest in the tumor cells.

To test the ability of a virally-delivered condition protein stabilization system to regulate physiologically relevant or therapeutic proteins, vvDD was used to deliver a conditionally stable cytokine TNF-α protein. While proven to exert cytotoxic effects against primary tumors, the systemic toxicity of TNF-α has limited its clinical use to local applications (e.g., isolated limb or organ perfusion; Lucas, R. et al. (2005) *Curr. Cancer Drug Targets* 5:381-392). In addition, TNF-α possesses antiviral effects to which the vaccinia strain Western Reserve (the basis for vvDD) is susceptible (Alcami, A. et al. (1999) *J. Gen. Virol.* 80:949-59).

An L-L106P-TNF-α chimeric gene was inserted into a strain of vvDD constitutively expressing luciferase, and dose-dependent stabilization of secreted TNF-α from cultured cells was verified (not shown). Mice bearing large (150-250 $mm^3$) subcutaneous HCT116 tumors were treated with a single intravenous injection of this virus or a PBS control. Ligand (Shield1; 10 mg/kg) was delivered i.p. to the mice every 48 hours, starting either 1 day prior to vvDD treatment or 3 days post-treatment vvDD.

When Shield1 dosing began prior to virus delivery (causing all virus-infected cells to secrete stable TNF-α, only modest levels of virus were observed in the tumor (FIG. 24A), as measured by viral luciferase expression. It is likely that secretion of TNF-α from infected cells rapidly targets these cells for destruction, thus limiting the ability of the virus to become establish within the tumor cells in which they normally proliferate. Despite the modest levels of virus observed in the tumors, the presence of ligand resulted in significantly decreased tumor burden compared to animals treated with virus alone (FIG. 24B, $p<0.05$), presumably due to the antitumor effects of the ligand-stabilized TNF-α. Shield1 delivered alone had no effect on tumor burden.

When Shield1 administration was delayed until 3 days following virus treatment, the initial delivery and persistence of viral infection (as measured by luciferase expression within the tumor) were equivalent to those observed in animals treated with virus alone (FIG. 4*a*). In these animals, the antitumor effects observed following the administration of ligand were significantly greater than those observed in animals pretreated with ligand ($p<0.05$). Seven of the eight animals demonstrated complete and durable responses (FIG. 4*b*), with no adverse physiological effects observed, demonstrating the efficacy of a conditional protein stability system to modulate tumor progression in vivo.

In a subsequent experiment, vvDD was used to deliver a conditionally stable interleukin-2 (IL-2) protein. An L-L106P-IL-2 chimeric gene was inserted into a strain of vvDD constitutively expressing luciferase. Mice bearing large (150-250 mm$^3$) subcutaneous HCT116 tumors were treated with a single intravenous injection of this virus or a PBS control. Ligand (Shield1; 10 ring/kg) was delivered intraperitoneally (i.p.) to the mice every 48 hours, starting either 1 day prior to vvDD treatment or 3 days post-treatment with vvDD (72 hours after administration of the virus).

Figure 25:
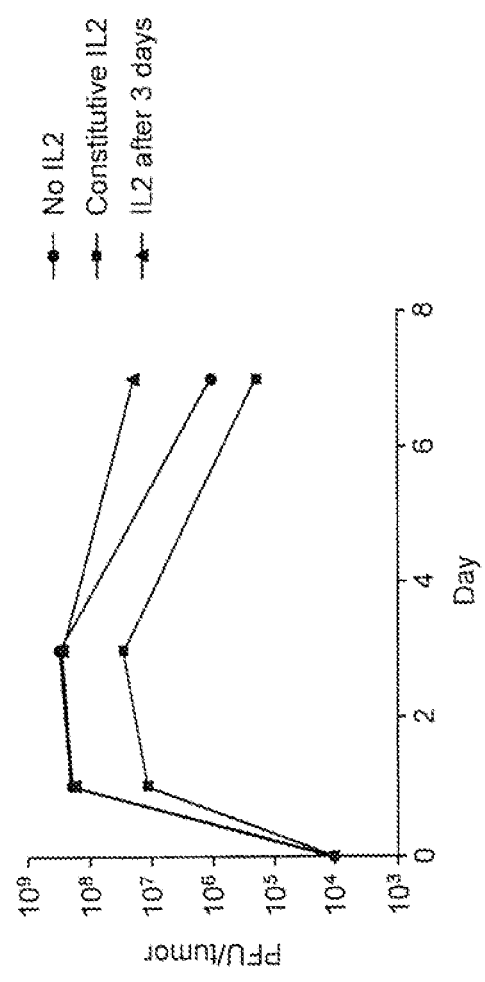
FIG. 25 relates to the systemic, targeted-delivery of a conditionally stabilized IL-2 fused to the L106P variant. The graph shows results from an experiment in which SCID mice bearing subcutaneous HCT116 xenografts (50-100 mm$^3$) received a single tail vein injection of vvDD L-L106P-IL-2 (1×10$^8$ PFU/mouse), and after 72 hours were either untreated (indicated by "No IL2"), treated with Shield1 prior to administration of the vvDD L-L106P-IL-2 construct (indicated by "Constitutive IL2"), or treated with Shield1 72 hours after administration of the vvDD L-L106P-IL-2 construct (indicated by "IL2 after 3 days").

As was observed in studies with the L-L106P-TNF-α vvDD studies described above, and as shown in FIG. 25, constitutive IL-2 expression resulted in poor viral infection within the tumor (at day 3) and more rapid clearance of the virus as compared to virus observed in mice which were administered Shield1 72 hours after administration of the vvDD L-L106P-IL-2 virus. This may be attributed to the innate immune response being rapidly induced. There was increased initial delivery to the tumor over the first 72 hours when IL-2 is destabilized in the absence of Shield1 and delayed clearance of the virus from the tumor when IL-2 is subsequently upregulated or stabilized via administration of Shield1.

Figure 26:
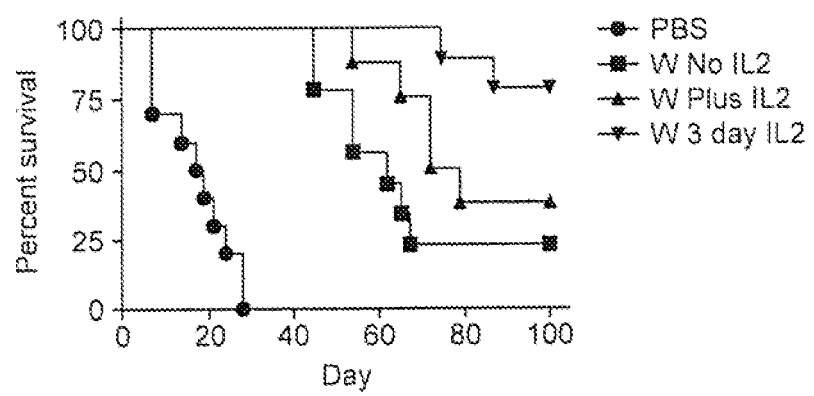
FIG. 26 shows a Kaplan-Meier survival graph relating to mice treated with Shield1 and vvDD constructs. Squares represent mice treated with Shield1 prior to administration with the vvDD L-L106D-IL-2 construct. Diamonds represent mice treated with the vvDD L-L106P-IL-2 construct prior to administration of Shield1. Triangles represent mice treated with the vvDD L-L106P-IL-2 construct only. Inverted triangles represent mice treated with Shield1 only. Circles represent mice treated with PBS (phosphate buffered saline) only.

However, when measuring effects on mouse survival, constitutive IL-2 expression was again more beneficial than no IL-2 expression. FIG. 26 suggests that regulated IL-2 expression, in which no Shield1 was administered during the first 72 hours after injection of the vvDD L-L106P-IL-2 virus, allowed more virus to accumulate in the tumor and resulted in the greater percent survival of the treated animals.

Figure 27:
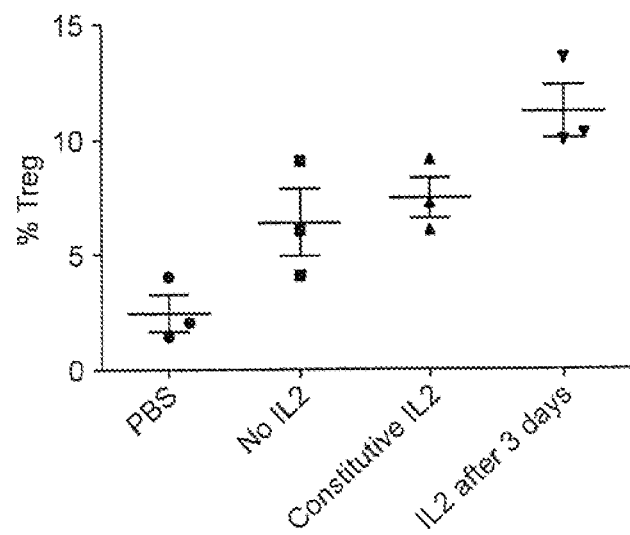
FIG. 27 shows infiltration of Treg cells into tumor cells of SCID mice bearing subcutaneous HCT116 xenografts. Tumors were excised post-mortem and cells dissociated into a single cell suspension by grinding tissue through a cell filter. The single cell suspension was stained using antibodies for T-reg markers (CD4+CD25+FoxP3+), and the percentage of cells stained positive was determined by flow cytometry. Squares represent mice treated with Shield1 prior to administration with the vvDD L-L106D-IL-2 construct. Diamonds represent mice treated with the vvDD L-L106P-IL-2 construct prior to administration of Shield1. Triangles represent mice treated with the vvDD L-L106P-IL-2 construct only. Inverted triangles represent mice treated with Shield1 only. Circles represent mice treated with PBS (phosphate buffered saline) only.

It was also observed that by delaying clearance of the virus, and thus prolonging infection of the virus, an increase in Treg infiltration was observed (see FIG. 27).

h. Regulating IL-2 Expression to Enhance Cell-Based Immunotherapy

NK-92 is a highly cytotoxic NK cell line which has been shown to exhibit substantial antitumor activity against a wide range of malignancies in vitro as well as in xenografted SCID mice. This therapeutic activity is enhanced by systemic administration of IL-2. Many immune cell therapies require administration of cytokines to enhance their benefits in vivo. Use of systemic delivery of recombinant cytokines is often toxic, and is expensive. Studies were done to determine the effects of treating tumor-bearing mice with NK-92 cells pre-infected with the vvDD-L-L106P-12 virus. As a control, mice were also treated with the vvDD control virus (not containing the L-L106P-IL2 fusion construct) and co-administered recombinant IL-2.

SCID mice bearing HCT116 tumors were treated with NK-92 cell therapy. Subcutaneous tumors were formed by injecting 5×10$^6$ HeLa cells subcutaneously into athymic nu-/nu- mice. Once formed (after 7 days), mice were treated with a single intravenous injection of (i) PBS; (ii) 1×10$^7$ NK-92 cells pre-infected (a 2-hour infection step) with 1×10$^7$ PFU vaccinia with thymidine kinase deletion or (iii) 1×10$^7$ NK-92 cells pre-infected (after 2 h infection step) with 1×10$^7$ PFU vaccinia with thymidine kinase deletion and expressing L106P-IL2 (n=8 mice per group; NK-92 cells from ATCC). Group (ii) mice were treated every 48 hours with intraperitoneal injections of 1×10$^7$ IU rhIL2 (international units recombinant human IL-2), and group (iii) were treated every 48 h with 10 mg/kg Shield1. Tumor burden was followed by caliper measurement.

Figure 28:
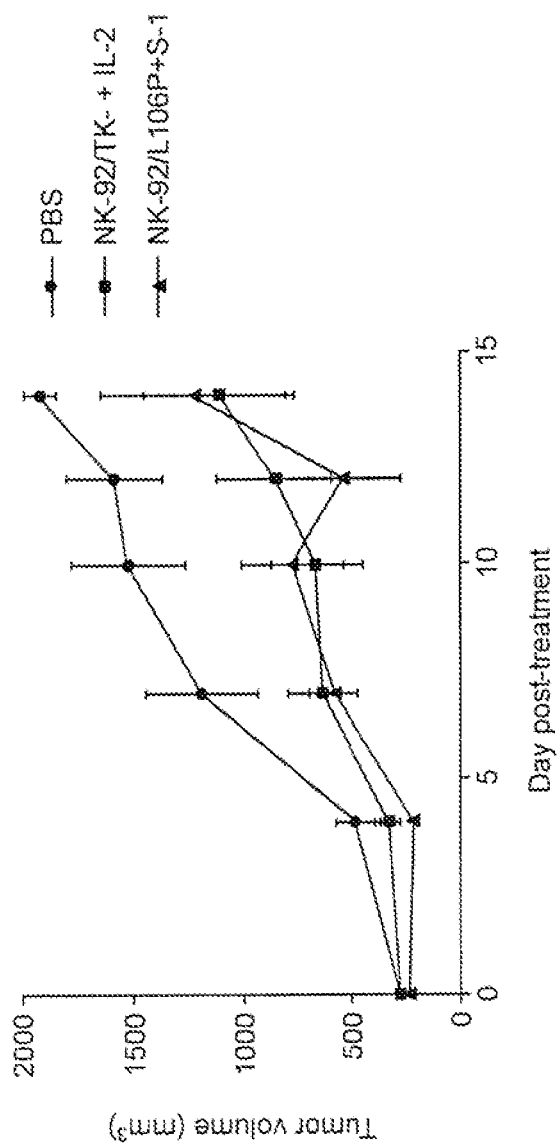
FIG. 28 shows effects of NK-92 cells infected with the vvDD-L-L106P-IL2 virus.

FIG. 28 shows injection of tumor-bearing mice with NK-92 cells preinfected with vvDD-L-L106P-IL-2 followed by administration of Shield1 equally as effective as NK-92 preinfected with control virus and further administered IL-2. Furthermore, mice injected with NK-92 cells preinfected with vvDD-L-L106P-IL-2 displayed fewer signs of toxicity.

4. STABILITY-AFFECTING PROTEIN DERIVED FROM DHFR

Dihydrofolate reductase (DHFR) is a ubiquitous enzyme involved in the regeneration of tetrahydrofolate from dihydrofolate, using NADPH. The goal was to use *E. coli* DHFR as a destabilizing domain (DD) when fused at either the N or the C-terminus of a protein of interest (POI). Since DHFR is an enzyme present in mammalian cells, mutants of DHFR having reduced catalytic ability were used to minimize perturbations to the intracellular environment caused by the introduction of an exogenous DHFR. Two of these mutations, Y100I (SEQ ID NO: 14) and G121V (SEQ ID NO: 15), in addition to reducing enzymatic activity, also destabilized DHFR relative to the wild-type sequence (SEQ ID NO: 13).

Figure 14:
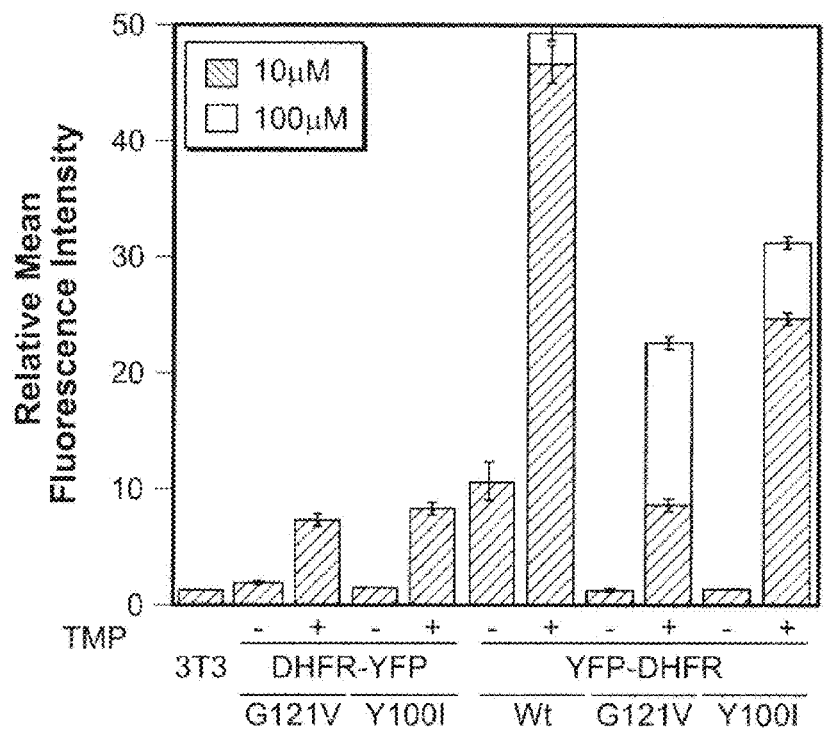
FIG. 14 is a graph showing fluorescence levels obtained using YFP-DHFR and YFP-DHFR fusion proteins. YFP fused to wild-type, G121V, and Y100I versions of DHFR were subjected to fluorescence analyses in the presence of 10 µM or 100 µM TMP.
Figure 15:
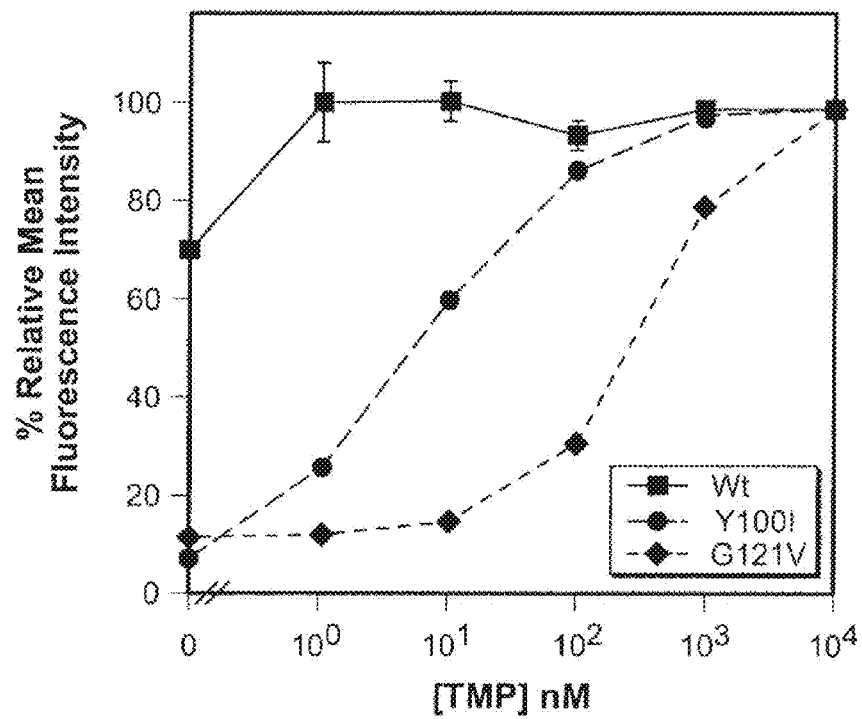
FIG. 15 is a graph showing fluorescence levels in NIH3T3 cells stably expressing DHFR-YFP fusion proteins and treated with ten-fold dilutions of TMP (10 µM to 1 nM), or mock-treated with DMSO. The fluorescence levels were monitored by flow cytometry. MFI was normalized to 100% of cells treated with 10 µM TMP at 24 hrs.

These DHFR mutants acted as destabilizing domains when fused to yellow fluorescent protein (YFP) at either the N- or the C-terminus of the YFP reporter (FIG. 14). While fusion of the mutated DHFR to either the N or C-terminus of the YFP reporter resulted in ligand-dependent stabilization of the YFP reporter in the presence of trimethoprim (TMP; indicated by "+") compared to the absence of TMP (indicated by "−"), the effect was most pronounced when the Y100I and G121V DHFR were fused to the N-terminus of the YFP reporter (FIG. 15).

To further improve the ligand-dependent stabilization characteristics of the DHFR-derived destabilizing domains for use at the C-termini of POIs, error-prone PCR was used to generate a library of additional mutants of DHFR, similar to manner in which mutants of FKBP were generated. The YFP-DHFR fusion protein library (i.e., the library of C-terminal DHFR mutants) was introduced into NIH3T3 fibroblasts using a retroviral expression system, as before, and the transduced cells were subjected to four rounds of sorting using flow cytometry. The cells were cultured in the absence of ligand in the first round of sorting. Low YFP-expressing cells were collected, cultured in the presence of 10 μM TMP for 24 hours (i.e., the second round of sorting), and then again cultured in the presence of 1 μM TMP (i.e., the third round of sorting) to isolate YFP-expressing cells with increased ligand-dependent stabilization.

Cells that displayed fluorescence were cultured in the presence of TMP, washed free of TMP, and sorted about four hours later to isolate mutants with fast kinetics of degradation in the fourth round of sorting. Low YFP-expressing cells (i.e., cell in which YFP was most degraded following the removal of the TMP from the cell medium), were collected, and the genomic DNA was isolated for sequence analysis. In this manner, two additional DHFR-derived destabilizing domains, having increased ligand-dependent stabilization, were isolated from the library screen, i.e., one double-mutant (N18T/A19V; SEQ ID NO: 17) and one single-mutant (F103L; SEQ ID NO: 16).

Figure 16A:
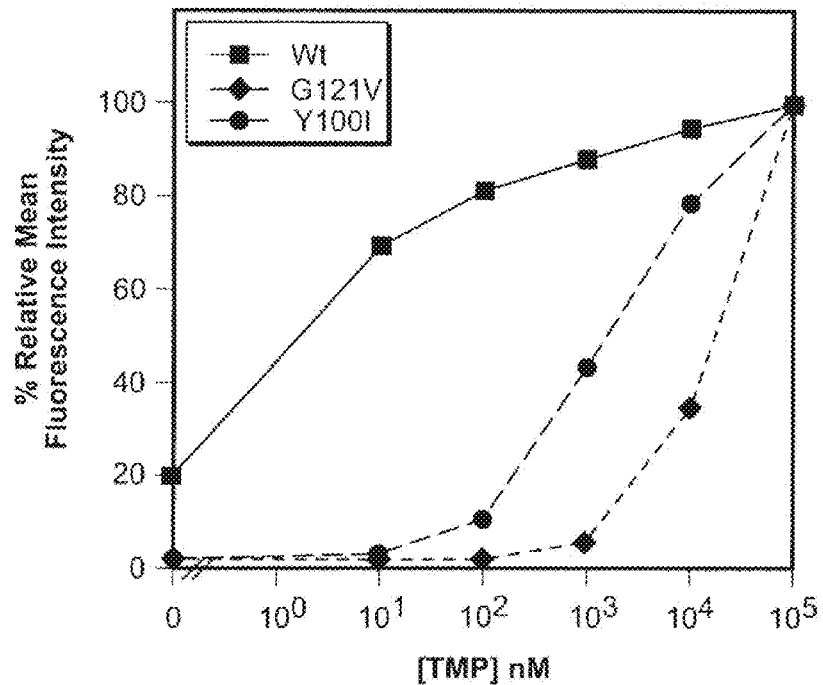
FIGS. 16A and 16B are graphs showing YFP fluorescence levels in NIH3T3 cells expressing YFP-DHFR fusion proteins and treated with ten-fold dilutions of TMP, or mock-treated with DMSO.
Figure 16B:
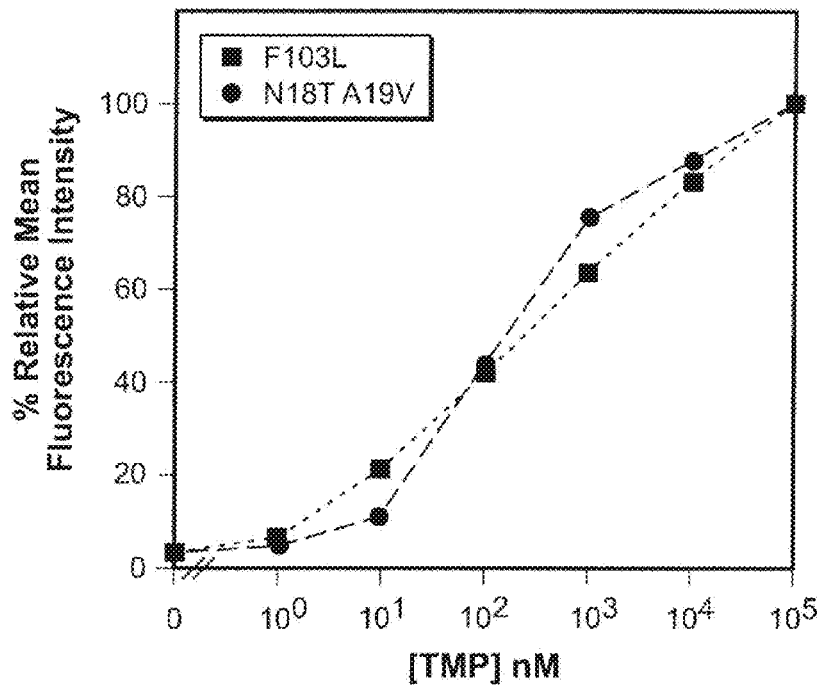
Figure 17A:
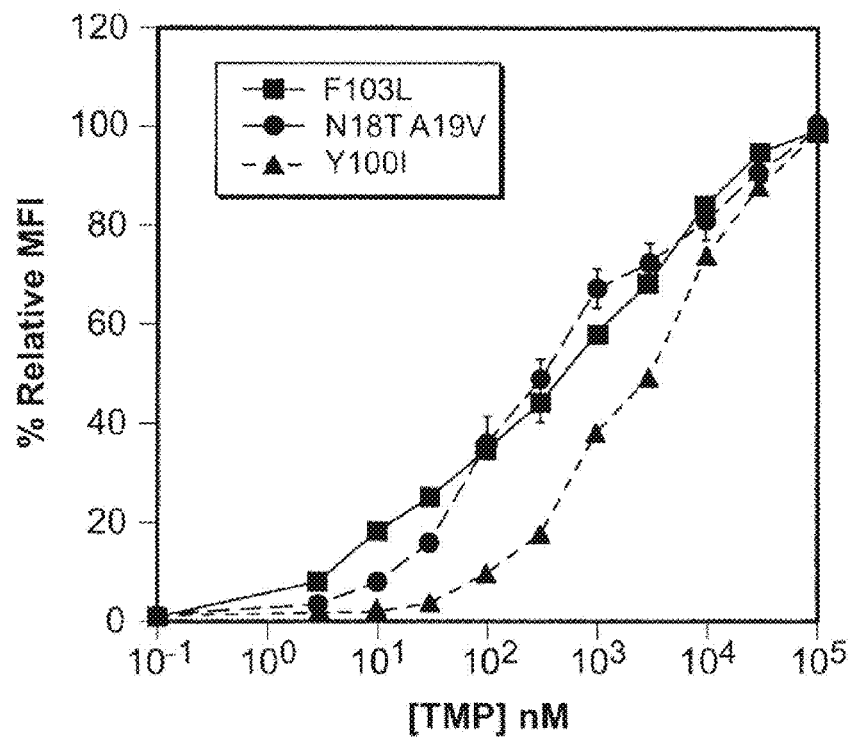
FIG. 17A is a graph showing a comparison of the stability of YFP fused at the N-terminus of several DHFR mutants.
Figure 17B:
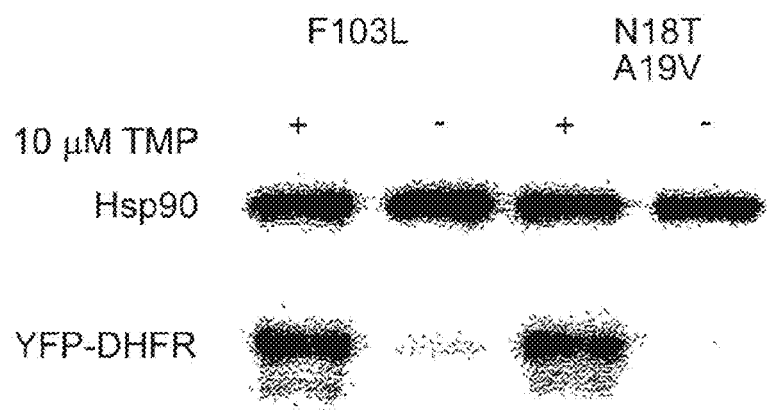
FIG. 17B shows the results of an immunoblot experiment using an antibody specific for YFP in the presence and absence of ligand.

When fused to the C-terminus of YFP, these mutants destabilized YFP in the absence of TMP and stabilized YFP in the presence of TMP. As shown in FIGS. 16A and 16B, the N18T/A19V and F103L DHFR mutants were effectively stabilized by lower concentrations of TMP relative to the original Y100I and G121V mutants. A comparison of the F103L, N18T/A19V, and Y100I DHFR mutants fused to the C-terminus of YFP is shown in FIG. 17A. An immunoblot performed using an antibody specific for DHFR confirmed that the amount of DHFR present in cells is increased in the presence of ligand (+) compared to the absence of ligand (−) (FIG. 17B).

Figure 18A:
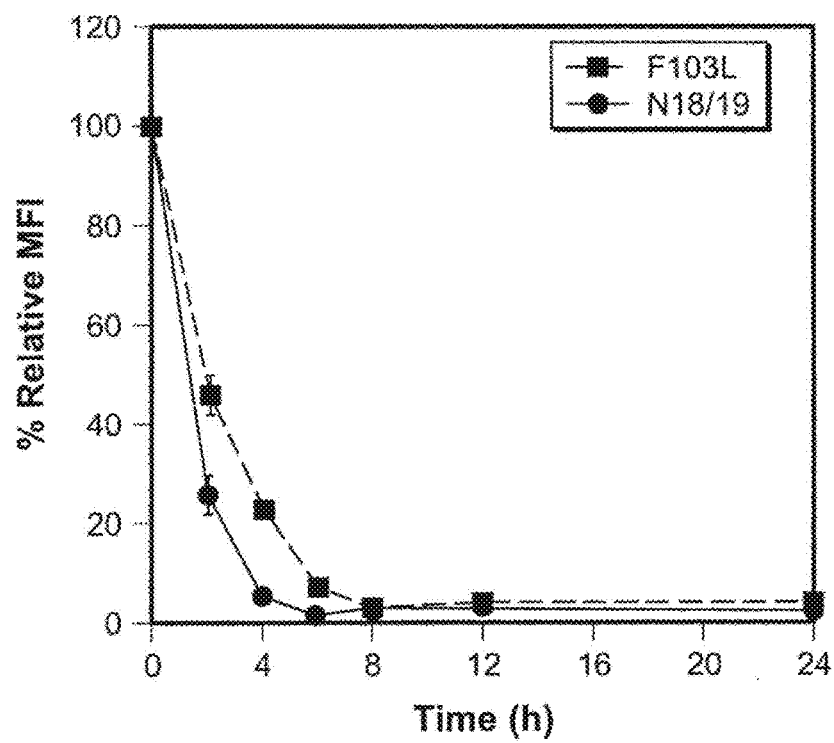
FIG. 18A is a graph showing the kinetics of YFP-DHFR decay following withdrawal of ligand.
Figure 18B:
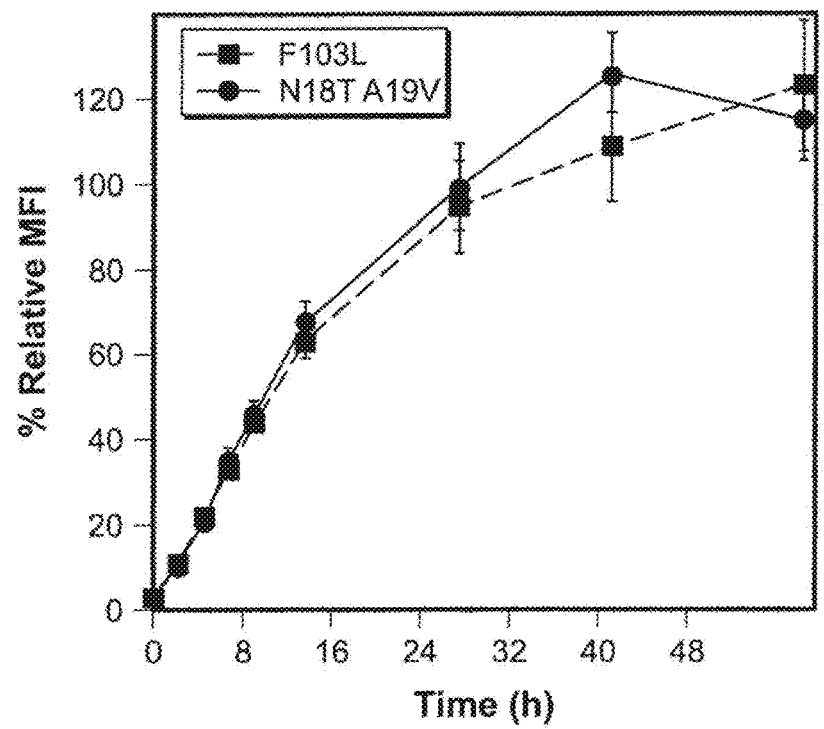
FIG. 18B is a graph showing the kinetics of YFP-DHFR stabilization following addition of ligand.

The kinetics of YFP-fusion protein decay following withdrawal of ligand is shown in FIG. 18A. The rate of decay of the C-terminal fusion protein harboring the F103L DHFR mutant was more rapid that of the C-terminal fusion protein harboring the N18T/A19V DHFR mutant, although the levels of both proteins were similar by eight hours following withdrawal of the ligand. The kinetics of YFP-fusion protein stabilization following the addition of ligand is shown in FIG. 18B. The amount of YFP detectable in cells initially increased linearly following addition of ligand, eventually reaching a maximum level.

To further improve the ligand-dependent stabilization characteristics of the DHFR-derived, stability-affecting proteins for use at the N-termini of POIs, error-prone PCR was used to generate a library of additional mutants of DHFR, similar to manner in which mutants of FKBP were generated. Using the wild-type sequence as well as the Y100I and G121V mutant sequences as the basis of the library, five double mutants were identified from the screen, namely H12Y/Y100I (SEQ ID NO: 19), H12L/Y100I (SEQ ID NO: 20), R98H/F103S (SEQ ID NO: 21) M42T/H114R (SEQ ID NO: 22), and 161F/T68S (SEQ ID NO: 23).

Figure 19A:
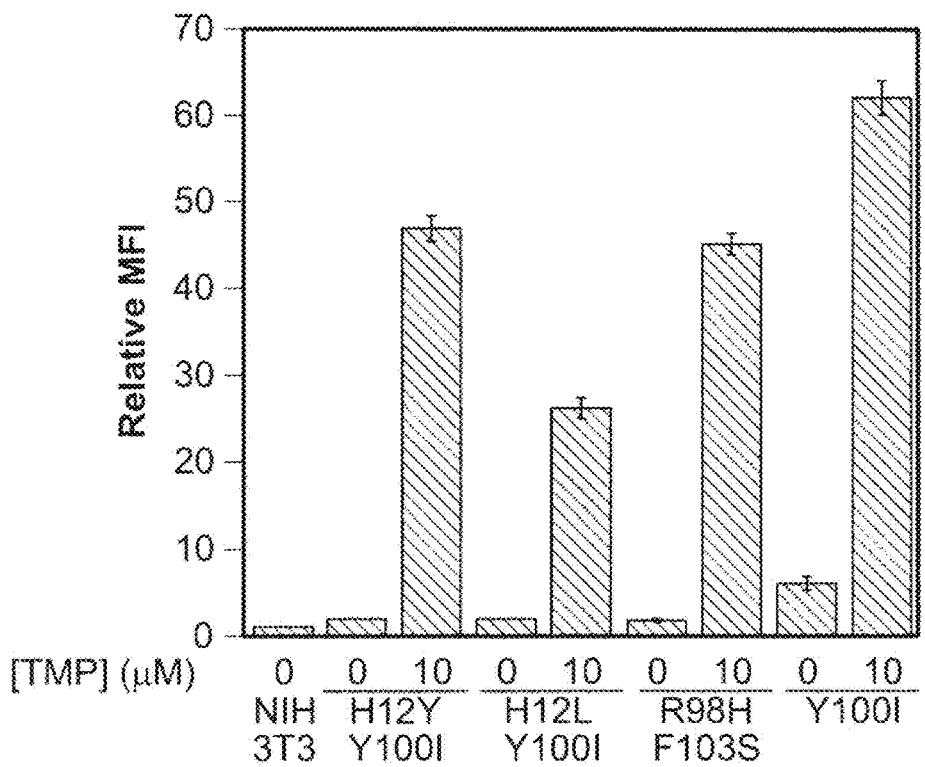
FIG. 19A is a graph showing the relative mean fluorescence intensity in cells harboring mutant DHFR-YFP fusion proteins in the absence and presence of ligand.
Figure 19B:
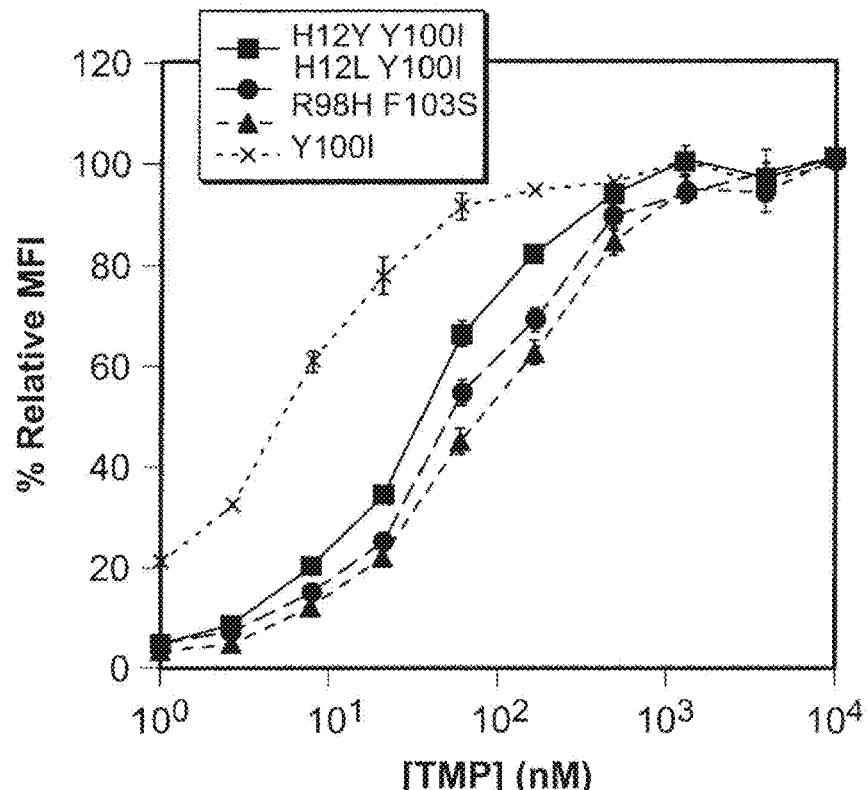
FIG. 19B shows the results of a dose response experiment, in which the cells expressing DHFR-YFP mutants were exposed to increasing amounts of ligand.

FIG. 19A shows the relative mean fluorescence intensity in cells harboring these mutant N-terminal fusion proteins in the absence and presence of ligand. While the Y100I mutant produced the greatest amount of stabilization, the difference between the levels of YFP in the absence and presence of ligand were greater with the each of the mutants H12Y/Y100I, H12L/Y100I, and R98H/F103S. FIG. 19B shows the results of a dose response experiment, in which cells harboring the same mutants as used in the experiment shown in FIG. 19A were exposed to increasing amounts of ligand. Consistent with this result shown in FIG. 19A, fusion proteins harboring the Y100I mutant are more stable in the presence of lower concentrations of ligand (or no ligand) but are no more stable in the presence of higher concentrations of ligand.

Figure 20A:
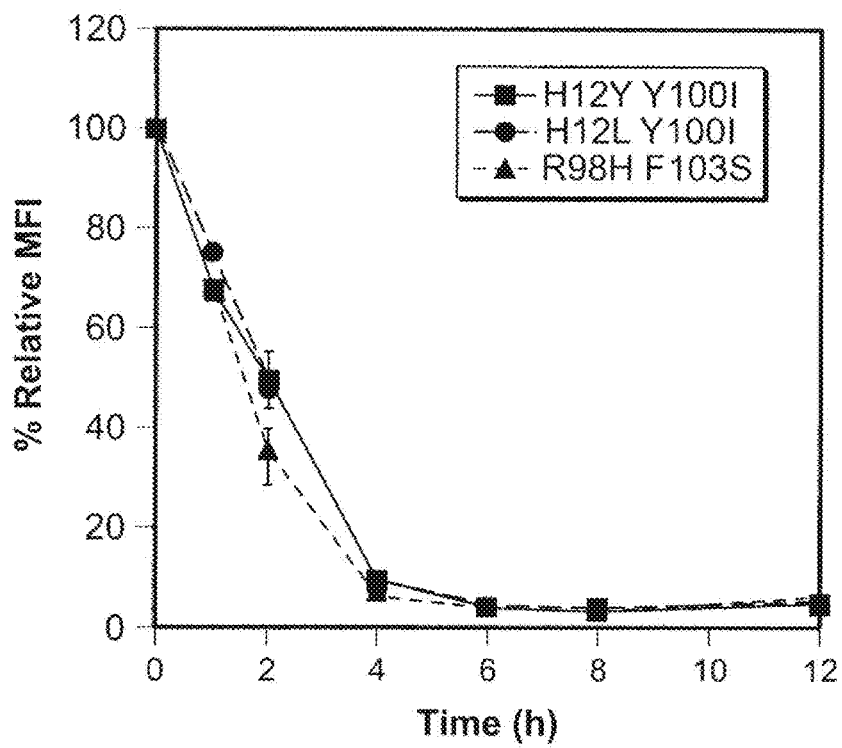
FIGS. 20A and 20B show the kinetics of decay and stabilization, respectively, of three DHFR mutants fused to the N-terminus of YFP.
Figure 20B:
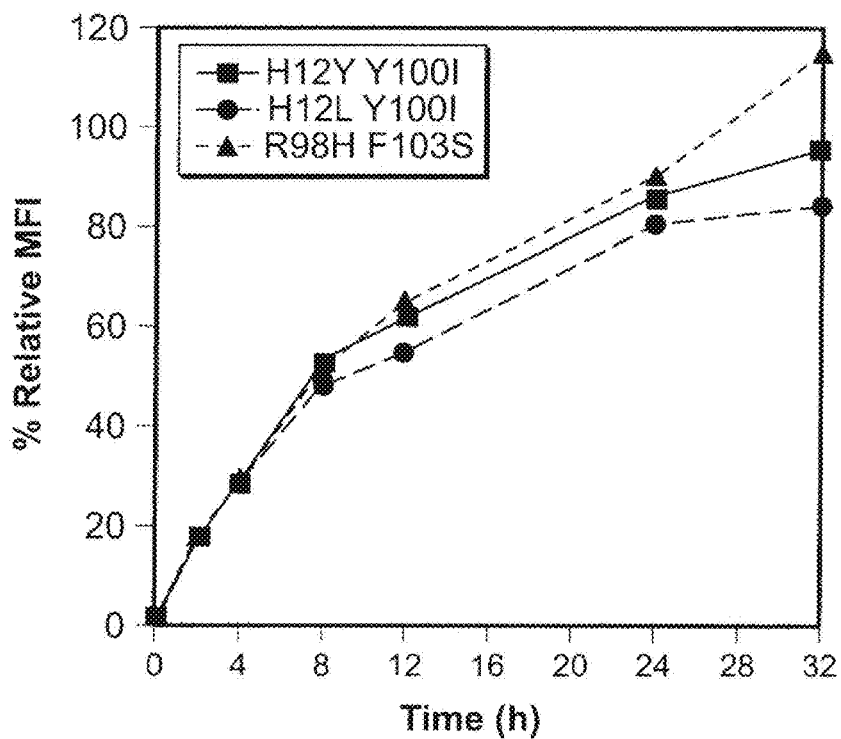

The kinetics of decay and stabilization of the N-terminal fusion proteins harboring the H12YN100I, H12L/Y100I, and R98H/F103S mutants is shown in FIGS. 20A and 20B, respectively. The three fusion proteins behaved in a similar manner, although the maximum levels of the R98H/F103S fusion protein appeared to be higher than the others.

These results demonstrate that the DHFR-derived stability-affecting proteins can function as in the context of either an N-terminal fusion or a C-terminal fusion with a POI.

5. Exemplary Systems for Conditionally Stabilizing Biological Macromolecules Ideal techniques for conditionally stabilizing biological macromolecules are specific, fast, reversible, and tunable. Cell-permeable small molecules often deliver the latter three features but, apart from a few well-known exceptions, cell-permeable small molecules are typically not specific for a single biological target. The ideal conditional stabilization technology combines the specificity of reverse genetics (i.e., well-defined DNA changes in a large genomic background) with the conditionality of cell-permeable small molecules.

Using small libraries of FKBP and DHFR variants (20,000 to 30,000 members) in combination with a convenient cell-based screening assay, several ligand stabilized destruction domains were identified, which conferred ligand-dependent stability to a POI. A list of proteins that have to date been stabilized using the methods and compositions described herein is provided in Example 12. The FKBP-derived destabilizing domains conferred ligand-dependent stability to cytoplasmic, nuclear, and a transmembrane protein, indicating that the present methods and compositions are generally applicable to the study of protein function. Stability, and therefore function, of the fusion proteins was greatly increased upon addition of a cell-permeable high-affinity ligand. For example, when the most destabilizing FKBP variants from the screen, i.e., FKBP L106P, was fused to YFP, the fusion protein is expressed at only ~1-2% of its maximum level in the absence of the stabilizing ligand. This fusion protein is fully stabilized upon the addition of 1 µM Shield1.

Variant and mutant FKBP proteins are exemplified by FKBP F36V (SEQ ID NO: 1) and the variants described in the text, Table 1 (N-terminal fusion proteins), and Table 2 (C-terminal fusion proteins). Exemplary variants have the substitutions F15S (SEQ ID NO: 2), V24A (SEQ ID NO: 3), H25R (SEQ ID NO: 4), E60G (SEQ ID NO: 5), L106P (SEQ ID NO: 6), D100G (SEQ ID NO: 7), M66T (SEQ ID NO: 8), R71G (SEQ ID NO: 9), D100N (SEQ ID NO: 10), E102G (SEQ ID NO: 11), and K105I (SEQ ID NO: 12). As tested, these variants included the F36V mutation (SEQ ID NO: 1); however, a similar mutation that accommodates a bulky side chain of a cell-permeable ligand is expected to produce similar results. Moreover, the methods allow for the screening of additional mutations that yield efficient single-ligand stabilized destruction domains.

A further mutant FKBP included additional amino acid sequence that altered the behavior of the protein such that is stabilized a POI in the absence of ligand and caused degradation of the POI in the presence of ligand. Thus the system can be used in a "drug-OFF" or "drug-ON" configuration. Such "drug-OFF" configurations may utilize a FKBP binding domain fused to a sequence substantially identical to that of SEQ ID NO:18.

The results obtained using DHFR variants suggests that Y100I (SEQ ID NO: 14) G121V (SEQ ID NO: 15) variants, particularly with the N18T/A19V (SEQ ID NO: 17) or F103L (SEQ ID NO: 16), H12Y/Y100I (SEQ ID NO: 19), H12L/Y100I (SEQ ID NO: 20), and R98H/F103S (SEQ ID NO: 21) substitutions, are well-suited for use as single-ligand stabilized destruction domain. However, the methods allow for the screening of additional mutations, including those for operation in a "drug-ON" configuration, as well as in the exemplified "drug-OFF" configuration.

The abundance of variants obtained in the screens, as well as the ability to use different ligand-binding domains, suggests that further refinements in screening may lead to additional stability-affecting proteins selected for various properties (e.g., rate of degradation, potency of stabilization, subcellular localization, and the like). Moreover, the stability-affecting proteins work when fused to either the N- or the C-terminus of a POI, illustrating the modularity of the components of the system.

The present systems work in different cell types, and work in cell culture and in animals. The system provides heretofore unprecedented control of the levels of preselected protein in cells, with excellent dose and temporal control. While the present methods have been described with reference to the FKBP and DHFR-derived destabilizing domains, other domains may be used. Preferred stability-affecting proteins modulate the degradation of a fusion protein, as determined, for example, using the kinetic and immunological assays described herein. In some embodiments, the level or extent of destabilization of the destabilization domain fusion protein is dependent upon the amount of ligand administered to the cell or to the animal expressing the destabilization domain fusion protein.

Preferred stability-affecting proteins produce a 5, 10, 20, 30, 40, 50, 60, or more-fold difference in the levels of a preselected protein that can be detected in cells or animals in the absence or presence of ligand. In some embodiments, the gene or allele encoding the naturally-occurring POI (i.e., the native protein, not a fusion protein) is deleted or disrupted in the genome of the cells or animal in which the conditional protein stability system is used or replaced by a DNA encoding the fusion protein. In this manner, the only source of the POI is the conditionally stabilized fusion protein, allowing its function to be studies in the absence of the interfering wild-type/naturally-occurring protein.

The conditional protein stability system can be used not only in vitro, but also in vivo to control the expression of a reporter gene or therapeutic gene of interest. An exemplary therapeutic gene is IL-2 but the present methods can be used control the expression of a wide variety of genes involved in tumor suppression, metabolic regulation, cell signaling, transcription, replication, apoptosis, and the like.

In some embodiments of the method, the strategy is "drug-ON," in that the stabilizing ligand must be present for stabilization of the fusion protein. However, if the POI exhibits a dominant negative phenotype, the system may be "drug-OFF," in that addition of the ligand stabilizes the dominant negative fusion protein, which in turn inhibits the function of its cellular target protein.

The stability-affecting proteins may encompass amino acid substitutions that do not substantially affect stability, including conservative and non-conservative substitutions Preferably, the amino acid sequences of the peptide inhibitors encompassed in the invention have at least about 60% identity, further at least about 70% identity, preferably at least about 75% or 80% identity, more preferably at least about 85% or 90% identity, and further preferably at least about 95% identity, to the amino acid sequences set forth herein. Percent identity may be determined, for example, by comparing sequence information using the advanced BLAST computer program, including version 2.2.9, available from the National Institutes of Health. The BLAST program is based on the alignment method of Karlin and Altschul ((1990) *Proc. Natl. Acad. Sci. U.S.A.* 87:2264-68) and as discussed in Altschul et al. ((1990) *J. Mol. Biol.* 215:403-10; Karlin and Altschul (1993) *Proc. Natl. Acad. Sci. U.S.A.* 90:5873-77; and Altschul et al. (1997) *Nucleic Acids Res.* 25:3389-3402).

Conservative amino acid substitutions may be made in the amino acid sequences described herein to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, can often be substituted with amino acids having amide side chains, such as asparagine and glutamine.

The stability-affecting proteins may be fragments of the above-described destabilizing domains, including fragments containing variant amino acid sequences. Such fragments are readily identified using the assays described herein. Preferred fragments retain the ability to bind to a stabilizing ligand with similar efficiency to the destabilizing domains described herein or with at least 90% efficiency, at least 80% efficiency, at least 70% efficiency, or even at least 50% efficiency with respect to the described stability-affecting proteins.

Figure 1B:
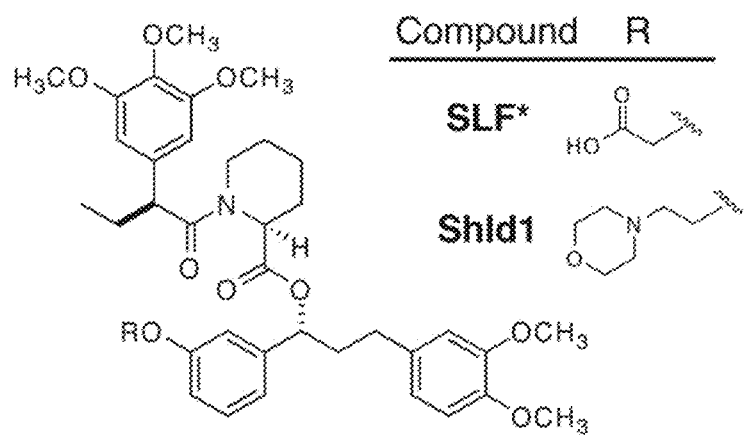
Figure 1C:
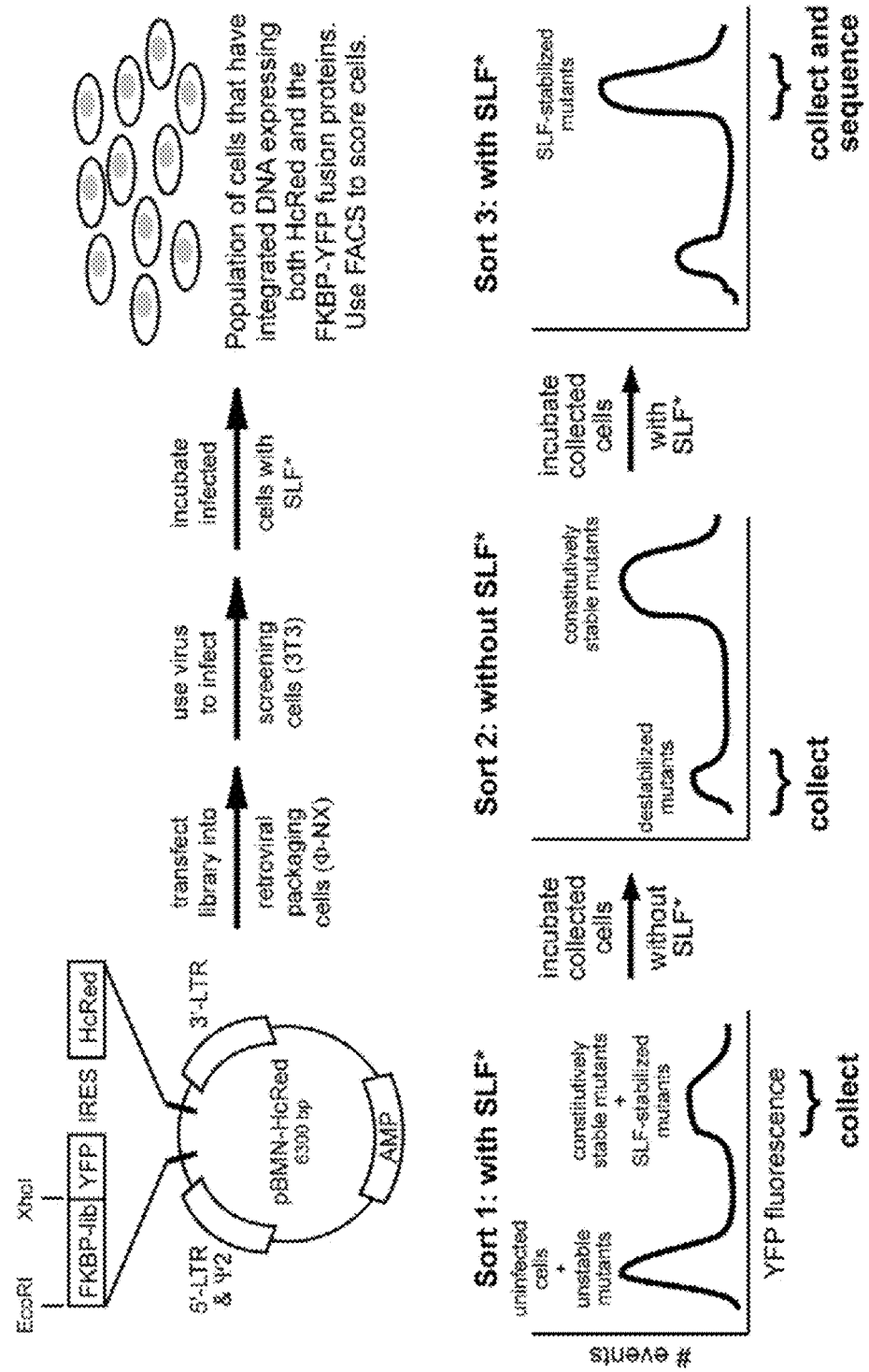
FIG. 1C is a schematic illustrating the screening strategy described in the text.

Stabilizing ligands for use according to the methods described herein are exemplified by SLF* (i.e., 1-[2-(3,4,5-trimethoxy-phenyl)-butyryl]-piperazine-2-carboxylic acid 1-(3-carboxymethoxy-phenyl)-3-(3,4-dimethoxy-phenyl)-propyl ester) and Shield1 (i.e., 1-[2-(3,4,5-trimethoxy-phenyl)-butyryl]-piperazine-2-carboxylic acid 3-(3,4-dimethoxy-phenyl)-1-[3-(2-morpholin-4-yl-ethoxy)-phenyl]-propyl ester), both shown in FIG. 1B, and MaRap (C20-methallylrapamycin). A feature of these FKBP ligands is that they contain a "bump" (i.e., a bulky side-chain substituent) that prevents the ligand from binding to wild-type (i.e., naturally-occurring) FRB domain of FRAP/mTor, thereby minimizing the biological effects associated with rapamycin administering. The "bump" in the ligand corresponds to a "hole" (i.e., a compensatory, cavity-forming substitution or mutation) in the FRB domain of FRAP/mTor.

Other stabilizing ligands may be used according to the present methods. Such ligands include rapamycin-derived ligands containing other bulky side-chains at positions of the molecule known to mediate binding to FKBP. As illustrated by the exemplary stabilizing ligands, the particular side-chain is not critical, with both aliphatic and aromatic side-chains producing acceptable results. Numerous other bulky R-groups are expected to give similar results, including but not limited to alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic groups. The R-groups may contain a hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and secondary or tertiary amine, (i.e., —NR'R" where each R' or R" is independently selected from hydrogen, alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic, etc.

A related aspect of the methods and compositions are cells transfected with nucleic acids encoding a fusion protein comprising a protein of interest fused in frame to a stability-affecting protein. Expression of the fusion protein may be driven by the endogenous promoter, ideally reproducing the spatial and temporal expression patterns of the unmodified gene. The cells may be transfected, e.g., using an expression vector, or transduced (i.e., infected) using a viral vector, including but not limited to a vector derived from a retrovirus (e.g., a lentivirus), herpesvirus, pox virus, adenovirus, adenoassociated virus, or an RNA virus, such as poliovirus, flavivirus, alphavirus, or the like. The exemplary viral vector was based on a retrovirus.

The system was shown to be effective eukaryotic cells, including mammalian cells and protozoan parasites; therefore, the system can be expected to work in various eukaryotic cells, including those of humans, primates, rodents, dogs, cats, horses, cows, sheep, insects, amphibians, and apicomplexan parasites. The cells may be in culture or in a living organism. As noted above, the wild-type or naturally-occurring gene or allele encoding the POI may be deleted to facilitate study of the conditionally stabilized POI.

The present methods and compositions also allow the creation of transgenic animals harboring engineered alleles that direct the expression of a ligand-stabilized POI. Expression of the fusion protein may be driven by the endogenous promoter, ideally reproducing the spatial and temporal expression patterns of the unmodified gene. The ligand may be administered regularly from an early age (including in utero) to stabilize the fusion protein until the mice achieve a specified age, at which time withdrawal of the ligand results in a the rapid degradation of the fusion protein. Unlike Cre-mediated gene disruption (see Background section), this method is reversible, simply by reinitiating the administration of the ligand, allowing the rapid, reversible, and conditional control of protein function in a complex system.

The ability to specifically and conditionally stabilize a POI in a cell will enable the study of many proteins to determine their biological function and importance in a cell. The present methods and composition represent a significant improvement over current methods of conditional protein regulation.

6. Kits of Parts

The methods and compositions described herein may be packaged together with instructions for use, as in a kit of parts. Preferred kits of parts include nucleic acids encoding stability-affecting proteins, one or more ligands, and instructions for use. The instructions may contain information relating the inserting (i.e., "cloning") a POI into a plasmid, in-frame with a stability-affecting protein. The instructions may also include dosing recommendations and hardware, such as syringes, to deliver the fusion protein to an organism or to cells.

EXAMPLES

The following examples are illustrative in nature and are in no way intended to be limiting. Examples relating to generating and screening stability-affecting proteins apply generally to FKBP, DHFR, and other polypeptides that can be used as stability-affecting proteins.

Example 1: FKBP Library Generation

Diversity in the FKBP sequence was generated using a combination of error-prone PCR and nucleotide analog mutagenesis. Primers for mutagenic PCR were designed to anneal upstream of the 5' restriction site to be used for cloning the mutagenesis products into the pBMN iHcRed-tandem retroviral expression vector and downstream of the 3' restriction site. Three independent condition sets were used to generate diversity. Condition set "A" utilized 4 ng template, 0.5 µM of each oligonucleotide primer, 5 units Taq polymerase, 5 mM $MgCl_2$, 0.2 mM $MnCl_2$, 0.4 mM dNTPs in equal ratio and an excess of 0.2 mM dATP and dCTP. Condition set "B" was identical to A except that dGTP and dTTP were present in excess. Condition set C utilized the non-natural nucleotides 8-oxo-dGTP and dPTP to encourage nucleotide misincorporation (Zaccolo, M. et al. (1996) *J. Mol. Biol.* 255:589-603). The FKBP libraries were pooled and ligated into the pBMN iHcRed-t retroviral expression vector, affording a library containing ~$3 \times 10^4$ members.

Example 2: FKBP Synthetic Ligands

SLF* and Shield1 were synthesized essentially as described (Holt et al., 1993; Yang et al., 2000).

Example 3: Cell Culture, Transfections, and Transductions

The NIH3T3 cell line was cultured in DMEM supplemented with 10% heat-inactivated donor bovine serum (Invitrogen), 2 mM glutamine, 100 U/ml penicillin and 100 µg/ml streptomycin. All other cell lines were cultured with 10% heat-inactivated fetal bovine serum (Invitrogen), 2 mM glutamine, 100 U/ml penicillin and 100 µg/ml streptomycin.

The ΦNX ecotropic packaging cell line was transfected using standard Lipofectamine 2000 protocols. Viral supernatants were harvested 48 hrs post-transfection, filtered and concentrated 10-fold using an Amicon Ultra centrifugal filter device (Millipore, 100-kDa cut-off). NIH3T3 cells were incubated with the concentrated retroviral supernatants supplemented with 4 µg/ml polybrene for 4 hrs at 37° C. Cells were washed once with PBS and cultured in growth media for 24-36 hrs to allow for viral integration, then assayed as described.

HeLa cells were plated at $7 \times 10^4$ cells per well of a 24-well plate 12 hours prior to transfection. Cells were transfected with either 200 ng Silencer® Lamin A/C siRNA (Ambion) or a negative control siRNA using the GeneSilencer protocol. Cell lysates were immunoblotted with an anti-lamin A/C antibody (Clone 14, BD Transduction Laboratories).

Example 4: Flow Cytometry

Twenty-four hours prior to analysis, transduced NIH3T3 cells were plated at $1 \times 10^5$ cells per well of a 12-well plate and treated as described. Cells were removed from the plate using PBS+2 mM EDTA, washed once with PBS, and resuspended in 2004 PBS. Cells were analyzed at the Stanford Shared FACS Facility using FlasherII with 10,000 events represented.

Example 5: Protein-of-Interest Origin and Antibodies

Proteins tested as fusions to destabilizing domains were of the following origin, and the following antibodies were used for immunoblotting: Arf6 Q67L (human, 3A-1, Santa Cruz Biotechnology); Ar17 Q72L (human, BC001051, Protein Tech Group, Inc.); Cdc42 Q61L (human, P1, Santa Cruz Biotechnology); CD8α (mouse, 5H10, Caltag Laboratories); CDK1 (human, H-297, Santa Cruz Biotechnology); CREB (mouse, 86B10, Cell Signaling Technology); FKBP (human, 2C1-97, BD PharMingen); GSK-3β (mouse, 0011-A, Santa Cruz Biotechnology); Hsp90 (mouse, 68, BD Transduction Laboratories); p21 (human, H-164, Santa Cruz Biotechnology); Rac1 Q61L (human, C-11, Santa Cruz Biotechnology); RhoA Q63L (human, 26C4, Santa Cruz Biotechnology); Securin (human, Z23.YU, Zymed Laboratories); YFP, Aequorea victoria (JL-8, Clontech).

Example 6: Phalloidin Staining and Microscopy

NIH3T3 cells stably expressing constitutively active GTPases fused to destabilizing domains were treated with 1 µM Shield1 for 24 hr. At this time, cells were washed once with PBS, plated at 8×10³ cells in 4-well LabTek Chambered coverglass (NUNC) coated with 1 mg/ml poly-D-lysine (Sigma), along with mock-treated transduced cells and transduced cells treated with 1 µM Shield1. Cells were cultured for 24 hr in 10% DBS, then cultured in serum-free media for 12 hr. Cells were then washed with PBS, fixed in 4% paraformaldehyde for 15 min, permeabilized in 0.2% Triton X-100 for 5 min, stained with 1 µg/ml Alexa Fluor 488-conjugated phalloidin (Invitrogen; A12379) in PBS for 20 min, and washed with PBS. Fixed cells were imaged using a Bio-Rad Radiance 2100 confocal microscope.

Example 7: Identification of Ligand-Responsive Destabilizing Domain

To identify FKBP variants (i.e., mutants) with a high affinity for the synthetic FKBP ligand SLF* (FIG. 1B) a cell-based screening assay was used in which a library based on the FKBP F36V gene sequence was generated using error-prone PCR, and then cloned in-frame in front of yellow fluorescent protein (YFP). Measurement of the fluorescence of YFP served as an indicator of FKBP stability.

A Moloney murine leukemia retroviral expression system was used to stably integrate this library of DNAs encoding FKBP-YFP fusion proteins into NIH3T3 fibroblasts. The transduced cells were subjected to three rounds of sorting using flow cytometry. In the first round, cells were treated with the FKBP ligand SLF* (5 µM, FIG. 1B) for 24 hours prior to sorting. The fluorescent cells were collected and further cultured in the absence of ligand for 60 hours. Reanalysis revealed that approximately 5% of the cell population exhibited decreased fluorescence levels, indicating that the majority of the sequences were either unmutated or contained mutations that did not affect stability of the fusion protein. This small population of cells exhibiting decreased fluorescence was collected and cultured again in the presence of SLF* (5 µM) for 24 hours, at which time YFP-expressing cells were collected and the genomic DNA was isolated. The sequence analysis of 72 FKBP-derived library clones (Table 1) revealed several frequently recurring mutations that were distributed fairly evenly over the primary amino acid sequence. All sequences maintained the F36V mutation. To validate the screening method and to further characterize the FKBP-derived ligand-responsive destabilizing domains, we chose five variants (F15S, V24A, H25R, E60G, and L106P) for further analysis.

TABLE 1

Shield1-dependent N-terminal FKBP mutants isolated from library screen.

| Clone | No. Mutations | Identity of mutations |
|---|---|---|
| 1-37 | 0 | none |
| 38 | 0 | stop codon introduced |
| 39 | 0 | dropped base |
| 40 | 0 | mixed sequence |
| 41 | 1 | F15S |

TABLE 1-continued

Shield1-dependent N-terminal FKBP mutants isolated from library screen.

| Clone | No. Mutations | Identity of mutations |
|---|---|---|
| 42 | 1 | F15S |
| 43 | 1 | V24A |
| 44 | 1 | K34R |
| 45 | 1 | S38P |
| 46 | 1 | F46L |
| 47 | 1 | V63F |
| 48 | 1 | M66V |
| 49 | 1 | R71S |
| 50 | 1 | P78T |
| 51 | 1 | D79G |
| 52 | 1 | A81V |
| 53 | 1 | E102G |
| 54 | 1 | L106P |
| 55 | 2 | F15S, N43S |
| 56 | 2 | Y26H, Q53R |
| 57 | 2 | G28R, E31G |
| 58 | 2 | F48I, E60G |
| 59 | 2 | G51D, S77P |
| 60 | 2 | E54G, F99L |
| 61 | 2 | Q65R, L106P |
| 62 | 3 | V2A, L50A, L106A |
| 63 | 3 | T6A, V24A, I91A |
| 64 | 3 | Q3R, N43S, G69S |
| 65 | 3 | K44E, E60G, V63A |
| 66 | 3 | W59R, E60G, I76M |
| 67 | 4 | R13H, V24A, K35A, M49A |
| 68 | 6 | S8P, G28R, L30P, S39P, F99L, D100G |
| 69 | 7 | F15S, H25R, K47G, K73R, I76V, D79G, I90V |
| 70 | 10 | H25R, M29T, L30P, D32G, P45S, F48L, K52E, S67G, L104P, L106P |
| 71 | 11 | H25R, M29T, L30P, D32G, P45S, F48L, K52E, E54G, S67G, L104P, L106P |
| 72 | 16 | I7T, S8P, P9L, D11N, T14A, F15L, H25Y, L30P, D37N, D41N, A64T, I76M, G83D, T85A, I91V, F99V |

Example 8: Characterization of Ligand-Responsive Destabilizing Domain

The variant FKBP-derived, ligand-responsive destabilizing domains were assayed for stability in the presence and absence of a derivative of SLF* in which the carboxylic acid is replaced with a morpholine group (FIG. 1B). This functional group is commonly appended to drug-like molecules to improve their pharmacokinetic properties, and was added to SLF* at a position unlikely to interfere with FKBP binding. The modified SLF*-derived, cell-permeable FKBP ligand was designed to protect an otherwise unstable protein domain from degradation, and was therefore called Shield1 (Shield1).

Each variant FKBP-derived, ligand-responsive destabilizing domain was separately transduced into NIH3T3 cells, and YFP fluorescence levels were measured in the absence of Shield1 (FIG. 2A). All five mutants showed decreased fluorescence levels with respect to a positive control, indicating that the variants obtained from the library screen were destabilizing. The most destabilizing variation, L106P, produced YFP fluorescence at a level of only 1-2% relative to the positive control. All FKBP-derived, ligand-responsive destabilizing domain variants produced increased fluorescence signal when incubated in the presence of Shield1 (FIG. 2A). The difference in the efficiency of rescue (La, stabilization by Shield1) varied by over an order of magnitude, as shown in FIG. 2B. Variant V24A showed the most efficient rescue, with the extracellular concentration of Shield1 required to obtain 50% of the maximum YFP signal being 5 nM (i.e., $EC_{50}$~5 nM). The more destabilizing L106P variant required higher concentrations of Shield1 ($EC_{50}$~100 nM) to stabilize the YFP fusion protein.

In a kinetic study of NIH3T3 cells stably expressing each of the five FKBP-derived, ligand-responsive destabilizing domain variants, YFP fluorescence increased at approximately the same rate upon addition of Shield1, with maximum fluorescence achieved at 24 hours and stably maintained for at least an additional 48 hours without further addition of Shield1 (FIG. 2C). These results suggest that, upon addition of Shield1, these FKBP mutants are able to adopt a conformation that approximates the stability of the wild type protein, and that increases in fluorescence are mainly a function of the rate of protein synthesis and/or YFP maturation within the cell. In a related experiment, NIH3T3 cells transduced with the FKBP L106P-YFP fusion (hereafter L106P-YFP) were treated with various concentrations of Shield1 and YFP fluorescence was monitored as a function of time (FIG. 2C). YFP expression is observed within 15 min, and cells treated with lower concentrations of Shield1 reach steady state expression levels more rapidly than cells treated with higher concentrations of Shield1.

Upon withdrawal of Shield1, distinct differences in fluorescence decay profiles were observed among the FKBP-derived, ligand-responsive destabilizing domain variants (FIG. 2D), revealing a correlation between the rate of degradation and the degree of destabilization. Variant H25R, which is the least destabilizing of this group, showed the slowest rate of degradation, whereas L106P, the most destabilizing of the five, was degraded most quickly, with protein levels becoming negligible within four hours.

To correlate YFP fluorescence with intracellular protein levels and to look for evidence of partial proteolysis, cells stably expressing each destabilizing domain fused to YFP were either mock-treated or treated with Shield1. Cell lysates were prepared and used for immunoblot analysis along with antibodies specific for either FKBP (FIG. 2E) or YFP (data not shown). Neither antibody was capable of detecting protein in lysates from mock-treated cells, whereas the fusion protein was detected in Shield 1-treated cells. Cells transformed with either the F15S or L106P variant were also examined using fluorescence microscopy, which demonstrated Shield1-dependent fluorescence (data not shown).

The mechanism of degradation was examined for the F15S and L106P variants. Since the ubiquitin-proteasome system is a major mediator of intracellular protein degradation (Pickart, C.M. (2004) Cell 116:181-190; Bence, N. F. et al. (2001); Hicke, L. and Dunn, R. (2003) Annu. Rev. Cell Dev. Biol. 19:141-172). Science 292:1552-1555), the cells expressing either the FKBP-derived, ligand-responsive destabilizing domain variants F15S or L106P were incubated with MG132 (FIG. 2F) or lactacystin (FIG. 9), which inhibit ubiquitin-proteasome-mediated protein degradation. The inability of the cells to degrade the variant FKBP fusion proteins following the withdrawal of Shield1, indicating that degradation was mediated, at least in part, by the proteasome.

RNAi has become a widely used tool for reducing intracellular levels of a protein of interest. The rate of RNAi-mediated silencing of an endogenous gene was compared to the rate of degradation achieved through the fusion of a protein of interest to the above-described destabilizing domain. Lamin A/C is a non-essential cytoskeletal protein commonly used as a control in RNAi experiments. Previous studies have shown more than 90% reduction in lamin A/C expression in HeLa cells assayed 40 to 45 hours after transfection of the cells with a cognate siRNA duplex (Elbashir, S. M. et al. (2001) Nature 411:494-498), which suggests that the half-life of the lamin A/C proteins is about 10-12 hours. This half-life is significantly shorter than that of YFB, which is 26 hrs (Corish, P. and Tyler-Smith, C. (1999) Protein Eng. 12:1035-1040 and Tyler-Smith, 1999). HeLa cells transfected with siRNA against lamin NC showed a decrease in protein levels after 24 hours, with a significant reduction in lamin A/C observed by 48 hours (FIG. 2G, FIG. 10). In contrast, cells stably expressing L106P-YFP show nearly complete degradation of the fusion within 4 hours of removal of Shield1. These results demonstrate that fusion of a destabilizing domain to a protein of interest dramatically reduces its stability in cultured cells, causing the protein of interest to be quickly degraded upon removal of the stabilizing ligand.

Example 9: Dose-Dependent Regulation of Intracellular Protein Levels

To determine the ability of the variant FKBP fusion proteins, in combination with Shield1, to modulate the levels of YFP in a dose-dependent manner, NIH3T3 cells stably expressing the L106P-YFP variant were exposed to different concentrations of Shield 1 over the course of one week (FIG. 3). The smooth line (i.e., having no data points indicated by squares) are the predicted YFP levels based on the dose-response curve shown in FIG. 2B, as measured by flow cytometry.

Example 10: Identification and Characterization of C-Terminal Destabilizing Domains A screen of a YFP-FKBP library (reversed compared to the previous orientation of FKBP and YFP) was performed to identify candidate C-terminal destabilizing domains (Table 2). Six FKBP variants (M66T, R71G, D100G, D100N, E102G, and K105I) were selected for further analysis. Overall, destabilizing domains fused to the C-terminus of YFP are less destabilizing than their N-terminal counterparts (Table 1). For example, when the L106P mutant is fused to the N-terminus of YFP (L106P-YFP), fluorescence is only ~1-2% of that observed in the presence of Shield1. However, when the orientation is reversed (YFP-L106P), fluorescence in the absence of Shield1 is ~10% of that observed in its presence.

TABLE 2

Shield1-dependent C-terminal FKBP mutants isolated from library screen.

| Clone | No. mutations | Identification of mutations |
|---|---|---|
| 1-5 | 0 | None |
| 6 | 0 | Stop codon introduced |
| 7-8 | 0 | Incomplete sequence |
| 8-12 | 0 | Mixed sequence |
| 13 | 1 | G1R |
| 14 | 1 | L30P |
| 15 | 1 | M66T |
| 16 | 1 | D100G |
| 17 | 1 | D100N |
| 18 | 1 | E102G |
| 19 | 1 | E102G |
| 20 | 1 | E107G |
| 21 | 2 | E5K, R71G |
| 22 | 2 | E5K, R71G |
| 23 | 2 | D11G, K73R |
| 24 | 2 | Q20L, T27A |
| 25 | 2 | T21A, H25R |

TABLE 2-continued

Shield1-dependent C-terminal FKBP mutants isolated from library screen.

| Clone | No. mutations | Identification of mutations |
|---|---|---|
| 26 | 2 | C22F, M29T |
| 27 | 2 | M29T, D100G |
| 28 | 2 | E31G, E107G |
| 29 | 2 | K34Q, Q70R |
| 30 | 2 | S67G, Q70R |
| 31 | 2 | G89S, K105I |
| 32 | 3 | V4M, G33R, G58S |
| 33 | 3 | D11A, D32G, K44R |
| 34 | 3 | D11G, N43D, D79G |
| 35 | 3 | D11G, R13C, F48L |
| 36 | 3 | G19D, K35R, K105E |
| 37 | 3 | E31G, R71G, K105E |
| 38 | 3 | K35R, G69S, I76V |
| 39 | 3 | E61G, H94R, K105R |
| 40 | 3 | D79G, P93S, D100R |
| 41 | 3 | D79G, P93S, D100R |
| 42 | 4 | T6A, I7T, T14I, M66V |
| 43 | 4 | T21A, N43D, A72V, E107G |
| 44 | 4 | M29T, E31K, K52R, T75A |
| 45 | 4 | R42G, K52R, D79G, E107G |
| 46 | 5 | I7T, M29V, F48L, T85A, K105R |
| 47 | 7 | Q3R, F15S, T21A, K44E, K73E, P88T, K105R |
| 48 | 8 | T6S, P9S, M29V, K34R, R42G, Q53R, K73R, D79G |

Figure 11:
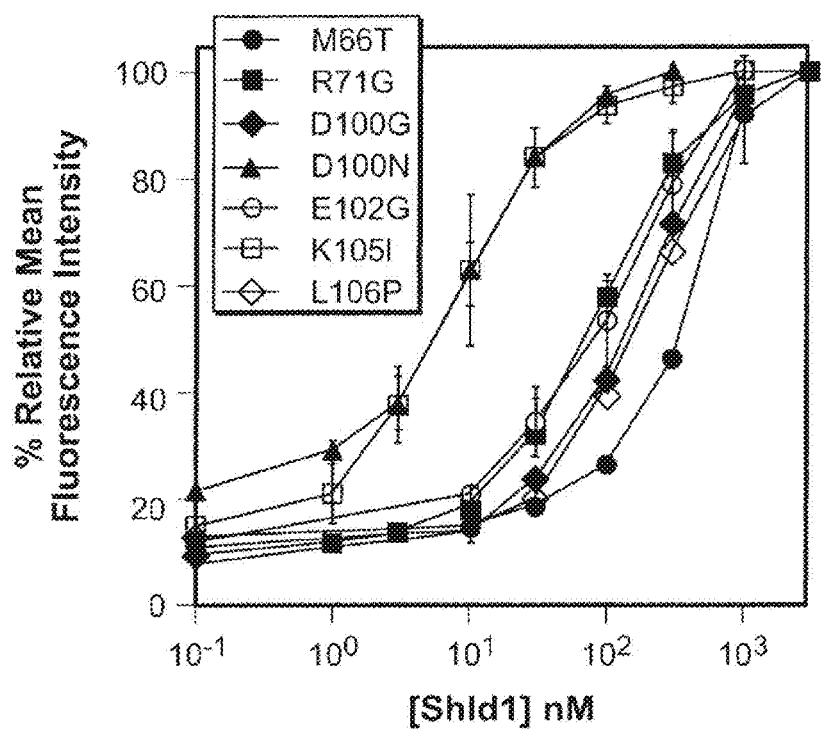
FIG. 11 is a graph showing the levels of fluorescence of various YFP-FKBP fusion proteins (i.e., C-terminal FKBP mutants) in response to different concentrations of Shield1. NIH3T3 cells stably expressing YFP-FKBP fusion proteins were incubated with three-fold dilutions of Shield1 (3 µM to 0.1 nM) and fluorescence was monitored by flow cytometry. The data are presented as MFI±SEM relative to that of the maximum fluorescence intensity observed for the individual variant. The experiment was performed in triplicate.

Nonetheless, C-terminal destabilizing domains respond to Shield1 in a dose-dependent manner comparable to N-terminal destabilizing domains, with $EC_{50}$ values ranging from 10 nM to 100 nM (FIG. 11). As observed with N-terminal destabilizing domains, all variants exhibit nearly identical rates of increase in fluorescence upon addition of Shield1, regardless of the degree of instability conferred (not shown).

Example 11: Ligand-Dependent Stability in Multiple Cells Lines

Destabilizing domains fused to either the N- or C-terminus of YFP were also transfected into several different cells lines, i.e., NIH3T3, HEK 293T, HeLa, and COS-1 cells, to assess the behavior of the FKBP-derived, ligand-responsive destabilizing domain variants in different cells. Shield1-dependent fluorescence was observed in all cell lines (Table 3), demonstrating that ligand-dependent stability is not restricted to one cell type. The FKBP-derived destabilizing domains can be stabilized using Shield1 as well as the commercially available ligand, FK506 (FIG. 13). However, unlike Shield1, FK506 perturbs the cellular environment by inhibiting calcineurin.

TABLE 3

Fluorescence of FKBP-YFP fusions (N-terminal or C-terminal) in transiently transfected cell lines in the absence of Shield1.

| | % Residual YFP Fluorescence* | | | |
|---|---|---|---|---|
| | FKBP-YFP | | YFP-FKBP | |
| | F15S | L106P | D100G | L106P |
| NIH3T3 | 7 | 8 | 16 | 16 |
| HEK 293T | 7 | 5 | 15 | 19 |
| HeLa | 8 | 6 | 9 | 12 |
| COS-1 | 12 | 19 | 22 | 26 |

*Data are presented as the average mean fluorescence intensity relative to that of the maximum fluorescence intensity observed for the individual mutant. The experiment was performed in duplicate.

Example 12: Ligand-Dependent Stability for a Variety of Proteins

To show that FKBP variants are efficient in destabilizing proteins other than YFP, the F15S and L106P variants were fused at the N-termini, to the kinases GSK-3β and CDK1, the cell cycle regulatory proteins securin and p21, and three small GTPases, Rac1, RhoA and Cdc42 (FIG. 4A). All the fusion proteins demonstrated Shield1-dependent stability, as was the case for YFP. The absence of Shield1 resulted in the degradation of CDK1 (an otherwise stable protein) as well as p21 and securing (cell cycle regulators with relatively short half-lives; Nigg, E. A. (2001) Nature Rev. Mol. Cell. Biol. 2:21-32). Shield1-dependent stability of fusion proteins containing the D100G or L106P destabilizing domain variants fused to the C-terminus of the transcription factor CREB, or the small GTPases, Arf6 and Arl7, (FIG. 4B), was also observed. To date, about 20 fusion proteins have been tested and all demonstrate ligand-dependent stability (Table 4). An additional example is CD8α, a transmembrane glycoprotein found on the surface of T cells, which was able to be detected on the surface of cells by flow cytometry (FIG. 5), in a Shield1-dependent manner. As shown in FIG. 5, the destabilizing FKBP variants D100G and L106P also conferred Shield1-dependent stability to a transmembrane protein, CD8α, when fused at the C-terminus of the transmembrane protein. Here, NIH3T3 cells stably expressing the fusion proteins were divided into three pools (groups). The first group (−) was mock-treated, the second group (+) was treated with 1 μM Shield1 for 24 hrs, and the third group (+/−) was treated with 1 μM Shield1 for 24 hrs, and then washed with media and cultured for 24 hr in the absence of Shield1. Live cells were then probed with a FITC-conjugated anti-CD8a antibody and assayed by flow cytometry. Data are presented as the average mean fluorescence intensity±SEM from an experiment performed in triplicate.

TABLE 4

Proteins destabilized by FKBP Destruction Domains

| 1 | yellow fluorescent protein (YFP) |
|---|---|
| 2 | glycogen synthase kinase-3β |
| 3 | securin |
| 4 | p21$^{WAF/CIP}$ |
| 5 | Rac1 |
| 6 | Cdc42 |
| 7 | RhoA |
| 8 | cAMP response element binding transcription factor (CREB) |
| 9 | cyclin-dependent kinase 1 (CDK1) |
| 10 | Arf6 |
| 11 | Arl7 |
| 12 | cyclin B1 |
| 13 | firefly luciferase |
| 14 | Oct3/4 |
| 15 | Sox2 |
| 16 | Nanog |
| 17 | c-Myc |
| 18 | Klf4 |
| 19 | Aid |
| 20 | Apobec1 |
| 21 | interleukin-2 |

Example 13: Ligand-Dependent Control of Cellular Phenotypes

Figure 4B:
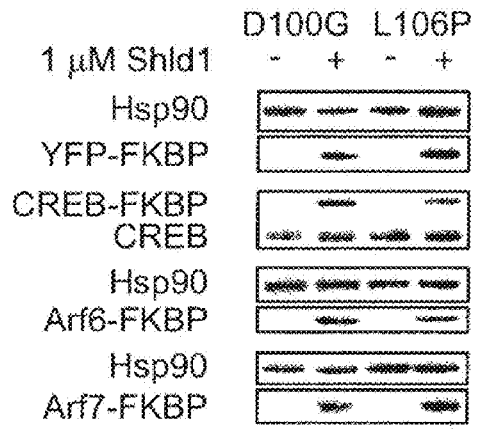

Expression of constitutively active small GTPases causes well-characterized changes in cellular morphology (Heo, W. D. and Meyer, T. (2003) Cell 13:315-328). To determine if FKBP-derived destabilizing domains, in combination with Shield1, could affect cell morphology by modulating GTPases levels, several small GTPases RhoA, Cdc42, or Arl7) were fused to the destabilizing domains (FIGS. 4A and 4B). NIH3T3 cells were individually transduced with the L106P-RhoA, L106P-Cdc42, or Arl7-L106P (note arrangement of fusions), and then mock-treated or treated with Shield1, and visualized using confocal microscopy (not shown). Shield1-treated cells displayed the predicted morphologies, i.e., expression of RhoA induced the formation of stress fibers, expression of Cdc42 resulted in filopodia formation, and expression of Arl7 induced the shrunken cell phenotype (Heo, W. D. and Meyer, T. (2003) *Cell* 113:315-328). Mock treatment with Shield1 produced cells with fibroblast-like morphologies. These GTPase-dependent morphology changes were reversible, as treatment with Shield1 followed by removal of Shield1 also produced cells with fibroblast-like morphologies. The penetrance of the observed phenotype was high, with a large percentage of cells (>90%) exposed to a given experimental condition displaying the predicted behavior (not shown).

Example 14: Cloning and Transfection of Luciferase and IL-2 Genes

Thermostable luciferase or the human IL-2 gene were cloned into pBMN L106P iBlasticidin and used to generate amphotropic retrovirus (Banaszynski, L. A. et al. (2006) *Cell.* 126:995-1004). HCT116 cells were incubated with retrovirus and polybrene (6 µg/mL) for 4 hrs at 37° C. and then selected with Blasticidin (5 µg/mL). Cells grown in 96-well plates (2×10$^4$ cells/well) were treated with Shield1 as indicated and either bioluminescence measured using an IVIS 50 (Xenogen Product from Caliper Life Sciences) following luciferin addition (300 µg/mL), or media collected for ELISA.

Example 15: Mouse Models

SCID or CD1 nu–/nu– mice (Charles River Co.) received subcutaneous dorsal injections of ~1×10$^7$ cells, and tumors were allowed to establish as indicated. Animals were given an intraperitoneal injection of luciferin (225 mg/kg), anesthetized (2% isoflurane), and placed on the warmed stage (3TC) of an IVIS 100 or IVIS 200 (Xenogen Product from Caliper Life Sciences) for imaging. Light produced was measured as photons/sec for designated regions of interest as described. Tumor volumes were also determined by caliper measurement, and mice were sacrificed when tumors reached 1.44 cm$^3$ for survival assays. In some experiments, serum samples were collected by retino-orbital bleedings and tumors collected post-mortem and homogenized for ELISA assay of cytokines. All experiments were run with institutional IACUC approval.

Example 16: Vaccinia Virus Strains

CV1 cells were transfected with pSC-65 p7.5 L106P-tsLuc or pSC-65 p7.5 L106P-TNF-α pSE/L Luc and simultaneously infected with viral growth factor deleted Western Reserve Vaccinia (VSC20). Cassettes were integrated into the viral thymidine kinase gene by homologous recombination and selected by resistance to bromodeoxyuridine on 143B TK$^-$ cells. Single viral plaques were purified in 143B TK$^-$ cells. The same method was used to generate vaccinia virus having the L-L106P-IL-2 construct.

Example 17: vvDD Assays in Cultured Cells

HCT116 cells in a 96-well plate (2×10$^4$ cells/well) were incubated with vvDD carrying an L106P fusion (MOI>1) for 1 hr at 3TC. Virus was removed and cells were treated with Shield1. For luminescence assays, cells were incubated with luciferin (300 µg/mL) and imaged using an IVIS 50 (Xenogen product from Caliper Life Sciences). TNF-α in cell culture media was detected by ELISA.

Example 18: Statistical Analyses

Two-tailed, unpaired Student's T-tests were used, except for comparison of survival curves, when Gehan-Breslow-Wilcoxon test was used. Results were considered significant when $p<0.05$.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An in vivo method for increasing the stability of IL-2 or TNF-α in a mammal comprising:
   (a) introducing into one or more mammalian cells in vitro, a nucleic acid comprising a polynucleotide encoding a fusion protein, wherein the fusion protein comprises in an N-terminal to C-terminal direction:
      i) a signal peptide, wherein the signal peptide facilitates secretion of the fusion protein,
      (ii) a single-polypeptide chain, ligand-dependent, stability-affecting FKBP variant protein, comprising F36V and L106P amino acid substitutions fused to the signal peptide, and
      (iii) IL-2 or TNF-α fused to the stability-affecting FKBP variant protein,
      wherein said introducing generates one or more transformed mammalian cells expressing and secreting the fusion protein;
   (b) implanting the one or more transformed cells from (a) into a mammal harboring a tumor, and
   (c) administering a Shield1 ligand to the mammal from (b), wherein the Shield1 ligand binds to the stability-affecting FKBP variant protein and said binding increases stability of IL-2 or TNF-α by reducing degradation of the fusion protein, increases regulatory T-cell infiltration into tumor cells, and increases the survival rate of the mammal when compared to the same species of mammal constitutively expressing IL-2 or TNF-α.

2. The method of claim 1, wherein the one or more mammal cells are stably transformed with the nucleic acid.

3. The method of claim 1, wherein the nucleic acid sequence is in a viral vector.

4. The method of claim 3, wherein the viral vector is a vaccinia virus.

5. The method of claim 1, wherein the administering of the Shield1 ligand to the mammal is by injecting the ligand into the mammal intraperitoneally or intravenously.

6. The method of claim 1, wherein the introducing of the nucleic acid sequence comprises transforming the one or more mammalian cells in culture with a plasmid comprising the nucleic acid to produce one or more stably transformed mammalian cells, and implanting the one or more transformed cells into a mouse.

7. The method of claim 1, wherein administration of the Shield1 ligand to the mammal reduces the tumor burden of the mammal.

8. An in vivo method for reducing degradation of IL-2 or TNF-α in a mammal comprising:
(a) introducing into a mammal harboring a tumor, a vaccinia virus having a nucleic acid comprising a polynucleotide encoding a fusion protein, wherein the fusion protein comprises in an N-terminal to C-terminal direction:
 i) a signal peptide, wherein the signal peptide facilitates secretion of the fusion protein,
 (ii) a single-polypeptide chain, ligand-dependent, stability-affecting FKBP variant protein, comprising F36V and L106P amino acid substitutions fused to the signal peptide, and
 (iii) IL-2 or TNF-α fused to the stability-affecting FKBP variant protein, and
wherein the IL-2 or TNF-α is expressed and secreted;
(b) administering a Shield1 ligand to the mammal from (a), wherein the Shield1 ligand binds to the stability-affecting FKBP variant protein and said binding increases stability of the IL-2 or TNF-α by reducing degradation of the fusion protein, increases regulatory T-cell infiltration into tumor cells, and increases the survival rate of the mammal when compared to the same species of mammal constitutively expressing IL-2 or TNF-α.

9. The method of claim 8, wherein the administering of the Shield1 ligand to the mammal is by injecting the ligand into the mammal intraperitoneally or intravenously.

10. The method of claim 9, wherein administration of the Shield1 ligand reduces the tumor burden of the mammal.

11. The method of claim 8, wherein administration of the Shield1 ligand reduces the tumor burden of the mammal.

12. The method of claim 8, wherein the fusion protein comprises in an N-terminal to C-terminal direction the signal peptide, the stability-affecting FKBP variant protein and IL-2 or TNF-α.

13. The method of claim 1, wherein after the administering of the Shield1, ligand the level of IL-2 or TNF-α secreted by the transfected cells increases in a dose-dependent manner.

14. The method of claim 8, wherein the level of IL-2 or TNF-α in the serum of the mammal administered the Shield1 ligand increases in a dose-dependent manner.

* * * * *

SEQUENCE LISTING

```
<160> NUMBER OF SEQ ID NOS: 23

<210> SEQ ID NO 1
<211> LENGTH: 107
<212> TYPE: PRT
<213> ORGANISM: Artificial Sequence
<220> FEATURE:
<223> OTHER INFORMATION: FKBP F36V variant

<400> SEQUENCE: 1

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
```

```
                    50                  55                  60
Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                     85                  90                  95

Leu Val Phe Asp Val Glu Leu Leu Lys Leu Glu
                100                 105

<210> SEQ ID NO 2
<211> LENGTH: 107
<212> TYPE: PRT
<213> ORGANISM: Artificial Sequence
<220> FEATURE:
<223> OTHER INFORMATION: FKBP F15S variant

<400> SEQUENCE: 2

Gly Val Gln Val Glu Thr Ile Ser Pro Gly Asp Gly Arg Thr Ser Pro
  1               5                  10                  15

Lys Arg Gly Gln Thr Cys Val Val His Tyr Thr Gly Met Leu Glu Asp
                 20                  25                  30

Gly Lys Lys Phe Asp Ser Ser Arg Asp Arg Asn Lys Pro Phe Lys Phe
             35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                     85                  90                  95

Leu Val Phe Asp Val Glu Leu Leu Lys Leu Glu
                100                 105

<210> SEQ ID NO 3
<211> LENGTH: 107
<212> TYPE: PRT
<213> ORGANISM: Artificial Sequence
<220> FEATURE:
<223> OTHER INFORMATION: FKBP V24A variant

<400> SEQUENCE: 3

Gly Val Gln Val Glu Thr Ile Ser Pro Gly Asp Gly Arg Thr Phe Pro
  1               5                  10                  15

Lys Arg Gly Gln Thr Cys Val Ala His Tyr Thr Gly Met Leu Glu Asp
                 20                  25                  30

Gly Lys Lys Phe Asp Ser Ser Arg Asp Arg Asn Lys Pro Phe Lys Phe
             35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                     85                  90                  95

Leu Val Phe Asp Val Glu Leu Leu Lys Leu Glu
                100                 105

<210> SEQ ID NO 4
<211> LENGTH: 107
<212> TYPE: PRT
<213> ORGANISM: Artificial Sequence
<220> FEATURE:
```

<223> OTHER INFORMATION: FKBP H25R variant

<400> SEQUENCE: 4

Gly Val Gln Val Glu Thr Ile Ser Pro Gly Asp Gly Arg Thr Phe Pro
1               5                   10                  15

Lys Arg Gly Gln Thr Cys Val Val Arg Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 5
<211> LENGTH: 107
<212> TYPE: PRT
<213> ORGANISM: Artificial Sequence
<220> FEATURE:
<223> OTHER INFORMATION: FKBP L106P variant

<400> SEQUENCE: 5

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 6
<211> LENGTH: 107
<212> TYPE: PRT
<213> ORGANISM: Artificial Sequence
<220> FEATURE:
<223> OTHER INFORMATION: FKBP L106P variant

<400> SEQUENCE: 6

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr

```
                65                  70                  75                  80
Ala Tyr Gly Ala Thr Gly His Pro Gly Ile Ile Pro Pro His Ala Thr
                    85                  90                  95

Leu Val Phe Asp Val Glu Leu Leu Lys Pro Glu
                100                 105

<210> SEQ ID NO 7
<211> LENGTH: 107
<212> TYPE: PRT
<213> ORGANISM: Artificial Sequence
<220> FEATURE:
<223> OTHER INFORMATION: FKBP D100G variant

<400> SEQUENCE: 7

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                    85                  90                  95

Leu Val Phe Gly Val Glu Leu Leu Lys Leu Glu
                100                 105

<210> SEQ ID NO 8
<211> LENGTH: 107
<212> TYPE: PRT
<213> ORGANISM: Artificial Sequence
<220> FEATURE:
<223> OTHER INFORMATION: FKBP M66T variant

<400> SEQUENCE: 8

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Thr Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                    85                  90                  95

Leu Val Phe Asp Val Glu Leu Leu Lys Leu Glu
                100                 105

<210> SEQ ID NO 9
<211> LENGTH: 107
<212> TYPE: PRT
<213> ORGANISM: Artificial Sequence
<220> FEATURE:
<223> OTHER INFORMATION: FKBP R71G variant

<400> SEQUENCE: 9
```

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Gly Ala Lys Leu Thr Ile Ser Pro Asp Tyr
65              70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 10
<211> LENGTH: 107
<212> TYPE: PRT
<213> ORGANISM: Artificial Sequence
<220> FEATURE:
<223> OTHER INFORMATION: FKBP D100N variant

<400> SEQUENCE: 10

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65              70                  75                  80

Ala Tyr Gly Ala Thr Gly His Pro Gly Ile Ile Pro Pro His Ala Thr
                85                  90                  95

Leu Val Phe Asn Val Glu Leu Leu Lys Leu Glu
            100                 105

<210> SEQ ID NO 11
<211> LENGTH: 107
<212> TYPE: PRT
<213> ORGANISM: Artificial Sequence
<220> FEATURE:
<223> OTHER INFORMATION: FKBP E102G variant

<400> SEQUENCE: 11

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65              70                  75                  80

Ala Tyr Gly Ala Thr Gly His Pro Gly Ile Ile Pro Pro His Ala Thr

```
                     85                   90                   95

Leu Val Phe Asp Val Gly Leu Leu Lys Leu Glu
                100                 105

<210> SEQ ID NO 12
<211> LENGTH: 107
<212> TYPE: PRT
<213> ORGANISM: Artificial Sequence
<220> FEATURE:
<223> OTHER INFORMATION: FKBP K105I variant

<400> SEQUENCE: 12

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Ile Leu Glu
                100                 105

<210> SEQ ID NO 13
<211> LENGTH: 159
<212> TYPE: PRT
<213> ORGANISM: Artificial Sequence
<220> FEATURE:
<223> OTHER INFORMATION: Wild-type DHFR

<400> SEQUENCE: 13

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
                100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155

<210> SEQ ID NO 14
<211> LENGTH: 159
```

```
<212> TYPE: PRT
<213> ORGANISM: Artificial Sequence
<220> FEATURE:
<223> OTHER INFORMATION: DHFR Y100I variant

<400> SEQUENCE: 14

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 15
<211> LENGTH: 159
<212> TYPE: PRT
<213> ORGANISM: Artificial Sequence
<220> FEATURE:
<223> OTHER INFORMATION: DHFR G121V variant

<400> SEQUENCE: 15

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Val Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 16
```

<211> LENGTH: 159
<212> TYPE: PRT
<213> ORGANISM: Artificial Sequence
<220> FEATURE:
<223> OTHER INFORMATION: DHFR F103L variant

<400> SEQUENCE: 16

```
Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Leu Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

<210> SEQ ID NO 17
<211> LENGTH: 159
<212> TYPE: PRT
<213> ORGANISM: Artificial Sequence
<220> FEATURE:
<223> OTHER INFORMATION: DHFR N18T/A19V variant

<400> SEQUENCE: 17

```
Met Ile Ser Leu Ile Ala Ala Leu Ala Val Asp His Val Ile Gly Met
1               5                   10                  15

Glu Thr Val Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```

-continued

<210> SEQ ID NO 18
<211> LENGTH: 19
<212> TYPE: PRT
<213> ORGANISM: Artificial Sequence
<220> FEATURE:
<223> OTHER INFORMATION: Diversity element sequence

<400> SEQUENCE: 18

Thr Arg Gly Val Glu Glu Val Ala Glu Gly Val Val Leu Leu Arg Arg
1               5                   10                  15

Arg Gly Asn

<210> SEQ ID NO 19
<211> LENGTH: 159
<212> TYPE: PRT
<213> ORGANISM: Artificial Sequence
<220> FEATURE:
<223> OTHER INFORMATION: DHFR H12Y/Y100I variant

<400> SEQUENCE: 19

Met Ile Ser Leu Ile Ala Ala Leu Ala Val Asp Tyr Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
130                 135                 140

Ala Gln Asn Ser His Ser Tyr Cys Phe Glu Ile Leu Glu Arg Arg
145                 150                 155

<210> SEQ ID NO 20
<211> LENGTH: 159
<212> TYPE: PRT
<213> ORGANISM: Artificial Sequence
<220> FEATURE:
<223> OTHER INFORMATION: DHFR H12L/Y100I variant

<400> SEQUENCE: 20

Met Ile Ser Leu Ile Ala Ala Leu Ala Val Asp Leu Val Ile Gly Met
1               5                   10                  15

Glu Asn Ala Met Pro Trp Asn Leu Pro Ala Asp Leu Ala Trp Phe Lys
                20                  25                  30

Arg Asn Thr Leu Asn Lys Pro Val Ile Met Gly Arg His Thr Trp Glu
            35                  40                  45

Ser Ile Gly Arg Pro Leu Pro Gly Arg Lys Asn Ile Ile Leu Ser Ser
        50                  55                  60

Gln Pro Ser Thr Asp Asp Arg Val Thr Trp Val Lys Ser Val Asp Glu
65                  70                  75                  80

```
Ala Ile Ala Ala Cys Gly Asp Val Pro Glu Ile Met Val Ile Gly Gly
                85                  90                  95

Gly Arg Val Ile Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155
```

<210> SEQ ID NO 21
<211> LENGTH: 159
<212> TYPE: PRT
<213> ORGANISM: Artificial Sequence
<220> FEATURE:
<223> OTHER INFORMATION: HDFR R98H/F103S variant

<400> SEQUENCE: 21

```
Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly His Val Tyr Glu Gln Ser Leu Pro Lys Ala Gln Lys Leu Tyr Leu
            100                 105                 110

Thr His Ile Asp Ala Glu Val Glu Gly Asp Thr His Phe Pro Asp Tyr
            115                 120                 125

Glu Pro Asp Asp Trp Glu Ser Val Phe Ser Glu Phe His Asp Ala Asp
        130                 135                 140

Ala Gln Asn Ser His Ser Tyr Cys Phe Glu Ile Leu Glu Arg Arg
145                 150                 155
```

<210> SEQ ID NO 22
<211> LENGTH: 159
<212> TYPE: PRT
<213> ORGANISM: Artificial Sequence
<220> FEATURE:
<223> OTHER INFORMATION: DHFR M42T/H114R variant

<400> SEQUENCE: 22

```
Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Thr Gly Arg His Thr Trp Glu
        35                  40                  45

Ser Ile Gly Arg Pro Leu Pro Gly Arg Lys Asn Ile Ile Leu Ser Ser
    50                  55                  60

Gln Pro Ser Thr Asp Asp Arg Val Thr Trp Val Lys Ser Val Asp Glu
65                  70                  75                  80
```

```
Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr Arg Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155

<210> SEQ ID NO 23
<211> LENGTH: 159
<212> TYPE: PRT
<213> ORGANISM: Artificial Sequence
<220> FEATURE:
<223> OTHER INFORMATION: DHFR I61F/T68S variant

<400> SEQUENCE: 23

Met Ile Ser Leu Ile Ala Ala Leu Ala Val Asp His Val Ile Gly Met
1               5                   10                  15

Glu Asn Ala Met Pro Trp Asn Leu Pro Ala Asp Leu Ala Trp Phe Lys
            20                  25                  30

Arg Asn Thr Leu Asn Lys Pro Val Ile Met Gly Arg His Thr Trp Glu
        35                  40                  45

Ser Ile Gly Arg Pro Leu Pro Gly Arg Lys Asn Ile Phe Leu Ser Ser
    50                  55                  60

Gln Pro Ser Ser Asp Asp Arg Val Thr Trp Val Lys Ser Val Asp Glu
65                  70                  75                  80

Ala Ile Ala Ala Cys Gly Asp Val Pro Glu Ile Met Val Ile Gly Gly
                85                  90                  95

Gly Arg Val Tyr Glu Gln Phe Leu Pro Lys Ala Gln Lys Leu Tyr Leu
            100                 105                 110

Thr His Ile Asp Ala Glu Val Glu Gly Asp Thr His Phe Pro Asp Tyr
        115                 120                 125

Glu Pro Asp Asp Trp Glu Ser Val Phe Ser Glu Phe His Asp Ala Asp
    130                 135                 140

Ala Gln Asn Ser His Ser Tyr Cys Phe Glu Ile Leu Glu Arg Arg
145                 150                 155
```